(12) United States Patent
Tsuchihashi et al.

(10) Patent No.: US 11,889,846 B2
(45) Date of Patent: Feb. 6, 2024

(54) METHOD FOR PRODUCING FERMENTED FOOD, FERMENTED FOOD, AND LACTIC ACID BACTERIA-CONTAINING COMPOSITION

(71) Applicant: MEIJI CO., LTD., Tokyo (JP)

(72) Inventors: Hanae Tsuchihashi, Hachioji (JP); Eri Yamamoto, Hachioji (JP); Yoshitaka Kawai, Hachioji (JP); Mizue Saito, Hachioji (JP); Mariko Takeda, Hachioji (JP); Ayumi Ichikawa, Hachioji (JP); Atsuko Ueno, Hachioji (JP)

(73) Assignee: MEIJI CO., LTD., Tokyo (JP)

( * ) Notice: Subject to any disclaimer, the term of this patent is extended or adjusted under 35 U.S.C. 154(b) by 114 days.

(21) Appl. No.: 17/521,236

(22) Filed: Nov. 8, 2021

(65) Prior Publication Data

US 2022/0087274 A1    Mar. 24, 2022

Related U.S. Application Data

(62) Division of application No. 16/797,108, filed on Feb. 21, 2020, now Pat. No. 11,197,484.

(30) Foreign Application Priority Data

Feb. 22, 2019    (JP) ................................. 2019-030817

(51) Int. Cl.
| | |
|---|---|
| *C12N 1/38* | (2006.01) |
| *A23C 9/123* | (2006.01) |
| *C12N 15/01* | (2006.01) |
| *C12N 1/20* | (2006.01) |
| *C12R 1/225* | (2006.01) |

(52) U.S. Cl.
CPC ............ *A23C 9/1234* (2013.01); *C12N 15/01* (2013.01); *C12N 1/205* (2021.05); *C12R 2001/225* (2021.05)

(58) Field of Classification Search
CPC ........ A23C 9/1234; C12N 15/01; C12R 1/225
USPC .......................................................... 426/43
See application file for complete search history.

(56) References Cited

U.S. PATENT DOCUMENTS

| 2015/0086675 A1 | 3/2015 | Johansen et al. |
| 2019/0357556 A1 | 11/2019 | Kashiwagi et al. |

FOREIGN PATENT DOCUMENTS

| JP | 2008-237198 | 10/2008 |
| JP | 2015-518374 | 7/2015 |
| JP | 2017-221157 | 12/2017 |
| WO | 2018/151249 | 8/2018 |

OTHER PUBLICATIONS

Courtin et al., Cell-wall proteinases PrtS and PrtB have a different role in *Streptococcus thermophilus*/Lactobacillus bulgaricus mixed cultures in milk, Microbiology. (Year: 2002).*

(Continued)

*Primary Examiner* — Brent T O'Hern
(74) *Attorney, Agent, or Firm* — Wenderoth, Lind & Ponack, L.L.P.

(57) ABSTRACT

The present invention provides a lactic acid bacteria-containing composition comprising a *Lactobacillus delbrueckii* and a *Streptococcus thermophilus*.

6 Claims, 46 Drawing Sheets

Specification includes a Sequence Listing.

(56) References Cited

OTHER PUBLICATIONS

Song et al., Genetic diversity and population structure of *Lactobacillus delbrueckii* subspecies *bulgaricus* isolated from naturally fermented dairy foods, Scientific Reports. (Year: 2016).*

Office Action dated Jan. 11, 2023 in corresponding Japanese Patent Application No. 2020-027755, with English language translation.

Wessarn Galia et al., "Variability and molecular typing of *Streptococcus thermophilus* strains displaying different proteolytic and acidifying properties", International Dairy Journal, vol. 19, pp. 89-95, 2009.

Adimpong, D.B., et al., "*Lactobacillus delbrueckii* subsp. *jakobsenii* subsp. nov., isolated from dolo wort, an alcoholic fermented beverage in Burkina Faso", International Journal of Systematic and Evolutionary Microbiology, 2013, vol. 63, pp. 3720-3726.

Tanigawa, K., et al., "Multilocus sequence typing reveals a novel subspeciation of Lactobacillus delbrueckii", Microbiology, 2011, vol. 157, pp. 727-738.

Courtin, P., et al., "Cell-wall proteinases PrtS and PrtB have a different role in *Streptococcus thermophilus*/Lactobacillus bulgaricus mixed cultures in milk", Microbiology, 2002, vol. 148, pp. 3413-3421.

Song, Y., et al., "Genetic diversity and population structure of *Lactobacillus delbrueckii* subspecies *bulgaricus* isolated from naturally fermented dairy foods", Scientific Reports, 2016, pp. 1-8.

* cited by examiner

| | | | |
|---|---|---|---|
| fusA-1 | 401 | TTGAAGGCCTTCCCAGTATTTGCTGGTTCAGCCCTTCAAGAACAAGGGTGTGCAAATGATGCTTGACGGTGTTGT | 474 |
| fusA-2 | 401 | .......................................................................... | 474 |
| fusA-3 | 401 | .......................................................................... | 474 |
| fusA-4 | 401 | .......................................................................... | 474 |
| fusA-5 | 401 | .......................................................................... | 474 |
| fusA-6 | 401 | .....A.................................................................... | 474 |
| fusA-7 | 401 | .......................................................................... | 474 |
| fusA-8 | 401 | .......................................................................... | 474 |
| fusA-9 | 401 | .......................................................................... | 474 |
| fusA-10 | 401 | .......................................................................... | 474 |
| fusA-11 | 401 | .......................................................................... | 474 |
| fusA-12 | 401 | .......................................................................... | 474 |
| fusA-13 | 401 | .......................................................................... | 474 |
| fusA-14 | 401 | .......................................................................... | 474 |
| fusA-17 | 401 | .......................................................................... | 474 |
| fusA-18 | 401 | .......................................................................... | 474 |

| | | |
|---|---|---|
| hsp60-1 | 1 GCCATCGTGCAAGAAGGGATGAAGAACGTGGTTGCCGGGGCTAACCCAGTTGGCATTCGCCGCGGGGATTGAAAAGGCCACCCAAGCAGCCGTTGACCAAT | 100 |
| hsp60-2 | 1 .................................................................................................... | 100 |
| hsp60-3 | 1 .................................................................................................... | 100 |
| hsp60-4 | 1 .................................................................................................... | 100 |
| hsp60-5 | 1 ............................................................................A....................... | 100 |
| hsp60-6 | 1 .................................................................................................... | 100 |
| hsp60-7 | 1 .................................................................................................... | 100 |
| hsp60-8 | 1 .................................................................................................... | 100 |
| hsp60-9 | 1 ..........................................................G......................................... | 100 |
| hsp60-10 | 1 .................................................................................................... | 100 |
| hsp60-11 | 1 ..............................................................................G..................... | 100 |
| hsp60-12 | 1 .................................................................................................... | 100 |
| hsp60-13 | 1 .................................................................................................... | 100 |
| hsp60-14 | 1 ..........................................T......................................................... | 100 |
| hsp60-15 | 1 .................................................................................G................... | 100 |
| hsp60-16 | 1 ......T............................................................................................. | 100 |
| hsp60-17 | 1 .................................................................................................... | 100 |
| hsp60-18 | 1 ..........................................T.........................................G............... | 100 |
| hsp60-19 | 1 .................................................................................................... | 100 |
| hsp60-26 | 1 .................................................................................................... | 100 |
| hsp60-27 | 1 .................................................................................................... | 100 |

Fig. 4B

| | | | |
|---|---|---|---|
|hsp60-1|101|TGCACAAGAACAGCCACGAAGTTCCAGCCGGGACCAAATTGCCAAGTTGCTTCAATCTCAAGTGCTTCAAAGGAAATCGGCGACTGATCGCTGAAGC|200|
|hsp60-2|101|..........................................................................................|200|
|hsp60-3|101|..........................................................................................|200|
|hsp60-4|101|...................A......................................................................|200|
|hsp60-5|101|...................A......................................................................|200|
|hsp60-6|101|................A.........................................A...............................|200|
|hsp60-7|101|................A.........................................................T...............|200|
|hsp60-8|101|................A.........................................................................|200|
|hsp60-9|101|...................A......................................................................|200|
|hsp60-10|101|..........................................................................................|200|
|hsp60-11|101|...................A...............T.......................................................|200|
|hsp60-12|101|...................A.................T.....................................................|200|
|hsp60-13|101|..........................................................................................|200|
|hsp60-14|101|..........................................................................................|200|
|hsp60-15|101|..........................................................................................|200|
|hsp60-16|101|..........................................................................................|200|
|hsp60-17|101|..........................................................................................|200|
|hsp60-18|101|.................................A........................................................|200|
|hsp60-19|101|..........................................................................................|200|
|hsp60-26|101|...................A......................................................................|200|
|hsp60-27|101|..........................................................................................|200|

Fig. 4C

| | | | | |
|---|---|---|---|---|
| hsp60-1 | 201 | CATGGAAAAGGTGGCAAAGAGACGGTGTTATCACCATTGAAGACTCCCGCGGGATGGAAACTGAACTGAGCGTGGTTGAAGGATGCAATCGACGCGGC | 300 |
| hsp60-2 | 201 | ..........................G..................................................................... | 300 |
| hsp60-3 | 201 | ..........................G..................................................................... | 300 |
| hsp60-4 | 201 | .................................................................................................| 300 |
| hsp60-5 | 201 | ..........................G..................................................................... | 300 |
| hsp60-6 | 201 | ..........................G..................................................................... | 300 |
| hsp60-7 | 201 | ..........................T..................................................................... | 300 |
| hsp60-8 | 201 | ..........................G..................................................................... | 300 |
| hsp60-9 | 201 | .................................................................................................| 300 |
| hsp60-10 | 201 | ..........................G..................................................................... | 300 |
| hsp60-11 | 201 | ..........................T..................................................................... | 300 |
| hsp60-12 | 201 | ..........................G..................................................................... | 300 |
| hsp60-13 | 201 | ..........................G..................................................................... | 300 |
| hsp60-14 | 201 | ..........................G..................................................................... | 300 |
| hsp60-15 | 201 | ..........................G..................................................................... | 300 |
| hsp60-16 | 201 | ..........................G..................................................................... | 300 |
| hsp60-17 | 201 | ..........................G..................................................................... | 300 |
| hsp60-18 | 201 | ..........................G..................................................................... | 300 |
| hsp60-19 | 201 | ..........................G..................................................................... | 300 |
| hsp60-26 | 201 | ...................T............................................................................. | 300 |
| hsp60-27 | 201 | .................................................................................................| 300 |

| | | | | | |
|---|---|---|---|---|---|
| hsp60-1 | 401 | ACATTTTGGCAATGTTTGCAGGAAGGCAGAAATCGTGAAGGAAGGCCGCTCACTCCTAATCATCGCTGATGACTGACTGGCGAAGCTTGCCAACTCTTGTTTGAA | 500 |
| hsp60-2 | 401 | .................................................................................................... | 500 |
| hsp60-3 | 401 | ......................C.AC......................................................................... | 500 |
| hsp60-4 | 401 | ......................C.AC......................................................................... | 500 |
| hsp60-5 | 401 | ....C.................C.AC......................................................................... | 500 |
| hsp60-6 | 401 | ....C.................C.AC......................................................................... | 500 |
| hsp60-7 | 401 | ....C.................C.AC...........G............................................................. | 500 |
| hsp60-8 | 401 | ....C.................C.AC...........G............................................................. | 500 |
| hsp60-9 | 401 | ....C.................C.AC...........G............................................................. | 500 |
| hsp60-10 | 401 | ......................A.............G.............................................................. | 500 |
| hsp60-11 | 401 | ....C.................C.AC.......................................................................... | 500 |
| hsp60-12 | 401 | ....C.................C.AC.......................................................................... | 500 |
| hsp60-13 | 401 | ......................C.AC.......................................................................... | 500 |
| hsp60-14 | 401 | ......................C.AC.......................................................................... | 500 |
| hsp60-15 | 401 | ......................C.AC.......................................................................... | 500 |
| hsp60-16 | 401 | ......................C.AC.......................................................................... | 500 |
| hsp60-17 | 401 | ......................C.AC.......................................................................... | 500 |
| hsp60-18 | 401 | ......................A..................................................................T......... | 500 |
| hsp60-19 | 401 | ......................C.AC.......................................................................... | 500 |
| hsp60-26 | 401 | ......................A...................................................................T........ | 500 |
| hsp60-27 | 401 | ......................A............................................................................ | 500 |

Fig. 4F

| | | | |
|---|---|---|---|
| hsp60-1 | 501 | CAAGATCCGCG | 511 |
| hsp60-2 | 501 | ........... | 511 |
| hsp60-3 | 501 | ........... | 511 |
| hsp60-4 | 501 | ........... | 511 |
| hsp60-5 | 501 | ........... | 511 |
| hsp60-6 | 501 | ........... | 511 |
| hsp60-7 | 501 | ........... | 511 |
| hsp60-8 | 501 | ........... | 511 |
| hsp60-9 | 501 | ........... | 511 |
| hsp60-10 | 501 | ........... | 511 |
| hsp60-11 | 501 | ........... | 511 |
| hsp60-12 | 501 | ........... | 511 |
| hsp60-13 | 501 | ........... | 511 |
| hsp60-14 | 501 | ........... | 511 |
| hsp60-15 | 501 | ........... | 511 |
| hsp60-16 | 501 | ........... | 511 |
| hsp60-17 | 501 | ........... | 511 |
| hsp60-18 | 501 | ........... | 511 |
| hsp60-19 | 501 | ........... | 511 |
| hsp60-26 | 501 | ........... | 511 |
| hsp60-27 | 501 | ........... | 511 |

| | | | |
|---|---|---|---|
| recA-1 | 401 | ATCCGGGAAAAG | 412 |
| recA-2 | 401 | ............ | 412 |
| recA-3 | 401 | ............ | 412 |
| recA-4 | 401 | ............ | 412 |
| recA-5 | 401 | ............ | 412 |
| recA-6 | 401 | ............ | 412 |
| recA-7 | 401 | ............ | 412 |
| recA-8 | 401 | ............ | 412 |
| recA-9 | 401 | ............ | 412 |
| recA-10 | 401 | ............ | 412 |
| recA-11 | 401 | ............ | 412 |
| recA-12 | 401 | ............ | 412 |
| recA-13 | 401 | ............ | 412 |
| recA-14 | 401 | ............ | 412 |
| recA-15 | 401 | ............ | 412 |
| recA-16 | 401 | ............ | 412 |
| recA-17 | 401 | ............ | 412 |
| recA-18 | 401 | ............ | 412 |
| recA-24 | 401 | ............ | 412 |
| recA-28 | 401 | ..T......... | 412 |

| | | | | |
|---|---|---|---|---|
| recG-1 | 101 | CTACAAGGAGCTGGCTGATGGCCAGCATTAATGTGGTGATCGGCACCCATCGGCCTTGATCGGAAGAGCAAGTGTCCTTTAAAAAGCTGGGCCTGGTTATTATC | 200 |
| recG-2 | 101 | .................................................................................................... | 200 |
| recG-3 | 101 | .................................................................................................... | 200 |
| recG-4 | 101 | .........................T.................C......................................G............... | 200 |
| recG-5 | 101 | .........................T.................C......................................G............... | 200 |
| recG-6 | 101 | .............................................C....................................G............... | 200 |
| recG-7 | 101 | .............................................C...................................AG............... | 200 |
| recG-8 | 101 | .............................................C...................................AG............... | 200 |
| recG-9 | 101 | .............................................C......................................G............... | 200 |
| recG-10 | 101 | .............................................C......................................G............... | 200 |
| recG-11 | 101 | .............................................C......................................G............... | 200 |
| recG-12 | 101 | .............................................C......................................G............... | 200 |
| recG-13 | 101 | ......................................................................C.............G............... | 200 |
| recG-14 | 101 | .............................................C......................................G............... | 200 |
| recG-15 | 101 | .............................................C......................................G............... | 200 |
| recG-16 | 101 | ......................................................................................G............... | 200 |
| recG-17 | 101 | ......................................................................................G............... | 200 |
| recG-18 | 101 | ......................................................................................G............... | 200 |
| recG-19 | 101 | ......................................................................................G............... | 200 |
| recG-20 | 101 | .............................................C......................................G............... | 200 |
| recG-21 | 101 | .............................................C......................................G............... | 200 |
| recG-22 | 101 | .............................................C......................................G............... | 200 |
| recG-38 | 101 | .............................................C......................................G............... | 200 |
| recG-40 | 101 | ......................................................................................G............... | 200 |

```
                             SEQUENCE LISTING

<160> NUMBER OF SEQ ID NOS: 42

<210> SEQ ID NO 1
<211> LENGTH: 474
<212> TYPE: DNA
<213> ORGANISM: Lactobacillus delbrueckii

<400> SEQUENCE: 1
cgtttggcgt caagctgaaa actacggtgt tccgcggatc gtcttcgtta acaagatgga     60
caagattggt gccaacttcg acttctcagt taagagtctg cacgaacgtt tgaacgctaa    120
cgctatcgcc gttcaaatgc ctatcggtgc tgaagaccaa ttcgaaggcg ttatcgactt    180
gttcgacatg gttgccgacg tctacgacga agacaagctg ggcgcaaact gggaaactat    240
tccagttcca gacgaataca aggaagaagc tgaaagccgt cgtgaagaaa tgatcgaagc    300
gatcgctgaa gttgacgacg acattatgga aaagttcctt ggcggtgaag aaatctccaa    360
cgaagaactt aaggctgcct tgcgccgggc aactttggac ttgaaggcct tcccagtatt    420
tgctggttca gccttcaaga acaagggtgt gcaaatgatg cttgacggtg ttgt           474

<210> SEQ ID NO 2
<211> LENGTH: 474
<212> TYPE: DNA
<213> ORGANISM: Lactobacillus delbrueckii

<400> SEQUENCE: 2
cgtttggcgt caagctgaaa actacggtgt tccgcggatc gtcttcgtta acaagatgga     60
caagatcggt gccaacttcg acttctcagt taagagtctg cacgaacgtt tgaacgctaa    120
cgctatcgcc gttcaaatgc ctatcggtgc tgaagaccaa ttcgaaggcg ttatcgactt    180
gttcgacatg gttgccgacg tctacgacga agacaagctg ggcgcaaact gggaaactat    240
tccagttcca gacgaataca aggaagaagc cgaaagccgt cgtgaagaaa tgatcgaaga    300
gatcgctgaa gttgacgacg acattatgga aaagttcctt ggcggtgaag aaatctccaa    360
tgaagaactt aaggctgcct tgcgccgggc aactttggac ttgaaggcct tcccagtatt    420
tgctggttca gccttcaaga acaagggtgt gcaaatgatg cttgacggtg ttgt           474

<210> SEQ ID NO 3
<211> LENGTH: 474
<212> TYPE: DNA
<213> ORGANISM: Lactobacillus delbrueckii

<400> SEQUENCE: 3
cgtttggcgt caagctgaaa actacggtgt tccgcggatc gtcttcgtta acaagatgga     60
caagatcggt gctaacttcg acttctcagt taagagtctg cacgaacgtt tgaacgctaa    120
cgctatcgcc gttcaaatgc ctatcggtgc tgaagaccaa ttcgaaggcg ttatcgactt    180
gttcgacatg gttgccgacg tctacgacga agacaagctg ggcgcaaact gggaaactat    240
tccagttcca gacgaataca aggaagaagc cgaaagccgt cgtgaagaaa tgatcgaaga    300
gatcgctgaa gttgacgacg acattatgga aaagttcctt ggcggtgaag aaatctccaa    360
```

```
cgaagaactt aaggctgcct tgcgccgggc aactttggac ttgaaggcct tcccagtatt    420
tgctggttca gccttcaaga acaagggtgt gcaaatgatg cttgacggtg ttgt           474

<210> SEQ ID NO 4
<211> LENGTH: 474
<212> TYPE: DNA
<213> ORGANISM: Lactobacillus delbrueckii

<400> SEQUENCE: 4
cgtttggcgt caagctgaaa actacggtgt tccgcggatc gtcttcgtta acaagatgga     60
caagattggt gccaacttcg actttttcagt taagagtctg cacgaacgtt tgaacgctaa   120
cgctatcgcc gttcaaatgc ctatcggtgc tgaagaccaa ttcgaaggcg ttatcgactt    180
gttcgacatg gttgccgacg tctacgacga agacaagctg ggcgcaaact gggaaactat    240
tccagttcca gacgaataca aggaagaagc tgaaagccgt cgtgaagaaa tgatcgaaga    300
gatcgctgaa gttgacgacg acattatgga aaagttcctt ggcggtgaag aaatctccaa    360
cgaagaactt aaggctgcct tgcgccgggc aactttggac ttgaaggcct tcccagtatt    420
tgctggttca gccttcaaga acaagggtgt gcaaatgatg cttgacggtg ttgt           474

<210> SEQ ID NO 5
<211> LENGTH: 380
<212> TYPE: DNA
<213> ORGANISM: Lactobacillus delbrueckii

<400> SEQUENCE: 5
cgttgaaaag gggcaactgg ccgaaagagc cagagttgcc gccaagcgcg cccgggaagt     60
tacccggaag aagtccggcc tgaaatcgc caacctgcca gcaaattgg ccgacaacac     120 ttcaaatgac ccgaacatct cagaactctt catcgtcgaa ggggactctg ccggcggcag    180
cgccaagcaa gggcggagcc ggctgaccca ggccatcctg cccatccggg ggaagatcct    240
gaacgtggaa aaggcctcaa tggaccggat cctggccaac caggaaatcc ggactctgtt    300
tacggccctg gggaccggct ttggggcaga cttttgacgtc tccaaggccc gctatcacaa    360
gctgatcatc atgactgacg                                                 380

<210> SEQ ID NO 6
<211> LENGTH: 380
<212> TYPE: DNA
<213> ORGANISM: Lactobacillus delbrueckii

<400> SEQUENCE: 6
cgttgaaaag gggcaactgg ccgaaagagc cagagttgcc gccaagcgcg cccgggaagt     60
tacccggaag aagtccggcc tgaaatcgc caacctgcca gcaaattgg ccgacaacac     120 ttcaaatgac ccgaacatct cagaactctt catcgtcgaa ggggactccg ccggcggcag    180
cgccaagcaa gggcggagcc ggctgaccca ggccatcctg cccatccggg ggaagatcct    240
gaacgtggaa aaggcctcaa tggaccggat cctggccaac caggaaatcc ggactctgtt    300
tacggccctg gggaccggct ttggggcaga cttttgacatc tccaaggccc gctatcacaa    360
gctgattatc atgactgacg                                                 380

<210> SEQ ID NO 7
<211> LENGTH: 380
<212> TYPE: DNA
<213> ORGANISM: Lactobacillus delbrueckii
```

```
<400> SEQUENCE: 7
cgttgaaaag gggcaactgg ccgaaagagc cagagttgcc gccaagcgcg cccgggaagt      60
tacccggaag aagtccggcc tggaaatcgc caacctgcca ggcaaattgg ccgacaacac     120
ttcaaatgac ccgaacatct cagaactctt catcgtcgaa ggggactccg ccggcggcag     180
cgccaagcaa gggcggagcc ggctgaccca ggccatcctg cccatccggg ggaagatcct     240
gaacgtggaa aaggcctcaa tgatcggat cctggccaac caggaaatcc ggactctgtt      300
tacggccctg gggaccggct ttggggcaga cttttgacatc tccaaggccc gctatcacaa    360
gctgatcatc atgactgacg                                                 380

<210> SEQ ID NO 8
<211> LENGTH: 380
<212> TYPE: DNA
<213> ORGANISM: Lactobacillus delbrueckii

<400> SEQUENCE: 8
cgtggaaaag gggcaactgg ctgaaagagc cagagttgcc gccaagcgcg cccgggaagt      60
tacccggaag aagtccggcc tggaaatcgc caacctgcca ggcaaattgg ccgacaacac     120
ttcaaatgac ccgaacatct cagaactctt catcgtcgaa ggggactccg ccggcggcag     180
cgccaagcaa gggcggagcc ggctgaccca ggccatcctg cccatccggg ggaagatcct     240
gaacgtggaa aaggcctcaa tgaccggat cctggccaac caggaaatcc ggactctgtt      300
tacggccctg gggaccggct ttggggcaga cttttgacgtc tccaaggccc gctatcacaa    360
gctgatcatc atgactgacg                                                 380

<210> SEQ ID NO 9
<211> LENGTH: 380
<212> TYPE: DNA
<213> ORGANISM: Lactobacillus delbrueckii

<400> SEQUENCE: 9
cgttgaaaag gggcaactgg ccgaaagagc cagagttgcc gccaagcgcg cccgggaagt      60
tacccggaag aagtccggcc tggaaatcgc caacctgcca ggcaaattgg ccgacaacac     120
ttcaaatgac ccgaacatct cagaactctt catcgtcgaa ggggactccg ccggcggcag     180
cgccaagcaa gggcggagcc ggctgaccca ggccatccta cccatccggg ggaagatcct     240
gaacgtggaa aaggcctcaa tgaccggat cctggccaac caggaaatcc ggactctgtt      300
tacggccctg gggaccggct ttggggcaga cttttgacgtc tccaaggccc gctatcacaa    360
gctgatcatc atgactgacg                                                 380

<210> SEQ ID NO 10
<211> LENGTH: 511
<212> TYPE: DNA
<213> ORGANISM: Lactobacillus delbrueckii

<400> SEQUENCE: 10
gccatcgtgc aagaagggat gaagaacgtg gttgccgggg ctaacccagt tggcattcgc      60
cgcgggattg aaaaggccac ccaagcagcc gttgaccaat gcacaagaa cagccacgaa      120 gtttccagcc gggaccaaat tgcccaagtt gcttcaatct caagtgcttc aaaggaaatc     180
ggcgacttga tcgctgaagc catggaaaag gtcggcaagg acggtgttat caccattgaa     240
gactcccgcg gatcgaaaac tgaactgagc gtggttgaag gatgcaatt cgaccgcggc      300 tacctgtccc aatacatggt aacggacaac gacaagatgg aagctgactt ggaaaaccca     360
```

| | |
|---|---:|
| tacatcttga tcactgacaa gaagatttcc aacatccagg acattttgcc aatgttgcag | 420 |
| gaaatcgtga agaaggccg ctcactccta atcatcgctg atgacgtgac tggtgaagct | 480 |
| ttgccaactc ttgttttgaa caagatccgc g | 511 |

<210> SEQ ID NO 11
<211> LENGTH: 511
<212> TYPE: DNA
<213> ORGANISM: Lactobacillus delbrueckii

<400> SEQUENCE: 11

| | |
|---|---:|
| gccatcgtgc aagaagggat gaagaatgtg gttgccgggg ctaacccagt tggcattcgc | 60 |
| cgcgggattg aaaaggccac ccaagcagcc gttgaccaat tgcacaagaa cagccacgaa | 120 |
| gtttccagac gggaccaaat tgcccaagtt gcttcaatct caagtgcttc aaaggaaatc | 180 |
| ggcgacttga tcgctgaagc catggaaaag gtcggcaagg acggtgttat caccattgaa | 240 |
| gactcccgcg ggatcgaaac tgaactgagc gtggttgaag gatgcaatt cgaccgcggc | 300 |
| tacctgtccc aatacatggt aacggacaac gacaagatgg aagctgactt ggaaaaccca | 360 |
| tacatcttga tcactgacaa gaagatttcc aacatccagg acattttgcc aatgttgcag | 420 |
| gaaatcgtgc aacaaggccg ctcactccta atcatcgctg atgacgtgac tggcgaagct | 480 |
| ttgccaactc ttgttttgaa caagatccgc g | 511 |

<210> SEQ ID NO 12
<211> LENGTH: 511
<212> TYPE: DNA
<213> ORGANISM: Lactobacillus delbrueckii

<400> SEQUENCE: 12

| | |
|---|---:|
| gccatcgtgc aagaagggat gaagaacgtg gttgccgggg ctaacccagt tggcattcgc | 60 |
| cgcgggattg aaaaggccac ccaagcagcc gttgaccaat tgcacaagaa cagccacgaa | 120 |
| gtttccagcc gggaccaaat tgcccaagtt gcttcaatct caagtgcttc aaaggaaatc | 180 |
| ggcgacttga tcgctgaagc catggaaaat gtcggcaaag acggtgttat caccattgaa | 240 |
| gactcccgcg ggatcgaaac tgaactgagc gtggttgaag gatgcaatt cgaccgcggc | 300 |
| tacctgtccc aatacatggt aacggacaac gacaagatgg aagctgactt ggaaaaccca | 360 |
| tacatcttga tcactgacaa gaagatttcc aacatccagg acattttgcc aatgttgcag | 420 |
| gaaatcgtga agaaggccg ctcactccta atcatcgctg atgacgtgac tggcgaagct | 480 |
| ttgccaactc ttgttttgaa caagatccgc g | 511 |

<210> SEQ ID NO 13
<211> LENGTH: 496
<212> TYPE: DNA
<213> ORGANISM: Lactobacillus delbrueckii

<400> SEQUENCE: 13

| | |
|---|---:|
| atggacaaca agggctgctt cactgaagaa atccctgacc cggacctggt gggcaagttc | 60 |
| tacactgaca ccaacgaaat cgtcaaggac aagctggcgg ctgccggcaa ccttttgcac | 120 |
| tacagcacct ttgtccactc cgccgctcac gactggcgga ccaagaagcc ggtagtctac | 180 |
| cgggcaacca cgcaatggtt tgcctcaatc tccaagttca gagaccagat cctggaccag | 240 |
| attgaaaaga ccacctttta cccggcctgg ggaaagaccc gcctttacaa catgatcaag | 300 |
| gaccggggcg actgggtaat ttcccgccaa cgtgcctggg gcgtgccttt gccaatcttc | 360 |

```
tacgctgaag acggcaccgc catcgtgacg catgaaacca tcgaacacgt ggctgacctc   420
tttgccaagg aaggctccaa cgcctggttc acccacccgg ttgaagaact tttgccagaa   480
ggctttactt cagaac                                                    496

<210> SEQ ID NO 14
<211> LENGTH: 496
<212> TYPE: DNA
<213> ORGANISM: Lactobacillus delbrueckii

<400> SEQUENCE: 14
atggataaca agggctgctt cactgaagaa atccctgacc cggacctggt gggcaagttc    60
tacactgaca ccaacgaaat cgtcaaggac aagctggcgg ctgccggcaa ccttttgcac   120
tacagcacct ttgtccactc cgccgctcac gactggcgga ccaagaagcc ggtagtctac   180
cgggcaacca cgcaatggtt tgcctcaatc tccaagttca gagaccagat cctggaccag   240
attgaaaaga ccaccttcta cccggcctgg ggcaagaccc gcctttacaa catgatcaag   300
gaccggggcg attgggtaat ttcccgccaa cgtgcctggg gcgtgccttt gccaatcttc   360
tacgctgaag acggcaccgc catcgtgacg catgaaacca tcgaacacgt ggctgacctc   420
tttgccaagg aaggctccaa cgcctggttc acccacccgg ttgaagaact tttgccagaa   480
ggctttactt cagaac                                                    496

<210> SEQ ID NO 15
<211> LENGTH: 496
<212> TYPE: DNA
<213> ORGANISM: Lactobacillus delbrueckii

<400> SEQUENCE: 15
atggacaaca agggctgctt cactgaagaa atccctgacc cggacctggt gggcaagttc    60
tacgctgaca ccaacgaaat cgtcaaggac aagctggcgg ctgccggcaa ccttttgcac   120
tacagcacct ttgtccactc cgccgctcac gactggcgga ccaagaagcc ggtagtctac   180
cgggcaacca cgcaatggtt tgcctcaatc tccaagttca gagaccagat cctggaccag   240
attgaaaaga ccaccttcta cccggcctgg ggcaagaccc gcctttacaa catgatcaag   300
gaccggggcg gttgggtaat ttcccgccaa cgtgcctggg gcgtgccttt gccaatcttc   360
tacgctgaag acggcaccgc catcgtgacg catgaaacca tcgaacacgt ggctgacctc   420
tttgccaagg aaggctccaa cgcctggttc acccacccgg ttgaagaact tttgccagaa   480
ggctttactt cagaac                                                    496

<210> SEQ ID NO 16
<211> LENGTH: 496
<212> TYPE: DNA
<213> ORGANISM: Lactobacillus delbrueckii

<400> SEQUENCE: 16
atggacaaca agggctgctt cactgaagaa atccctgacc cggacctggt gggcaagttc    60
tacgctgaca ccaacgaaat cgtcaaggac aagctggcgg ctgccggcaa ccttttgcac   120
tacagcacct ttgtccactc cgccgctcac gactggcgga ccaagaagcc ggtagtctac   180
cgggcaacca cgcaatggtt tgcctcaatc tccaagttca gagaccagat cctggaccag   240
attgaaaaga ccaccttcta cccggcctgg ggcaagaccc gcctttacaa catgatcaag   300
gaccggggcg attgggtaat ttcccgccaa cgtgcctggg gcgtgccttt gccaatcttc   360
tacgctgaag acggcaccgc catcgtgacg catgaaacca tcgaacacgt ggctgacctc   420
```

| | |
|---|---:|
| tttgccaagg aaggctccaa cgcctggttc acccacccgg ttgaagaact tttgccagaa | 480 |
| ggctttactt cagaac | 496 |

<210> SEQ ID NO 17
<211> LENGTH: 496
<212> TYPE: DNA
<213> ORGANISM: Lactobacillus delbrueckii

<400> SEQUENCE: 17

| | |
|---|---:|
| atggacaaca aaggctgctt cactgaagaa atccctgacc cggacctggt gggcaagttc | 60 |
| tacgctgaca ccaacgaaat cgtcaaggac aagctggcgg ctgccggcaa ccttttgcac | 120 |
| tacagcacct ttgtccactc cgccgctcac gactggcgga ccaagaagcc ggtagtctac | 180 |
| cgggcaacca cgcaatggtt tgcctcaatc tccaagttca gagaccagat cctggaccag | 240 |
| attgaaaagg ccaccttcta cccggcctgg ggcaagaccc gcctttacaa catgatcaag | 300 |
| gaccggggcg attgggtaat ttcccgccaa cgtgcctggg gcgtgccttt gccaatcttc | 360 |
| tacgctgaag acggcaccgc catcgtgacg catgaaacca tcgaacacgt ggctgacctc | 420 |
| tttgccaagg aaggctccaa cgcctggttc acccacccgg ttgaagaact tttgccagaa | 480 |
| ggctttactt cagaac | 496 |

<210> SEQ ID NO 18
<211> LENGTH: 496
<212> TYPE: DNA
<213> ORGANISM: Lactobacillus delbrueckii

<400> SEQUENCE: 18

| | |
|---|---:|
| atggacaaca agggctgctt cactgaagaa atccctgacc cggacctggt gggcaagttc | 60 |
| tacgctgaca ccaacgaaat cgtcaaggac aagctggcgg ctgccggcaa ccttttgcac | 120 |
| tacagcacct ttgtccactc cgccgctcac gactggcgga ccaagaagcc ggtagtctac | 180 |
| cgggcaacca cgcaatggtt tgcctcaatc tccaagttca gagaccagat cctggaccag | 240 |
| attgaaaaga ccaccttcta cccggcctgg ggcaagaccc gcctttacaa catgatcaag | 300 |
| gaccggggcg attgggtaat ttcccgccaa cgtgcctggg gcgtgccttt gccaatcttc | 360 |
| tacgctgaag acggcaccgc catcgtgaca catgaaacca tcgaacacgt ggctgacctc | 420 |
| tttgccaagg aaggctccaa cgcctggttc acccacccgg ttgaagaact tttgccagaa | 480 |
| ggctttactt cagaac | 496 |

<210> SEQ ID NO 19
<211> LENGTH: 392
<212> TYPE: DNA
<213> ORGANISM: Lactobacillus delbrueckii

<400> SEQUENCE: 19

| | |
|---|---:|
| tcgggatcca gccaaacatg ctggttcttc gctcagaaat gccagttccg caggaaatga | 60 |
| aggacaagat ctccactttc accgacgttc agtcgactac catcgtggaa tctttggacg | 120 |
| cgccatctct gttgtgacgtg ccgttgtcct accaggaaca aggcgttgac cagaaggtcg | 180 |
| ttgacttcct ccacatcgac agcccgaagc cggttgccga catggacgaa tggcgccgga | 240 |
| tggacgaacg ggccaagaac ttgaagtaca agaccaagat caccctggtc ggcaagtacg | 300 |
| tcgaactgga agatgcctac atttccgtaa ctgacgcttt gcagcacgcc ggctacctgt | 360 |
| acaacagcga gatcgaagtt gaaaagatcc ag | 392 |

<210> SEQ ID NO 20
<211> LENGTH: 392
<212> TYPE: DNA
<213> ORGANISM: Lactobacillus delbrueckii

<400> SEQUENCE: 20

```
tgggtatcca gccaaacatg ctggttcttc gctcagaaat gccagttccg caggaaatga    60
aggacaagat ctccacttc accgacgttc cagtcgacta catcgtggaa tctttggacg   120
cgccatctct gtttgacgtg ccgttgtcct accaggaaca aggcgttgac cagaaggtcg   180
ttgacttcct ccacatcgac agcccgaagc cggttgccga catggacgaa tggcgccgga   240
tggacgaacg ggccaagaac ttgaagtaca agaccaagat caccctggtc ggcaagtacg   300
tcgaactgga agatgcctac atttccgtaa ctgacgcttt gcagcacgcc ggctacctgt   360
acaacagcga gatcgaagtt gaaaagatcc ag                                 392
```

<210> SEQ ID NO 21
<211> LENGTH: 412
<212> TYPE: DNA
<213> ORGANISM: Lactobacillus delbrueckii

<400> SEQUENCE: 21

```
cgtggaaatc tacgggccgg aatcttccgg taagacgacc gtcgccctgc acgccgtagc    60
tgaagtgcag aagcggggcg gcacggcggc ctacatcgac gcggaaaacg ccatggaccc   120
ggcttacgct gaagccttgg gcgtggacat cgaccaattg atcctgtctc agccaaacac   180
tggggaagaa ggactgcaaa tcgcggacac cttgatctcc agcggggcca tcgacatcgt   240
cgtggtcgac tccgttgccg ccctggtgcc gcgggccgaa atcgaaggtg aaatgggtga   300
ctcccacgtc ggtctccagg cccgcctgat gagccaggcc ttgcgcaagc tgtccgggac   360
gattgccaag accaagacca ttgccatctt catcaaccag atccgggaaa ag          412
```

<210> SEQ ID NO 22
<211> LENGTH: 412
<212> TYPE: DNA
<213> ORGANISM: Lactobacillus delbrueckii

<400> SEQUENCE: 22

```
cgtggaaatc tacgggccgg aatcttccgg taagacgacc gttgccctgc acgccgtagc    60
tgaagtgcag aagcggggcg gcacggcggc ctacatcgac gcggaaaacg ccatggaccc   120
ggcttacgct gaagccttgg gcgtggacat cgaccaattg atcctgtctc agccaaacac   180
tggggaagaa gggctgcaaa tcgcggacac cttgatctcc agcggggcca tcgacatcgt   240
cgtggtcgac tccgttgccg ccctggtgcc gcgggccgaa atcgaaggtg aaatgggtga   300
ctcccacgtt ggtctccagg cccgcctgat gagccaggcc ttgcgcaagc tctccgggac   360
gattgccaag accaagacca ttgccatctt catcaaccag atccgggaaa ag          412
```

<210> SEQ ID NO 23
<211> LENGTH: 412
<212> TYPE: DNA
<213> ORGANISM: Lactobacillus delbrueckii

<400> SEQUENCE: 23

```
cgtggaaatc tacgggccgg aatcttccgg taagacgacc gttgccctgc acgccgtagc    60
tgaagtgcag aagcggggcg gcacggcggc ctacatcgac gcggaaaacg ccatggaccc   120
ggcttacgct gaagccttgg gcgtggacat cgaccaattg atcctgtctc agccaaacac   180
```

```
tggggaagaa gggctgcaaa tcgcggacac cttgatctcc agcggggcca tcgacatcgt    240
cgtggtcgac tccgttgccg ccctggtgcc gcgggccgaa atcgaaggtg aaatgggtga    300
ctcccacgtc ggtctccagg cccgcctgat gagccaggcc ttgcgcaagc tctccgggac    360
gattgccaag accaagacca ttgccatctt catcaaccag attcgggaaa ag           412
```

```
<210> SEQ ID NO 24
<211> LENGTH: 490
<212> TYPE: DNA
<213> ORGANISM: Lactobacillus delbrueckii

<400> SEQUENCE: 24
ccaaccagca ctatcacaaa atttccgcca tgctggaaga tttcggagtc cgggtagccc     60
tcttaacggg atcaactaaa accatggagc ggcgggaaat ctacaaggag ctggctgatg    120
gcagcatcaa tgtggtgatc ggcacccatg ccttgatcca agagcaagtg gcctttaaaa    180
agctgggcct ggttattatc gacgagcagc accgttttgg cgttgtccag cgcctggcct    240
tgatcaacaa gggggaccgg ccggatatcc tggccatgac ggcgaccccg attcctcgtt    300
cattggcctt gactgtttat ggcgacaccg ccttgtcaga aatcagacac ctgccagccg    360
gccgtaagcc gattaaatcc tactggaaga ccagcagcca gctagatgag gtgtattcat    420
tgatgcgcca gcaactggcg gaaggcttcc agatttatgc ggttacgccc ttgatcagtg    480
agtcggaaac                                                           490
```

```
<210> SEQ ID NO 25
<211> LENGTH: 490
<212> TYPE: DNA
<213> ORGANISM: Lactobacillus delbrueckii

<400> SEQUENCE: 25
ccaaccagca ctatcacaaa atttctgcca tgctggaaga tttcggcgtc cgggtggccc     60
tcttaacggg atcaactaaa accatggagc ggcgggaaat ctacaaggag ctggctgatg    120
gcagcatcaa tgtggtgatc ggcacccatg ccttgatcca agagcaagtg gcctttaaaa    180
agctgggcct ggttattatc gacgagcagc accgttttgg cgttgtccag cgcctggcct    240
tgatcaacaa gggggaccgg ccggatatcc tggccatgac ggcgaccccg attccccgtt    300
cattggcctt gactgtttat ggcgacaccg ccttgtcaga aatcagacac ctgccagccg    360
gccgtaagcc gattaaatcc tactggaaga ccagcagcca gctagatgag gtgtattcat    420
tgatgcgcca gcaactggcg gaaggcttcc agatttatgc ggttacgccc ttgatcagtg    480
agtcggaaac                                                           490
```

```
<210> SEQ ID NO 26
<211> LENGTH: 20
<212> TYPE: DNA
<213> ORGANISM: Artificial Sequence
<220> FEATURE:
<223> OTHER INFORMATION: Forward primer for prtS gene

<400> SEQUENCE: 26
gacttgaaga aacagcgcgt                                                 20
```

```
<210> SEQ ID NO 27
<211> LENGTH: 20
<212> TYPE: DNA
<213> ORGANISM: Artificial Sequence
<220> FEATURE:
```

```
<223> OTHER INFORMATION: Reverse primer for prtS gene

<400> SEQUENCE: 27
taggtggagg cgttacagtg                                       20

<210> SEQ ID NO 28
<211> LENGTH: 20
<212> TYPE: DNA
<213> ORGANISM: Artificial Sequence
<220> FEATURE:
<223> OTHER INFORMATION: Forward primer for fusA gene

<400> SEQUENCE: 28
tgcgtgtcct tgacggtgcc                                       20

<210> SEQ ID NO 29
<211> LENGTH: 20
<212> TYPE: DNA
<213> ORGANISM: Artificial Sequence
<220> FEATURE:
<223> OTHER INFORMATION: Reverse primer for fusA gene

<400> SEQUENCE: 29
tgccttcctt gtcgtgggcg                                       20

<210> SEQ ID NO 30
<211> LENGTH: 20
<212> TYPE: DNA
<213> ORGANISM: Artificial Sequence
<220> FEATURE:
<223> OTHER INFORMATION: Forward primer for gyrB gene

<400> SEQUENCE: 30
aagctgggca actccgacgc                                       20

<210> SEQ ID NO 31
<211> LENGTH: 20
<212> TYPE: DNA
<213> ORGANISM: Artificial Sequence
<220> FEATURE:
<223> OTHER INFORMATION: Reverse primer for gyrB gene

<400> SEQUENCE: 31
catcggccgc atgtagcggt                                       20

<210> SEQ ID NO 32
<211> LENGTH: 22
<212> TYPE: DNA
<213> ORGANISM: Artificial Sequence
<220> FEATURE:
<223> OTHER INFORMATION: Forward primer for hsp60 gene

<400> SEQUENCE: 32
actgttttga cccaggccat cg                                    22

<210> SEQ ID NO 33
<211> LENGTH: 20
<212> TYPE: DNA
<213> ORGANISM: Artificial Sequence
<220> FEATURE:
<223> OTHER INFORMATION: Reverse primer for hsp60 gene

<400> SEQUENCE: 33
aacagcaacm acgttgaagg                                       20
```

```
<210> SEQ ID NO 34
<211> LENGTH: 20
<212> TYPE: DNA
<213> ORGANISM: Artificial Sequence
<220> FEATURE:
<223> OTHER INFORMATION: Forward primer for ileS gene

<400> SEQUENCE: 34
gcctggtcca caccgcttcc                                              20

<210> SEQ ID NO 35
<211> LENGTH: 20
<212> TYPE: DNA
<213> ORGANISM: Artificial Sequence
<220> FEATURE:
<223> OTHER INFORMATION: Reverse primer for ileS gene

<400> SEQUENCE: 35
accccgctcc aggatgaccc                                              20

<210> SEQ ID NO 36
<211> LENGTH: 20
<212> TYPE: DNA
<213> ORGANISM: Artificial Sequence
<220> FEATURE:
<223> OTHER INFORMATION: Forward primer for pyrG gene

<400> SEQUENCE: 36
tgcgggcagc caaggaactg                                              20

<210> SEQ ID NO 37
<211> LENGTH: 20
<212> TYPE: DNA
<213> ORGANISM: Artificial Sequence
<220> FEATURE:
<223> OTHER INFORMATION: Reverse primer for pyrG gene

<400> SEQUENCE: 37
ccgaaaccgc ctggcacgat                                              20

<210> SEQ ID NO 38
<211> LENGTH: 20
<212> TYPE: DNA
<213> ORGANISM: Artificial Sequence
<220> FEATURE:
<223> OTHER INFORMATION: Forward primer for recA gene

<400> SEQUENCE: 38
ctcactggca ctggacgcgg                                              20

<210> SEQ ID NO 39
<211> LENGTH: 20
<212> TYPE: DNA
<213> ORGANISM: Artificial Sequence
<220> FEATURE:
<223> OTHER INFORMATION: Reverse primer for recA gene

<400> SEQUENCE: 39
cttcagggcc cgaccacctg                                              20

<210> SEQ ID NO 40
<211> LENGTH: 20
<212> TYPE: DNA
<213> ORGANISM: Artificial Sequence
<220> FEATURE:
<223> OTHER INFORMATION: Forward primer for recG gene
```

```
<400> SEQUENCE: 40
ggaaattcgc cggccagcct                                                      20

<210> SEQ ID NO 41
<211> LENGTH: 20
<212> TYPE: DNA
<213> ORGANISM: Artificial Sequence
<220> FEATURE:
<223> OTHER INFORMATION: Reverse primer for recG gene

<400> SEQUENCE: 41
tgaccagcag atgcagcgcc                                                      20

<210> SEQ ID NO 42
<211> LENGTH: 511
<212> TYPE: DNA
<213> ORGANISM: Lactobacillus delbrueckii

<400> SEQUENCE: 42
gccatcgtgc aagaagggat gaagaacgtg gttgccgggg ctaacccagt tggcattcgc          60
cgcgggattg aaaaggccac ccaagcagcc gttgaccaat tgcacaagaa cagccacaaa         120
gtttccagcc gggaccaaat tgcccaagtt gcttcaatct caagtgcttc aaaggaaatc         180
ggcgacttga tcgctgaagc catggaaaag gtcggcaagg acggtgttat caccattgaa         240
gactcccgcg ggatcgaaac tgaactgagc gtggttgaag ggatgcaatt cgaccgcggc         300
tacctgtccc aatacatggt aacggacaac gacaagatgg aagctgactt ggaaaaccca         360
tacatcttga tcactgacaa gaagatttcc aacatccagg acattttgcc aatgttgcag         420
gaaatcgtga aagaaggccg ctcactccta atcatcgctg atgacgtgac tggtgaagct         480
ttgccaactc ttgttttgaa caagatccgc g                                        511
```

METHOD FOR PRODUCING FERMENTED FOOD, FERMENTED FOOD, AND LACTIC ACID BACTERIA-CONTAINING COMPOSITION

BACKGROUND OF THE INVENTION

Field of the Invention

The present invention relates to a method for producing a fermented food, a fermented food, and a lactic acid bacteria-containing composition, and more particularly to a method for producing a fermented food, a lactic acid bacteria-containing composition used therein, and a fermented food obtained therefrom.

Related Background Art

Examples of the fermented food include fermented milk defined as the "products which are obtained by fermenting milk, or milk, etc. containing an equal or greater amount of milk solids-not-fat with lactic acid bacteria or yeast and then forming a paste or liquid, or the frozen product" in the Japanese "Ministerial Ordinance on Milk and Milk products Concerning Compositional Standards, etc." Representative examples of such fermented milk include yogurt such as set type yogurt (solid fermented milk), soft type yogurt (pasty fermented milk), and drink type yogurt (liquid fermented milk).

In the production of yogurt, for example, a *Lactobacillus* species and *Streptococcus thermophilus* are used as lactic acid bacteria. In recent years, the mainstream yogurt has been prepared by fermenting raw material milk inoculated with a combination of *Lactobacillus delbrueckii* subsp. *bulgaricus* (*L. delbrueckii* subsp. *bulgaricus, L. bulgaricus*) and *Streptococcus thermophilus* (*S. thermophilus*). Such yogurt mainly has characteristics of a refreshing acidity and a fermented aroma.

For example, International Publication No. WO2018/151249 (Patent Document 1) describes a fermented milk production method comprising a step for adding lactic acid bacteria starter to a raw material mix to obtain a fermented milk base material; and a fermentation step for fermenting the fermented milk base material at 35 to 50° C., wherein the lactic acid bacteria starter includes *L. bulgaricus* and *S. thermophilus*. Moreover, International Application Japanese-Phase Publication No. 2015-518374 (Patent Document 2) describes the use of a certain *Streptococcus thermophilus* and *Lactobacillus delbrueckii* subsp. *bulgaricus* for the production of fermented milk products.

In addition, it is possible to prepare a fermented food even in the case of using bacteria whose species are same as *L. delbrueckii* subsp. *bulgaricus* but whose subspecies is different from *L. delbrueckii* subsp. *bulgaricus*. However, in the production of a fermented food, the use of bacteria whose species are same as *L. delbrueckii* subsp. *bulgaricus* but whose subspecies are different from *L. delbrueckii* subsp. *bulgaricus* makes it difficult to stably produce a fermented food as compared with the case of using *L. delbrueckii* subsp. *bulgaricus*, causing a problem that fermentation is impossible, a fermented food can be prepared but fermentation takes too long, or the flavor is not good depending on the bacterial species used (different subspecies).

SUMMARY OF THE INVENTION

In addition, the present inventors have examined a method for producing a fermented food using a *Lactobacillus* species and *Streptococcus thermophilus*, and have found a problem that prtS (−) *S. thermophilus* carrying no prtS gene, which have been conventionally used for the production of fermented milk (mainly yogurt), cannot be fermented or take too much time for fermentation when used in combination with a *Lactobacillus delbrueckii* species which cannot utilize lactose as an energy source, that is, which has no lactose utilization.

In addition, conventionally, yogurt having a refreshing acidity and fermented aroma as described above was the mainstream. However, in recent years, demands for a balanced and mild flavor in all of acidity, umami, fermented aroma, and richness have been increasing due to diversification of consumer preferences and yogurt eating methods.

The present invention aims to provide a method for producing a fermented food using a *Lactobacillus* species and *Streptococcus thermophilus*, a lactic acid bacterium and a lactic acid bacteria-containing composition which can be used therein, and a fermented food obtained therefrom. The method for producing a fermented food makes it possible to produce a fermented food even when using *Lactobacillus delbrueckii* which has no lactose utilization and to obtain a fermented food having a balanced and mild flavor in all of acidity, umami, fermented aroma, and richness.

The present inventors have made earnest studies to achieve the above object, and have found as a result that, among *Streptococcus thermophilus*, many strains derived from Japanese raw milk carry the prtS gene. *Streptococcus thermophilus* carrying the prtS gene can be fermented in the case of a single strain, and moreover, when this is used in combination with *Lactobacillus delbrueckii* for fermentation of raw material milk, the time required for fermentation can be significantly reduced. Furthermore, the present inventors have found that, with *Streptococcus thermophilus* carrying the prtS gene, a fermented food can be prepared in a short time even when the *Lactobacillus delbrueckii* has no lactose utilization.

What is more, the present inventors have found that it is possible to stably obtain a fermented food having a balanced and mild flavor particularly in all of acidity, umami, fermented aroma, and richness when the *Streptococcus thermophilus* carrying the prtS gene is combined with a specific *Lactobacillus delbrueckii* classified into a cluster different from the conventional *Lactobacillus delbrueckii* by multilocus sequence analysis (MLSA) classification. Thus, the present invention has been completed.

Specifically, the present invention provides the following.

[1] A method for producing a fermented food, comprising: a fermentation step of fermenting a raw material milk-containing milk preparation solution added with *Lactobacillus delbrueckii* and *Streptococcus thermophilus* carrying a prtS gene.

[2] The method for producing a fermented food according to [1], wherein the *Lactobacillus delbrueckii* is *Lactobacillus delbrueckii* classified into any one of clusters I, II, III, and V by MLSA classification based on seven housekeeping genes consisting of fusA gene, gyrB gene, hsp60 gene, ileS gene, pyrG gene, recA gene, and recG gene.

[3] The method for producing a fermented food according to [1] or [2], wherein the *Lactobacillus delbrueckii* is at least one selected from the group consisting of *Lactobacillus delbrueckii* satisfying all of the following conditions (i) to (vii):

(i) carrying an fusA gene whose allele number is 2 or 14,
(ii) carrying a gyrB gene whose allele number is any one selected from 3, 17, 18, and 25, (iii) carrying an hsp60 gene whose allele number is any one selected from 4, 18, 26, and 27,
(iv) carrying an ileS gene whose allele number is any one selected from 16, 20, 21, 30, and 33,
(v) carrying a pyrG gene whose allele number is 22 or 23,
(vi) carrying an recA gene whose allele number is any one selected from 2, 7, 24, and 28, and
(vii) carrying an recG gene whose allele number is 3, and *Lactobacillus delbrueckii* classified into the same cluster as that of the *Lactobacillus delbrueckii* satisfying all of the conditions (i) to (vii) by MLSA classification based on seven housekeeping genes consisting of fusA gene, gyrB gene, hsp60 gene, ileS gene, pyrG gene, recA gene, and recG gene.

[4] The method for producing a fermented food according to any one of [1] to [3], wherein the *Lactobacillus delbrueckii* is at least one selected from the group consisting of *Lactobacillus delbrueckii* specified by accession number NITE BP-02874, and *Lactobacillus delbrueckii* classified into the same cluster as that of the *Lactobacillus delbrueckii* specified by accession number NITE BP-02874 by MLSA classification based on seven housekeeping genes consisting of fusA gene, gyrB gene, hsp60 gene, ileS gene, pyrG gene, recA gene, and recG gene.

[5] The method for producing a fermented food according to any one of [1] to [4], wherein the *Lactobacillus delbrueckii* is *Lactobacillus delbrueckii* specified by accession number NITE BP-02874.

[6] The method for producing a fermented food according to [1] or [2], wherein the *Lactobacillus delbrueckii* is *Lactobacillus delbrueckii* which has no lactose utilization.

[7] The method for producing a fermented food according to any one of [1] to [6], wherein the *Streptococcus thermophilus* carrying the prtS gene is *Streptococcus thermophilus* specified by accession number NITE BP-02875.

[8] A fermented food comprising *Lactobacillus delbrueckii* and *Streptococcus thermophilus* carrying a prtS gene.

[9] The fermented food according to [8], wherein the *Lactobacillus delbrueckii* is *Lactobacillus delbrueckii* classified into any one of clusters I, II, III, and V by MLSA classification based on seven housekeeping genes consisting of fusA gene, gyrB gene, hsp60 gene, ileS gene, pyrG gene, recA gene, and recG gene.

[10] The fermented food according to [8] or [9], wherein the *Lactobacillus delbrueckii* is at least one selected from the group consisting of *Lactobacillus delbrueckii* satisfying all of the following conditions (i) to (vii):
(i) carrying an fusA gene whose allele number is 2 or 14,
(ii) carrying a gyrB gene whose allele number is any one selected from 3, 17, 18, and 25,
(iii) carrying an hsp60 gene whose allele number is any one selected from 4, 18, 26, and 27,
(iv) carrying an ileS gene whose allele number is any one selected from 16, 20, 21, 30, and 33,
(v) carrying a pyrG gene whose allele number is 22 or 23,
(vi) carrying an recA gene whose allele number is any one selected from 2, 7, 24, and 28, and
(vii) carrying an recG gene whose allele number is 3, and *Lactobacillus delbrueckii* classified into the same cluster as that of the *Lactobacillus delbrueckii* satisfying all of the conditions (i) to (vii) by MLSA classification based on seven housekeeping genes consisting of fusA gene, gyrB gene, hsp60 gene, ileS gene, pyrG gene, recA gene, and recG gene.

[11] The fermented food according to anyone of [8] to [10], wherein the *Lactobacillus delbrueckii* is at least one selected from the group consisting of *Lactobacillus delbrueckii* specified by accession number NITE BP-02874, and *Lactobacillus delbrueckii* classified into the same cluster as that of the *Lactobacillus delbrueckii* specified by accession number NITE BP-02874 by MLSA classification based on seven housekeeping genes consisting of fusA gene, gyrB gene, hsp60 gene, ileS gene, pyrG gene, recA gene, and recG gene.

[12] The fermented food according to any one of [8] to [11], wherein the *Lactobacillus delbrueckii* is *Lactobacillus delbrueckii* specified by accession number NITE BP-02874.

[13] The fermented food according to [8] or [9], wherein the *Lactobacillus delbrueckii* is *Lactobacillus delbrueckii* which has no lactose utilization.

[14] The fermented food according to anyone of [8] to [13], wherein the *Streptococcus thermophilus* carrying the prtS gene is *Streptococcus thermophilus* specified by accession number NITE BP-02875.

[15] *Streptococcus thermophilus* specified by accession number NITE BP-02875.

[16] The *Streptococcus thermophilus* specified by accession number NITE BP-02875 according to [15], which is the *Streptococcus thermophilus* carrying the prtS gene and used in the method for producing a fermented food according to any one of [1] to [7].

[17] At least one *Lactobacillus delbrueckii* selected from the group consisting of *Lactobacillus delbrueckii* satisfying all of the following conditions (i) to (vii):
(i) carrying an fusA gene whose allele number is 2 or 14,
(ii) carrying a gyrB gene whose allele number is any one selected from 3, 17, 18, and 25,
(iii) carrying an hsp60 gene whose allele number is any one selected from 4, 18, 26, and 27,
(iv) carrying an ileS gene whose allele number is any one selected from 16, 20, 21, 30, and 33,
(v) carrying a pyrG gene whose allele number is 22 or 23,
(vi) carrying an recA gene whose allele number is any one selected from 2, 7, 24, and 28, and
(vii) carrying an recG gene whose allele number is 3, and *Lactobacillus delbrueckii* classified into the same cluster as that of the *Lactobacillus delbrueckii* satisfying all of the conditions (i) to (vii) by MLSA classification based on seven housekeeping genes consisting of fusA gene, gyrB gene, hsp60 gene, ileS gene, pyrG gene, recA gene, and recG gene.

[18] The *Lactobacillus delbrueckii* according to [17], which is at least one selected from the group consisting of *Lactobacillus delbrueckii* specified by accession number NITE BP-02874, and *Lactobacillus delbrueckii* classified into the same cluster as that of the *Lactobacillus delbrueckii* specified by accession number NITE BP-02874 by MLSA classification based on seven housekeeping genes consisting of fusA gene, gyrB gene, hsp60 gene, ileS gene, pyrG gene, recA gene, and recG gene.

[19] The *Lactobacillus delbrueckii* according to [17] or [18], which is the *Lactobacillus delbrueckii* used in the method for producing a fermented food according to any one of [1] to [7].

[20] A lactic acid bacteria-containing composition used in the method for producing a fermented food according to any one of [1] to [7], comprising: *Lactobacillus delbrueckii* and/or *Streptococcus thermophilus* carrying a prtS gene.

[21] The lactic acid bacteria-containing composition according to [20], wherein the *Streptococcus thermophilus* is the *Streptococcus thermophilus* according to [15] or [16].

[22] The lactic acid bacteria-containing composition according to [20] or [21], wherein the *Lactobacillus delbrueckii* is the *Lactobacillus delbrueckii* according to any one of [17] to [19].

The present invention makes it possible to provide a method for producing a fermented food using a *Lactobacillus* species and *Streptococcus thermophilus*, a lactic acid bacterium and a lactic acid bacteria-containing composition which can be used therein, and a fermented food obtained therefrom. The method for producing a fermented food makes it possible to produce a fermented food even when using *Lactobacillus delbrueckii* which has no lactose utilization and to obtain a fermented food having a balanced and mild flavor in all of acidity, umami, fermented aroma, and richness.

BRIEF DESCRIPTION OF THE DRAWINGS

FIG. 2A is a diagram illustrating the allele number of the fusA gene and its base sequence (bases 1 to 200);

FIG. 2B is a diagram illustrating the allele number of the fusA gene and its base sequence (bases 201 to 400);

FIG. 2C is a diagram illustrating the allele number of the fusA gene and its base sequence (bases 401 to 474);

FIG. 3A is a diagram illustrating the allele number of the gyrB gene and its base sequence (bases 1 to 100);

FIG. 3B is a diagram illustrating the allele number of the gyrB gene and its base sequence (bases 101 to 200);

FIG. 3C is a diagram illustrating the allele number of the gyrB gene and its base sequence (bases 201 to 300);

FIG. 3D is a diagram illustrating the allele number of the gyrB gene and its base sequence (bases 301 to 380);

FIG. 4A is a diagram illustrating the allele number of the hsp60 gene and its base sequence (bases 1 to 100);

FIG. 4B is a diagram illustrating the allele number of the hsp60 gene and its base sequence (bases 101 to 200);

FIG. 4C is a diagram illustrating the allele number of the hsp60 gene and its base sequence (bases 201 to 300);

FIG. 4D is a diagram illustrating the allele number of the hsp60 gene and its base sequence (bases 301 to 400);

FIG. 4E is a diagram illustrating the allele number of the hsp60 gene and its base sequence (bases 401 to 500);

FIG. 4F is a diagram illustrating the allele number of the hsp60 gene and its base sequence (bases 501 to 511);

FIG. 5A is a diagram illustrating the allele number of the ileS gene and its base sequence (bases 1 to 100);

FIG. 5B is a diagram illustrating the allele number of the ileS gene and its base sequence (bases 101 to 200);

FIG. 5C is a diagram illustrating the allele number of the ileS gene and its base sequence (bases 201 to 300);

FIG. 5D is a diagram illustrating the allele number of the ileS gene and its base sequence (bases 301 to 400);

FIG. 5E is a diagram illustrating the allele number of the ileS gene and its base sequence (bases 401 to 496);

FIG. 6B is a diagram illustrating the allele number of the pyrG gene and its base sequence (bases 101 to 200);

FIG. 6C is a diagram illustrating the allele number of the pyrG gene and its base sequence (bases 201 to 300);

FIG. 6D is a diagram illustrating the allele number of the pyrG gene and its base sequence (bases 301 to 392);

FIG. 7A is a diagram illustrating the allele number of the recA gene and its base sequence (bases 1 to 100);

FIG. 7B is a diagram illustrating the allele number of the recA gene and its base sequence (bases 101 to 200);

FIG. 7C is a diagram illustrating the allele number of the recA gene and its base sequence (bases 201 to 300);

FIG. 7D is a diagram illustrating the allele number of the recA gene and its base sequence (bases 301 to 400);

FIG. 7E is a diagram illustrating the allele number of the recA gene and its base sequence (bases 401 to 412);

FIG. 8A is a diagram illustrating the allele number of the recG gene and its base sequence (bases 1 to 100);

FIG. 8B is a diagram illustrating the allele number of the recG gene and its base sequence (bases 101 to 200);

FIG. 8C is a diagram illustrating the allele number of the recG gene and its base sequence (bases 201 to 300);

FIG. 8D is a diagram illustrating the allele number of the recG gene and its base sequence (bases 301 to 400);

FIG. 8E is a diagram illustrating the allele number of the recG gene and its base sequence (bases 401 to 490);

DETAILED DESCRIPTION OF THE PREFERRED EMBODIMENTS

Figure 1:
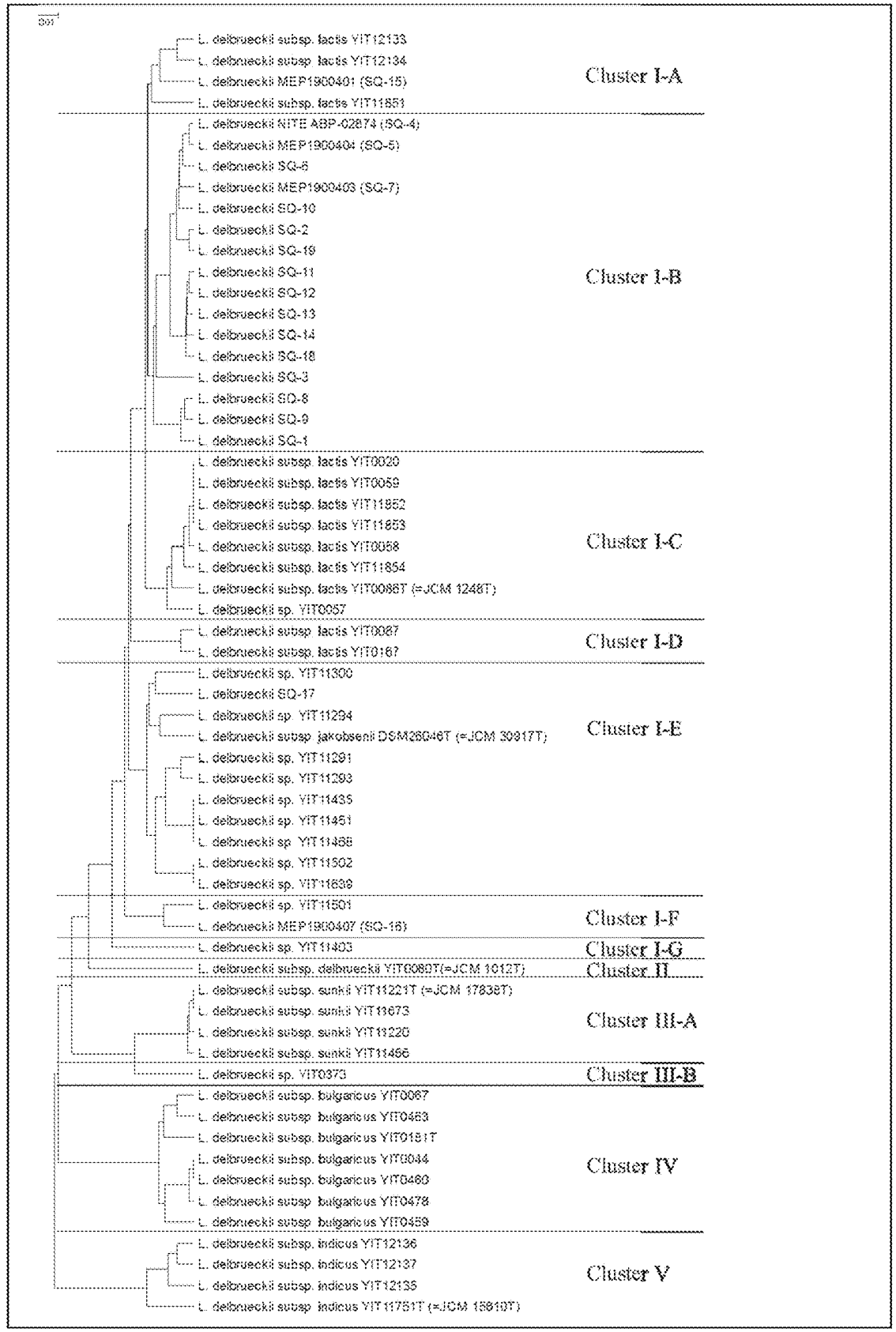
FIG. 1 is a diagram illustrating a phylogenetic tree obtained by performing MLSA classification on 61 strains of *Lactobacillus delbrueckii*.
Figure 6A:
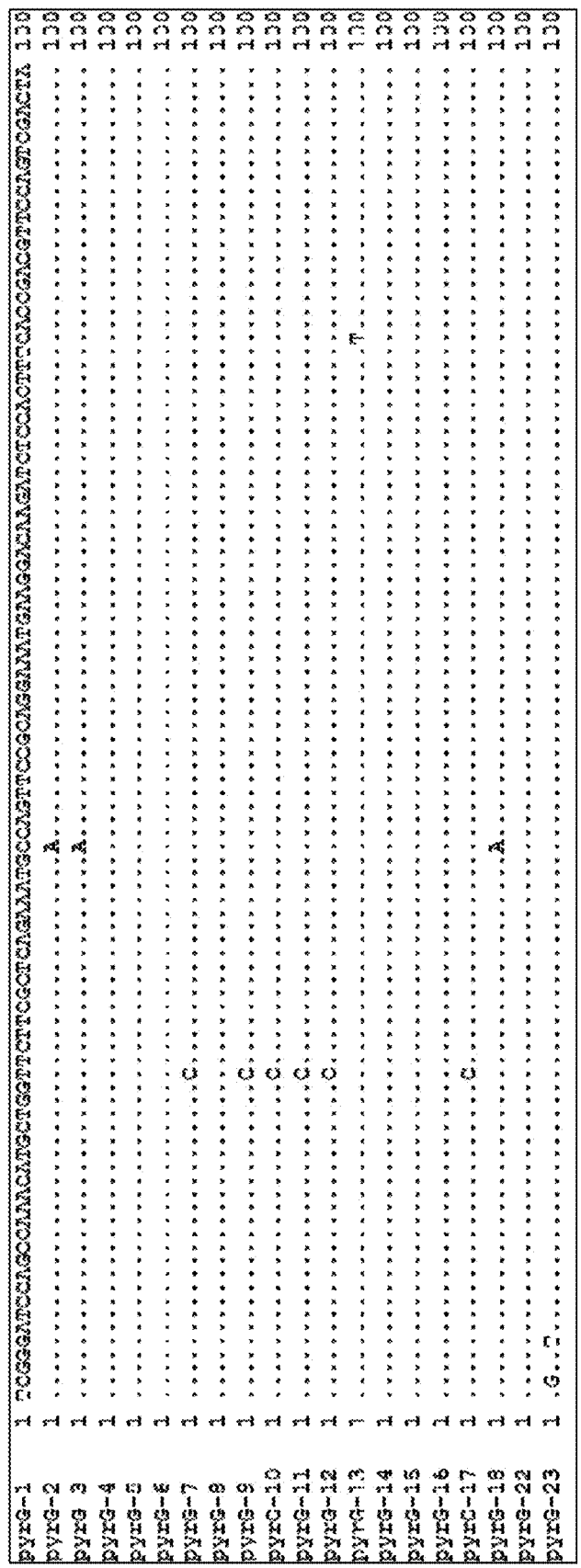
FIG. 6A is a diagram illustrating the allele number of the pyrG gene and its base sequence (bases 1 to 100)

Hereinafter, the present invention is described in detail with reference to preferred embodiments.

<Method for Producing Fermented Food>

The method for producing a fermented food of the present invention comprises a fermentation step of fermenting a raw material milk-containing milk preparation solution added with *Lactobacillus delbrueckii* and *Streptococcus thermophilus* carrying a prtS gene.

(Milk Preparation Solution)

The milk preparation solution according to the present invention contains raw material milk. Preferably, the raw material milk contains lactose, and examples thereof include raw milk (for example, milk of cows, buffaloes, sheep, goats, and the like), sterilized milk, full-fat milk, skim milk, whey, and processed products thereof (such as whole fat milk powder, whole fat concentrated milk, skimmed milk powder, defatted concentrated milk, condensed milk, whey powder, buttermilk, butter, cream, cheese, whey protein concentrate (WPC), whey protein isolate (WPI), α-lactalbumin (α-La), and β-lactoglobulin (β-Lg)). One of these or a mixture of two or more thereof may be used.

The milk preparation solution according to the present invention may be composed of only the raw material milk, may be an aqueous solution, diluent, or concentrated liquid of the raw material milk, or may further contain other components, if necessary, in addition to the raw material milk. Examples of the other components include water; soy milk, saccharides including sugar, sweeteners, flavors, fruit juices, fruit pulp, vitamins, minerals, oils and fats, ceramides, collagen, milk phospholipids, polyphenols, and other foods, food ingredients, and food additives; and stabilizers such as pectin, soybean polysaccharide, carboxy methylcellulose (CMC), agar, gelatin, carrageenan, and gums, thickeners, and gelling agents. One of these or a mixture of two or more thereof may be used. The milk preparation solution can be prepared by mixing the above components while heating as necessary and/or homogenizing as necessary. In addition, as the above-mentioned milk preparation solution, a solution sterilized by heating can be used.

(*Lactobacillus Delbrueckii*)

The method for producing a fermented food of the present invention ferments the above-described milk preparation solution added with a combination of *Lactobacillus delbrueckii* and *Streptococcus thermophilus* carrying the following prtS gene.

*Lactobacillus delbrueckii* (hereinafter sometimes referred to as "*L. delbrueckii*") is a bacterial species classified into the genus *Lactobacillus*. It is known that there are six subspecies of *Lactobacillus delbrueckii* subsp. *bulgaricus*, *Lactobacillus delbrueckii* subsp. *delbrueckii*, *Lactobacillus delbrueckii* subsp. *lactis*, *Lactobacillus delbrueckii* subsp. *indicus*, *Lactobacillus delbrueckii* subsp. *sunkii*, and *Lactobacillus delbrueckii* subsp. *jakobsenii* in the *Lactobacillus delbrueckii*.

In addition, *L. delbrueckii* includes *L. delbrueckii* which can catabolize lactose into glucose and galactose for utilize as an energy source, that is, which has lactose utilization (hereinafter sometimes referred to as "*L. delbrueckii* Lac(+)") and *L. delbrueckii* which cannot utilize lactose as an energy source, that is, which has no lactose utilization (hereinafter sometimes referred to as "*L. delbrueckii* Lac(−)"). Conventionally, it has been considered difficult to obtain a fermented food (especially fermented milk) having lactose as a main sugar source when using *L. delbrueckii* Lac(−). However, in the present invention, even with any of *L. delbrueckii* (even with *L. delbrueckii* Lac(−)), it is possible to stably obtain a fermented food in a short time by fermenting the milk preparation solution by combining with *Streptococcus thermophilus* carrying the following prtS gene.

In the present invention, the method for confirming whether or not *L. delbrueckii* has lactose utilization is not particularly limited. For example, even in the case of culture for 48 hours at a proper temperature and a proper pH in a medium containing lactose as a single sugar source, it can be confirmed by the fact that lactose in the medium cannot be catabolized into glucose and galactose, and that the pH of the medium is not changed by lactic acid.

The *L. delbrueckii* according to the present invention is not particularly limited and may be selected from those known as the above subspecies. Particularly from the viewpoint that a fermented food (especially fermented milk) having a balanced and mild flavor in all of acidity, umami, fermented aroma, and richness tends to be obtained, preferable is *Lactobacillus delbrueckii* classified into any one of clusters I, II, III, and V by MLSA classification based on seven housekeeping genes consisting of fusA gene, gyrB gene, hsp60 gene, ileS gene, pyrG gene, recA gene, and recG gene, and more preferable is at least one selected from the group consisting of *L. delbrueckii* satisfying all of the following conditions (i) to (vii):

(i) carrying an fusA gene whose allele number is 2 or 14,
(ii) carrying a gyrB gene whose allele number is any one selected from 3, 17, 18, and 25,
(iii) carrying an hsp60 gene whose allele number is any one selected from 4, 18, 26, and 27,
(iv) carrying an ileS gene whose allele number is any one selected from 16, 20, 21, 30, and 33,
(v) carrying a pyrG gene whose allele number is 22 or 23,
(vi) carrying an recA gene whose allele number is any one selected from 2, 7, 24, and 28, and
(vii) carrying an recG gene whose allele number is 3, and

*L. delbrueckii* classified into the same cluster as that of the *L. delbrueckii* satisfying all of the conditions (i) to (vii) by MLSA classification based on seven housekeeping genes consisting of fusA gene, gyrB gene, hsp60 gene, ileS gene, pyrG gene, recA gene, and recG gene.

In the present invention, the "fusA gene" refers to a gene encoding elongation factor EF-2 (protein elongation factor ES-2), the "gyrB gene" refers to a gene encoding DNA gyrase subunit B, the "hsp60 gene" refers to a gene encoding heat-shock protein 60, the "ileS gene" refers to a gene encoding isoleucyl-tRNA synthase, the "pyrG gene" refers to a gene encoding CTP synthase, the "recA gene" refers to a gene encoding recombinase A, and the "recG gene" refers to a gene encoding ATP-dependent DNA helicase. All of these seven genes are housekeeping genes that are essential for the maintenance and growth of *L. delbrueckii*.

The MLSA classification based on these seven housekeeping genes is a classification based on multilocus sequence analysis (MLSA), which is a technique including obtaining a sequence (concatenated sequence) obtained by concatenating the base sequences of the above housekeeping genes for each strain, constructing a phylogenetic tree using the obtained concatenated sequence, and classifying strains into clusters based on the obtained phylogenetic tree. In the present invention, MLSA classification is carried out on 59 strains of *L. delbrueckii* with strain Nos. 1 to 59 presented in Tables 1 and 2 below (more preferably 61 strains with strain Nos. 1 to 61 presented in Tables 1 and 2 below), or, when the target strain is not included in the 59 strains (or the 61 strains), MLSA classification is carried out on 60 strains (or 62 strains) including the 59 strains (or the 61 strains) plus 1 strain being the target. In this way, the cluster of each strain is determined.

In Tables 1 and 2 below, the strains with strain Nos. 1 to 41 are *L. delbrueckii* described in Tanigawa et al., Microbiology, 2011, 157, pp. 727-738 (hereinafter referred to as "Tanigawa et al."), and the strain with strain No. 42 is *L. delbrueckii* described in Adimpong D. B. et al., International Journal of Systematic and Evolutionally Microbiology, 2013, 63, pp. 3720-3726 (hereinafter referred to as "Adimpong D. B. et al."). In addition, the strains with strain Nos. 43 to 61 are 19 strains of *L. delbrueckii* among several species of lactic acid bacteria derived from raw milk, yogurt, Japanese traditional pickles "*sunki*", and the like.

The base sequence of each housekeeping gene was obtained from GeneBank/EMBL/DDBJ access numbers described in Tanigawa et al. for strain Nos. 1 to 41, and obtained from GeneBank/EMBL/DDBJ access number ALPY0000000 described in Adimpong D. B. et al. for strain No. 42. In addition, the base sequences for strain Nos. 43 to 61 were obtained as follows. In the method described in the Examples to be described later, the primers described later, prepared from the highly conserved sequences of the housekeeping genes, were used to obtain products by the PCR method, which were used to determine the base sequence of each gene. Among the obtained base sequences, a list of the sequence identification numbers of the base sequences newly obtained this time (base sequences not described in Tanigawa et al.; base sequences newly assigned the following allele numbers this time) is presented in Table 3 below together with allele numbers described later. The base sequences of the housekeeping genes of *L. delbrueckii* except for the 61 strains can be obtained by, for example, using the above-mentioned primers in the same manner as strain Nos. 43 to 61.

In the present invention, the concatenated sequence in each strain is obtained by concatenating the obtained base sequences for seven genes in the order of fusA gene, gyrB gene, hsp60 gene, ileS gene, pyrG gene, recA gene, and recG gene. As a method for constructing a phylogenetic tree using the above-mentioned concatenated sequence, a conventionally known method can be appropriately employed. For example, the phylogenetic tree can be constructed using software such as Genetyx v. 13 (manufactured by GENETYX CORPORATION), but it is preferable to use the unweighted pair group method with arithmetic mean (UPGMA). FIG. 1 illustrates a phylogenetic tree constructed by the unweighted pair group method with arithmetic mean with Genetyx v. 13 using the above concatenated sequence for *L. delbrueckii* with strain Nos. 1 to 61 described in Tables 1 and 2 below. In addition, Tables 1 and 2 below present clusters in each of which a strain is classified according to the phylogenetic tree obtained, together with allele numbers described later.

As presented in FIG. 1 and Tables 1 and 2 below, among clusters I classified by the phylogenetic tree obtained by the above method, subcluster I-B (cluster I-B) is a new cluster composed of novel *L. delbrueckii* without conventionally known *L. delbrueckii* (for example, *L. delbrueckii* with strain Nos. 1 to 42).

Particularly from the viewpoint that a fermented food (especially fermented milk) having a balanced and mild flavor in all of acidity, umami, fermented aroma, and richness tends to be obtained in combination with *Streptococcus thermophilus* carrying the following prtS gene, such *L. delbrueckii* is preferably *L. delbrueckii* classified into any one of clusters I, II, III, and V by the above MLSA classification,
more preferably at least one selected from the group consisting of *L. delbrueckii* satisfying all of the following conditions (i) to (vii):
(i) carrying an fusA gene whose allele number is 2 or 14,
(ii) carrying a gyrB gene whose allele number is any one selected from 3, 17, 18, and 25,
(iii) carrying an hsp60 gene whose allele number is any one selected from 4, 18, 26, and 27, (iv) carrying an ileS gene whose allele number is any one selected from 16, 20, 21, 30, and 33,
(v) carrying a pyrG gene whose allele number is 22 or 23,
(vi) carrying an recA gene whose allele number is any one selected from 2, 7, 24, and 28, and
(vii) carrying an recG gene whose allele number is 3, and *L. delbrueckii* classified into the same cluster (cluster I in FIG. 1) as that of the *L. delbrueckii* satisfying all of the conditions (i) to (vii) by the above MLSA classification, and further preferably at least one selected from the group consisting of the *L. delbrueckii* satisfying all of the conditions (i) to (vii) and the *L. delbrueckii* classified into the same subcluster (subcluster I-B in FIG. 1) as that of the *L. delbrueckii* satisfying all of the conditions (i) to (vii).

In the present invention, hereinafter, the "*L. delbrueckii* classified into anyone of clusters I, II, III, and V (hereinafter sometimes referred to as '*L. delbrueckii* (I, II, III, V)')" refers to, when the cluster into which *L. delbrueckii* satisfying all of the conditions (i) to (vii) is classified is defined as cluster I, any one of *L. delbrueckii* classified into clusters II, III, and V excluding cluster IV, and *L. delbrueckii* classified into cluster I among the four clusters (clusters II to V) classified in order by the unweighted pair group method with arithmetic mean. Clusters I to V may be further divided into subclusters (for example, in FIG. 1, cluster I is divided into subclusters I-A to I-G, and cluster III is divided into subclusters III-A and III-B).

Among these, particularly from the viewpoint that a fermented food (especially fermented milk) having a balanced and mild flavor in all of acidity, umami, fermented aroma, and richness tends to be obtained, the *L. delbrueckii* according to the present invention is preferably *L. delbrueckii* classified into cluster I, and particularly preferably *L. delbrueckii* classified into subcluster I-B (hereinafter sometimes referred to as "*L. delbrueckii* (I-B)").

Figure 2A:
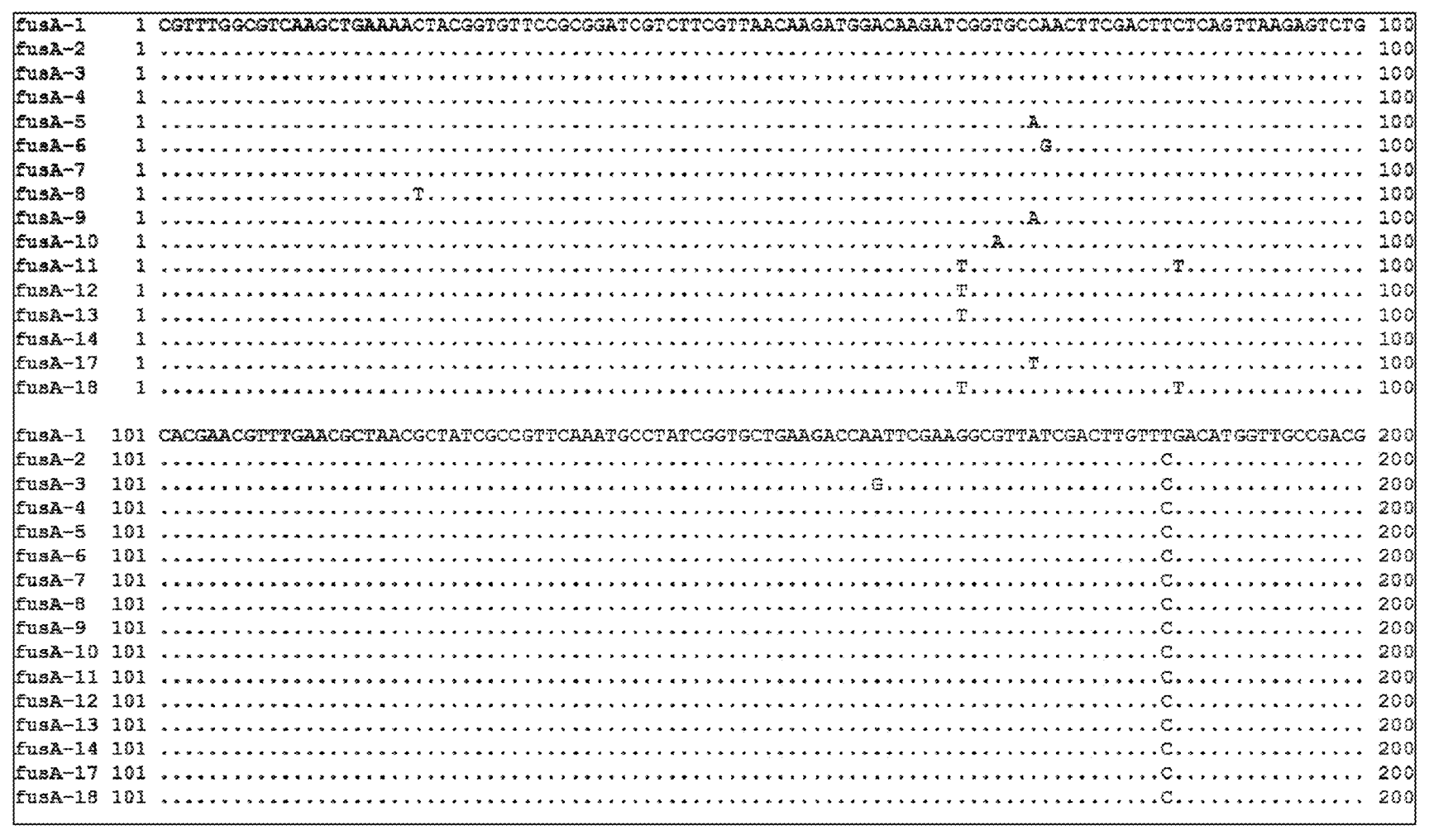
Figure 2B:
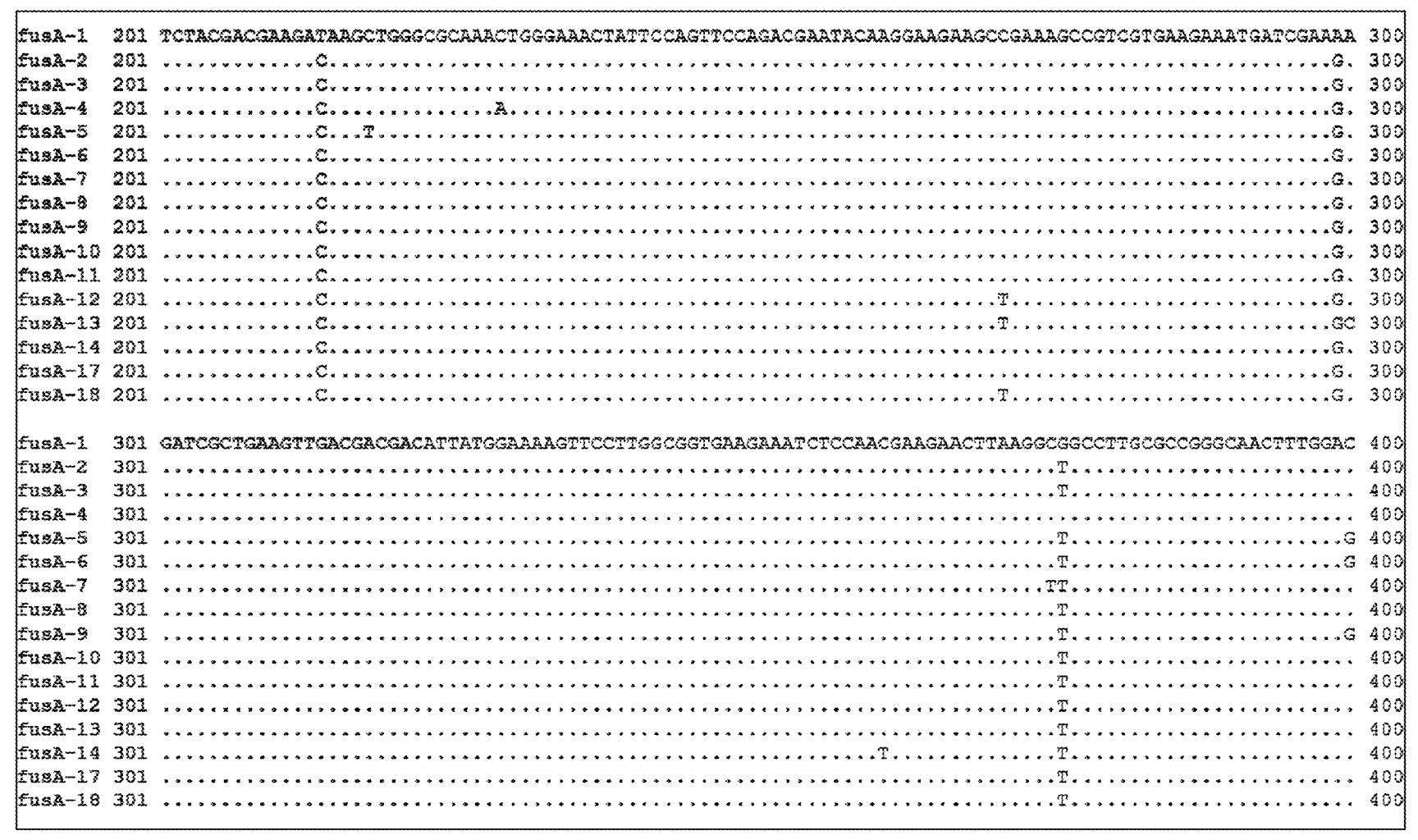
Figure 3A:
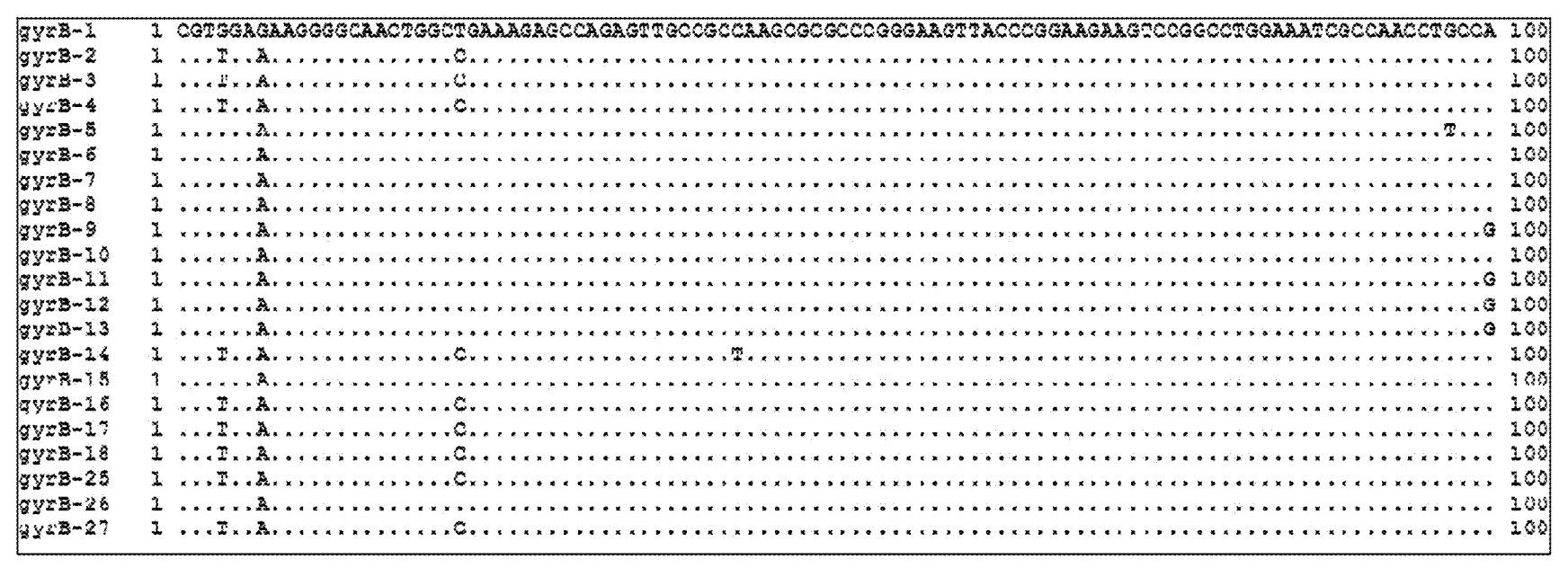
Figure 3B:
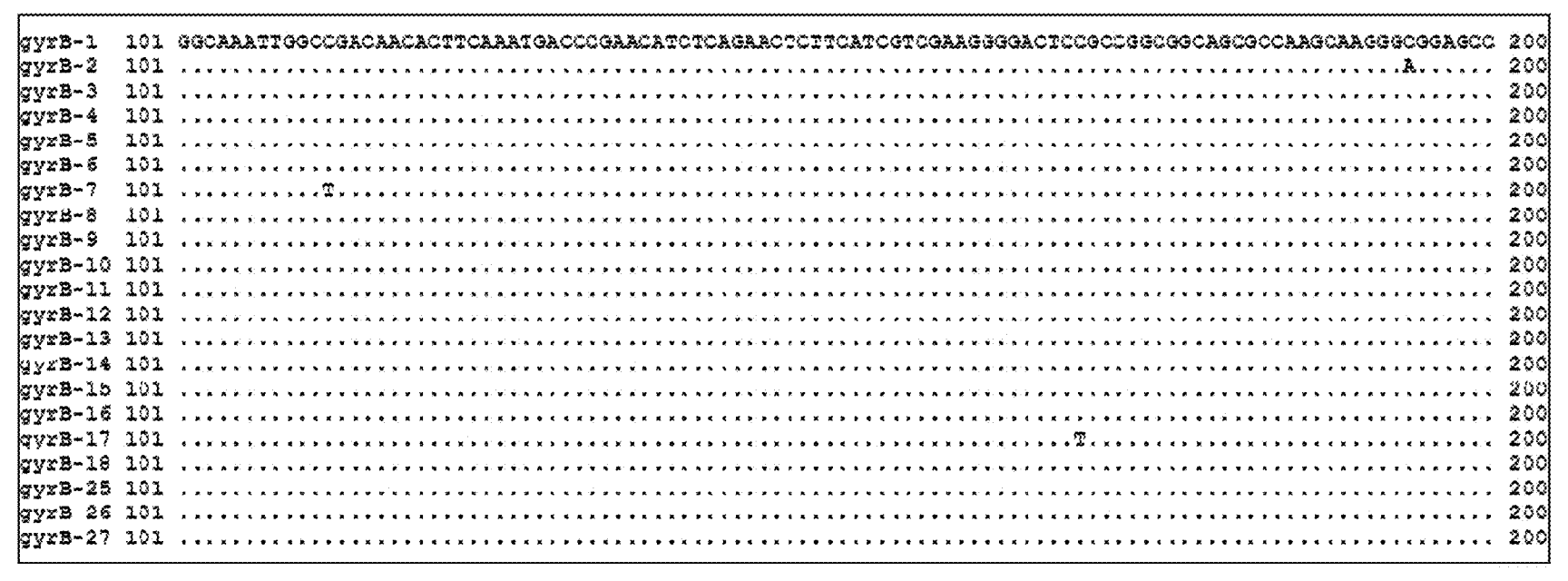
Figure 3C:
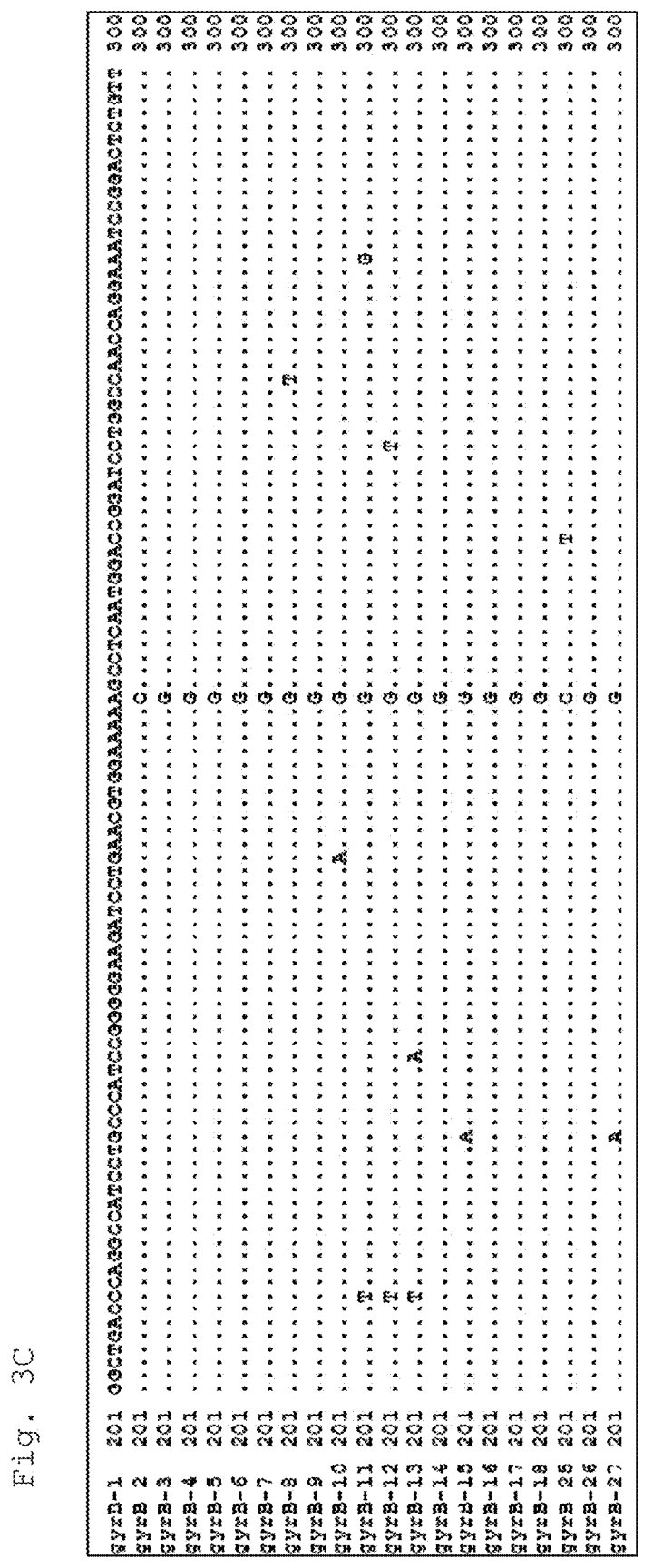
Figure 3D:
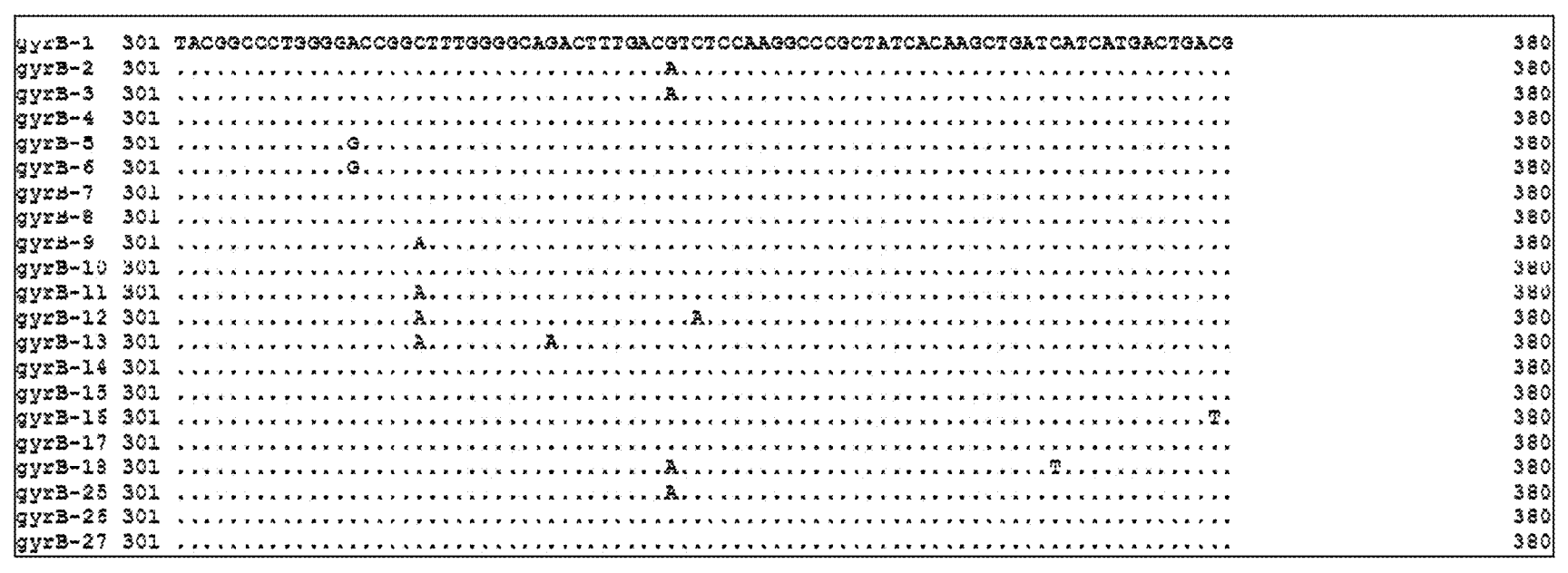
Figure 4D:
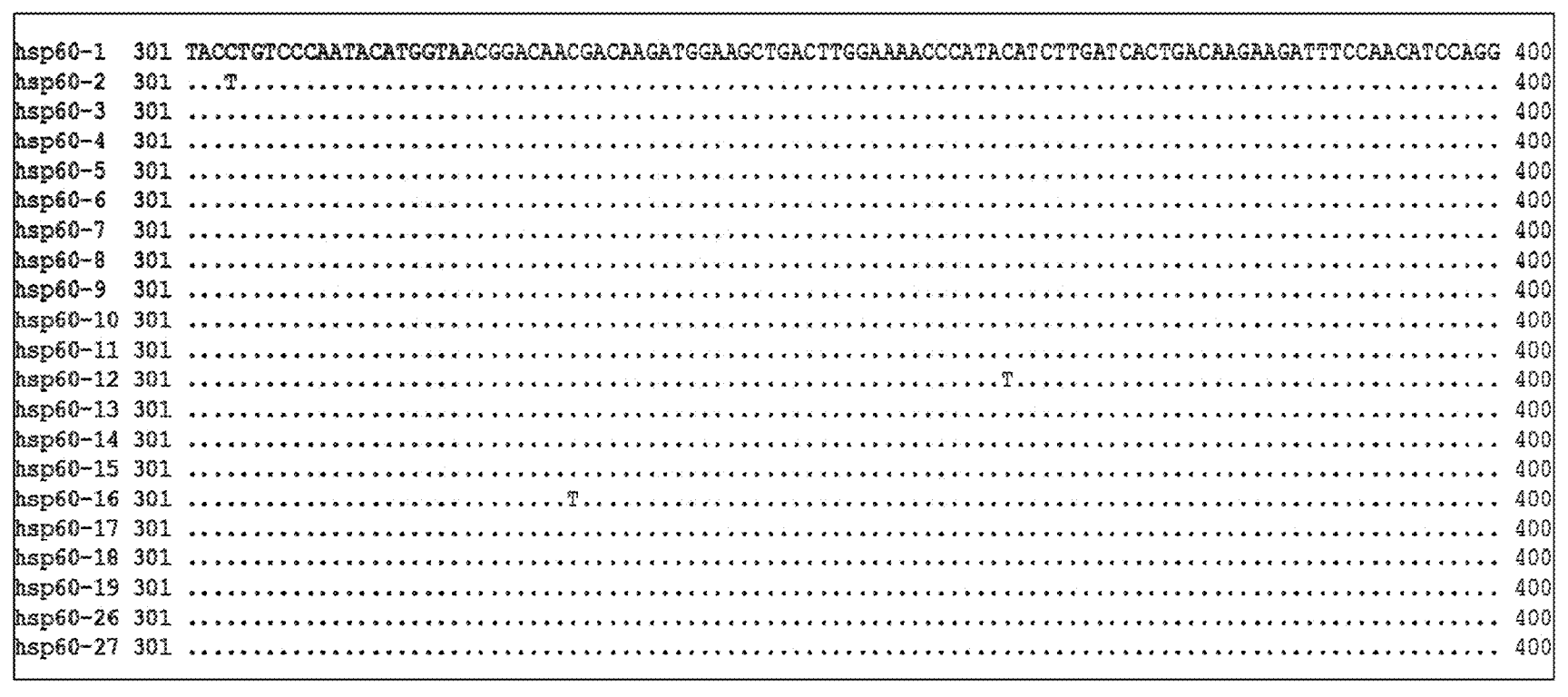
Figure 5A:
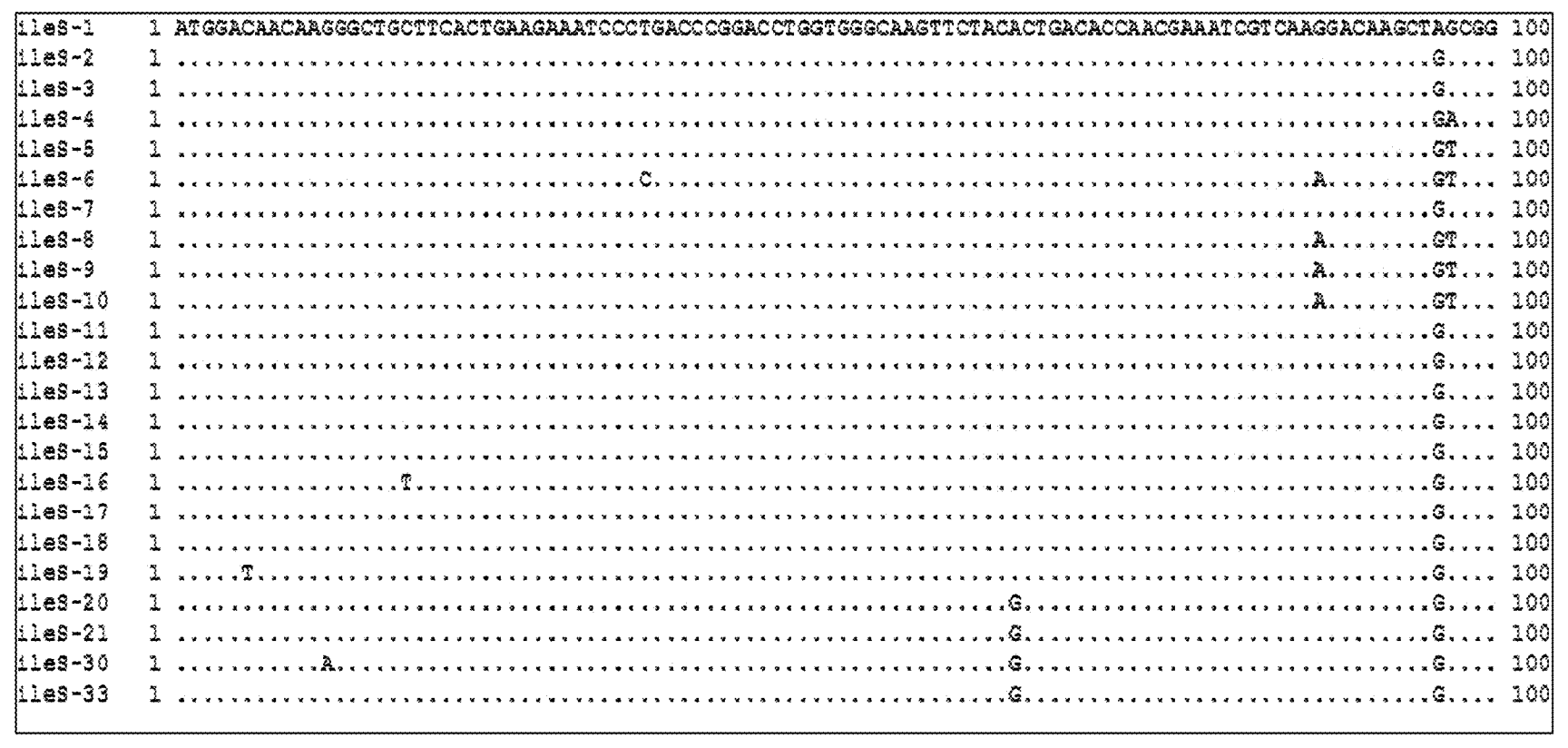
Figure 5B:
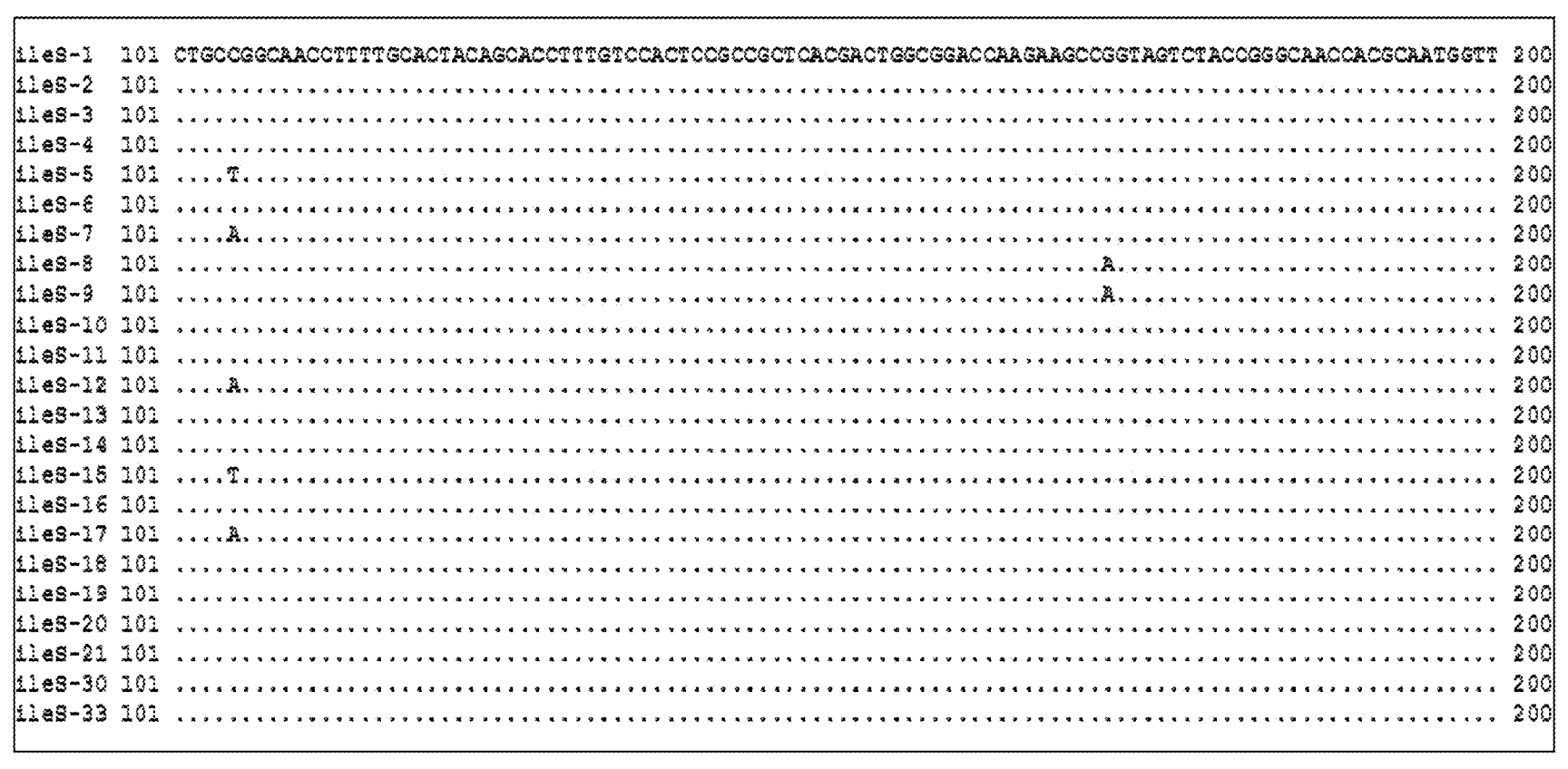
Figure 5C:
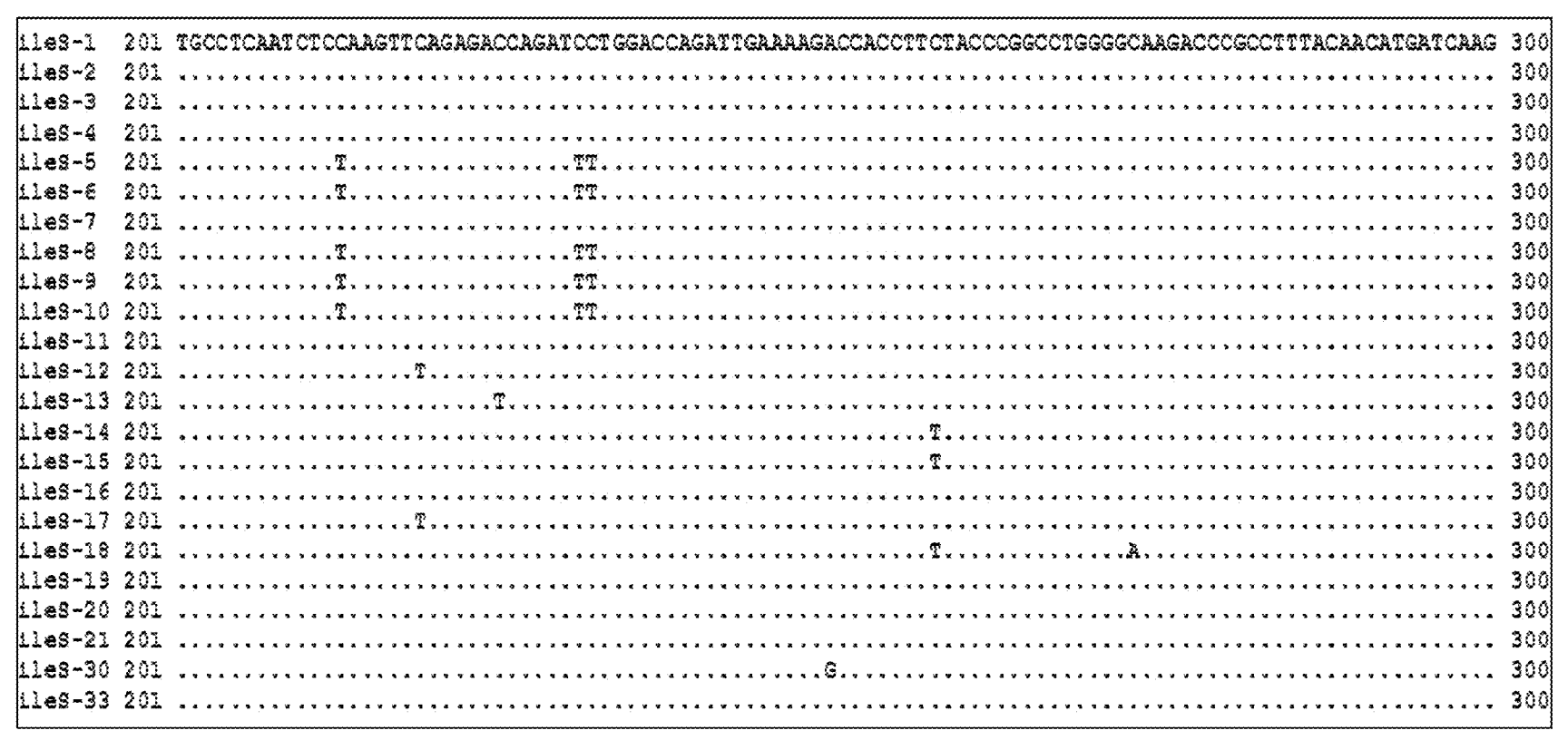
Figure 5D:
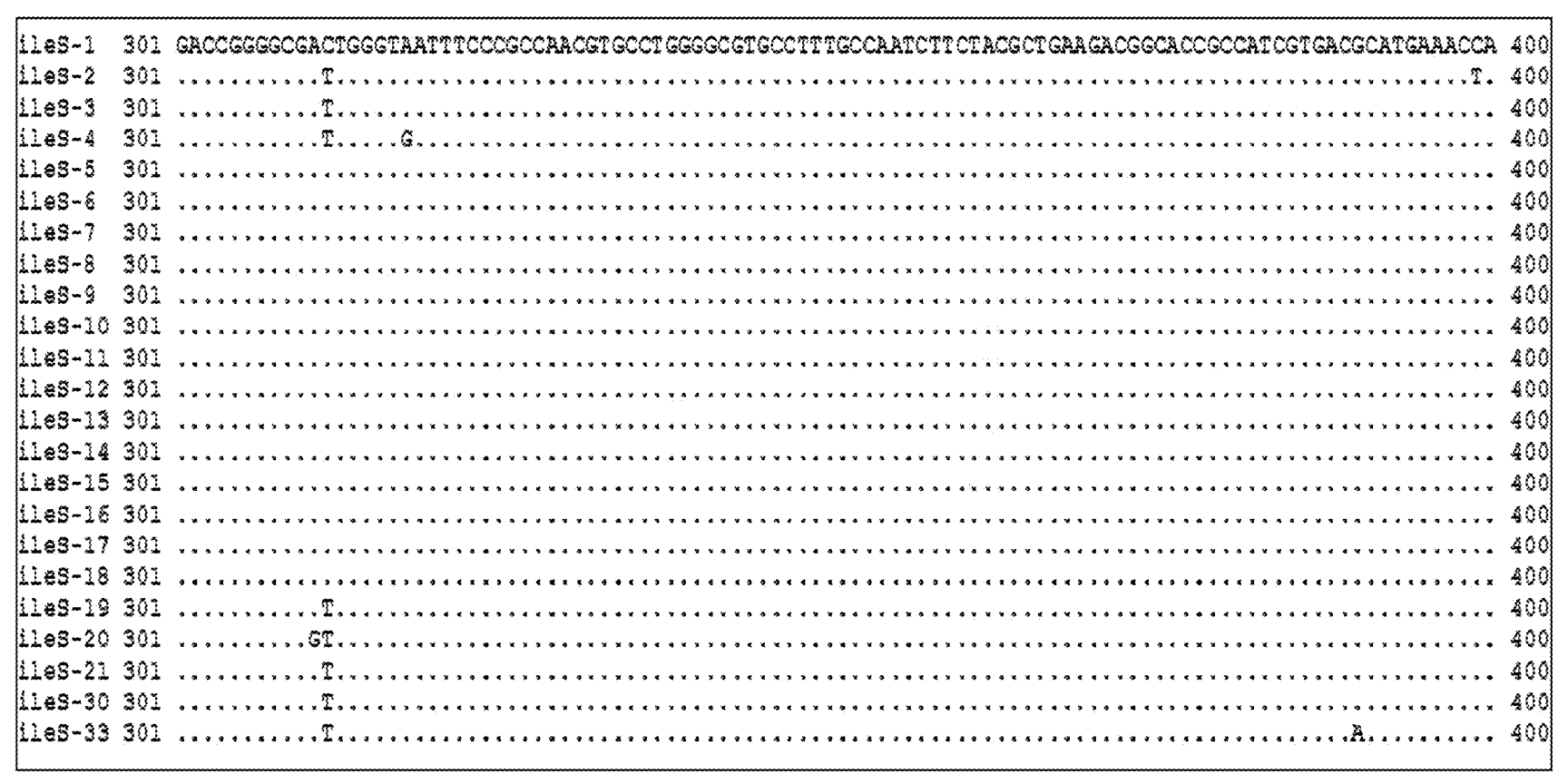
Figure 5E:
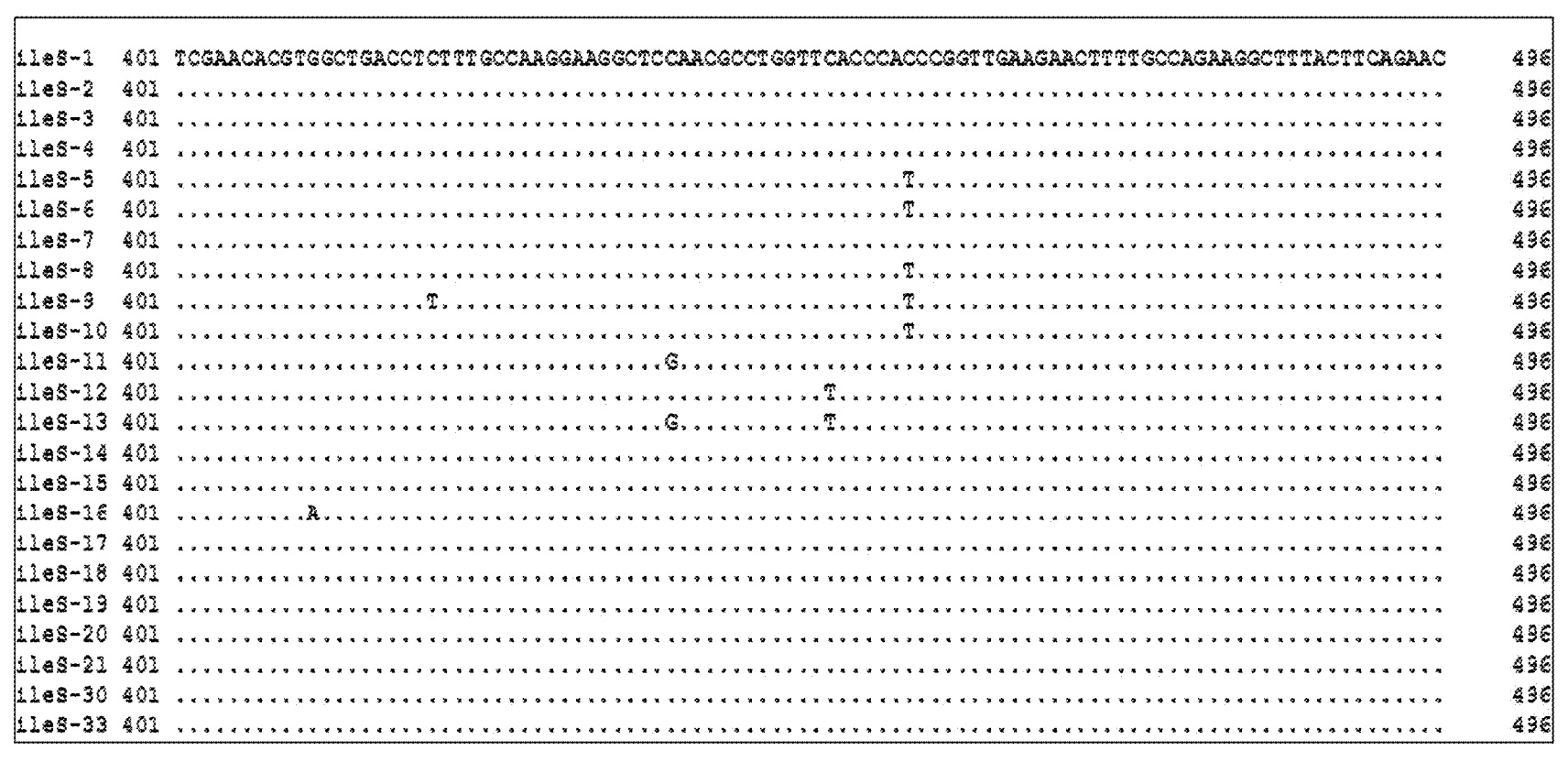
Figure 6B:
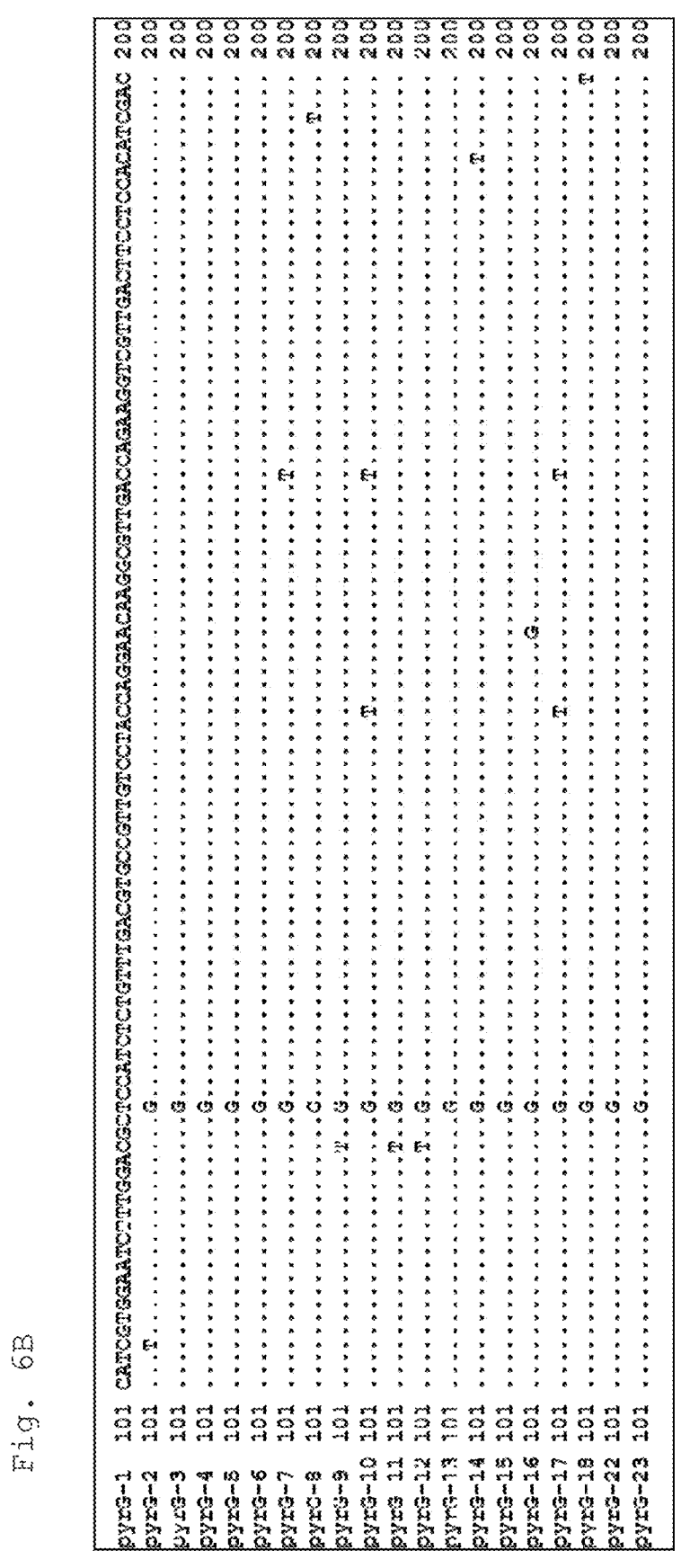
Figure 6C:
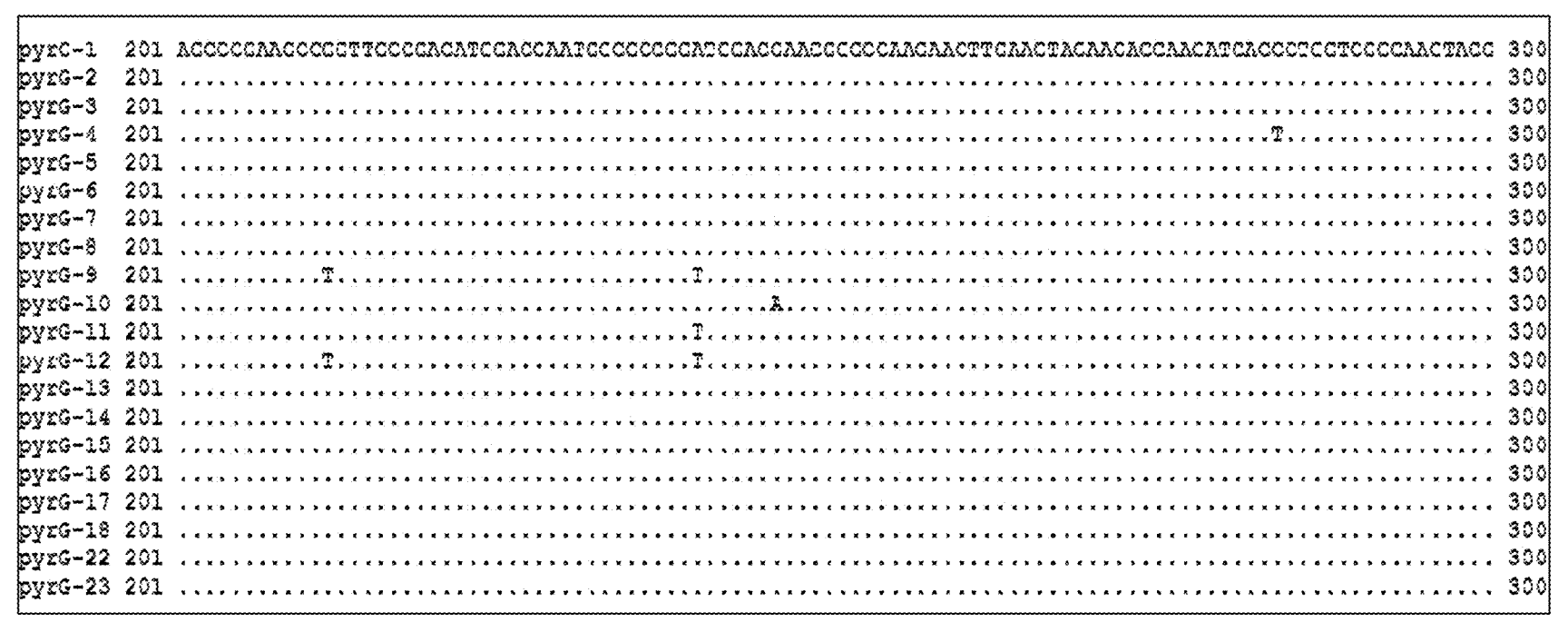
Figure 6D:
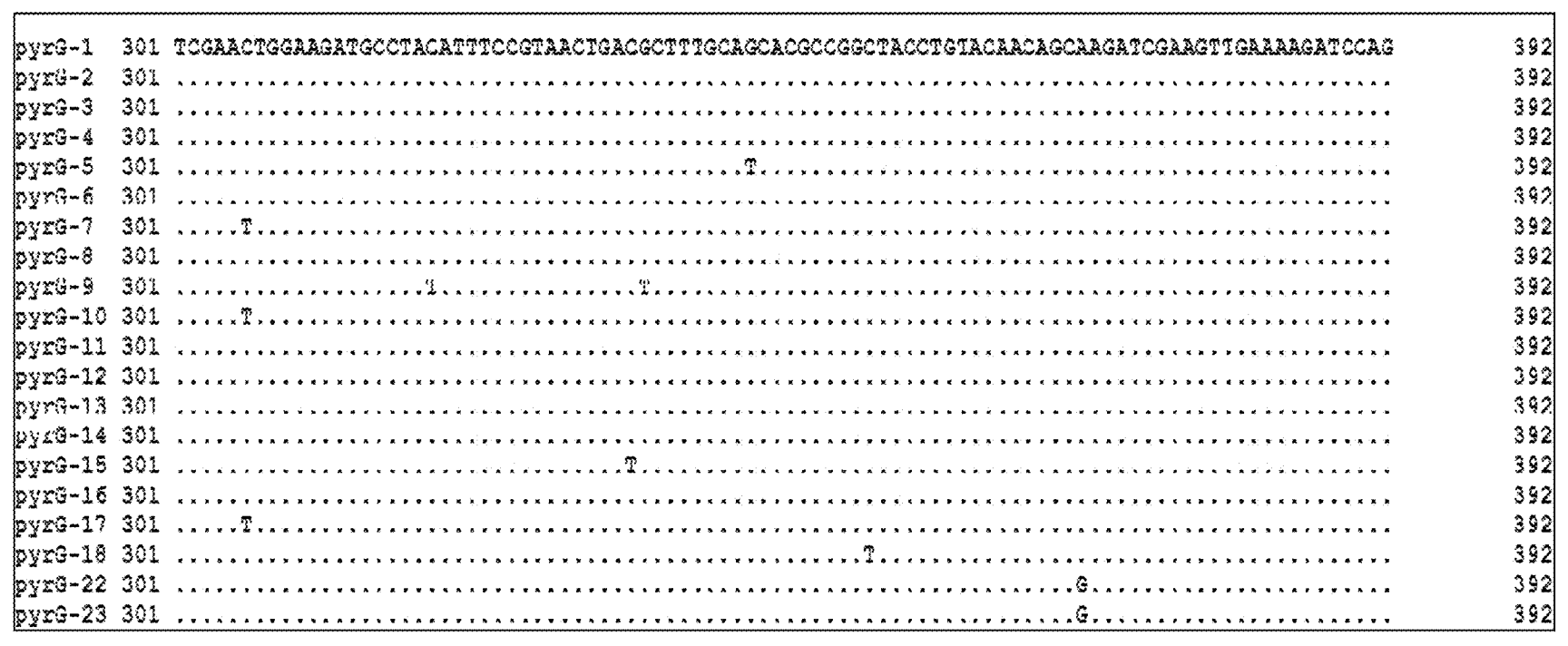
Figure 7A:
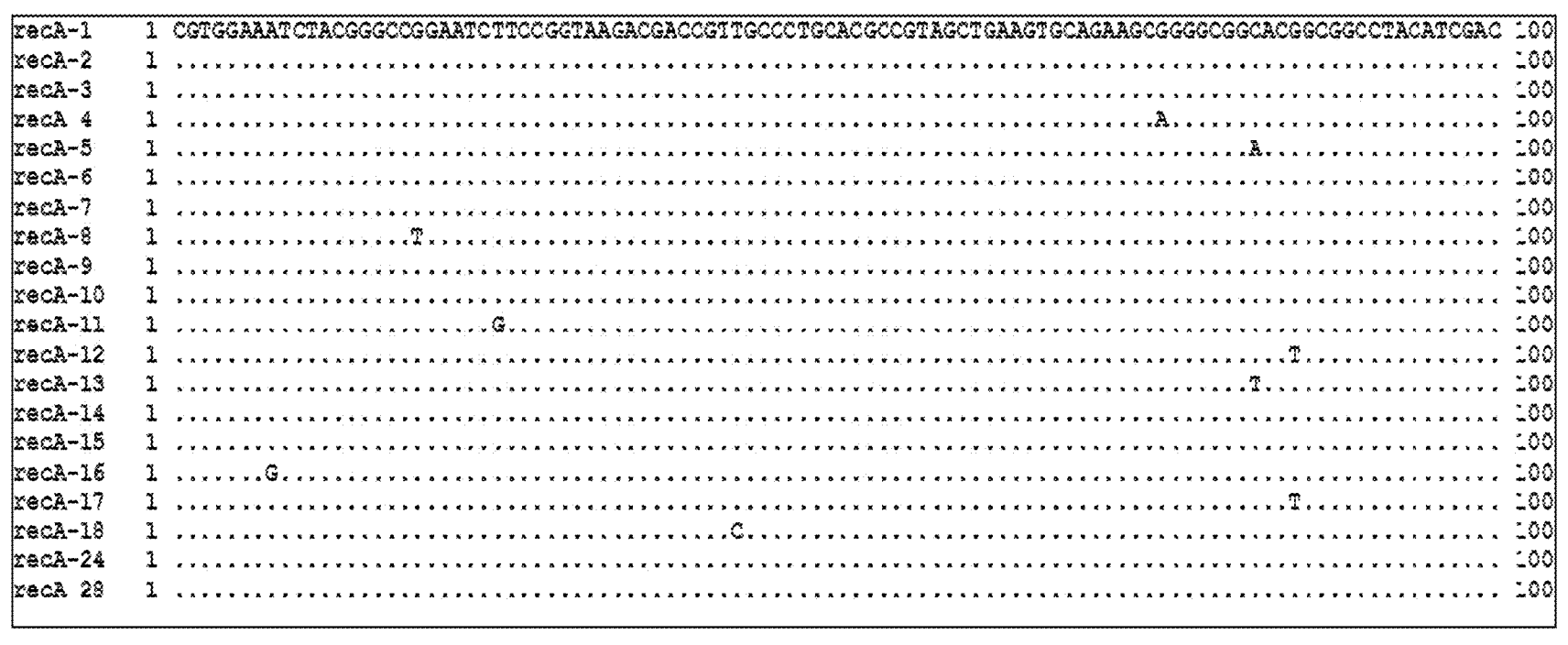
Figure 7B:
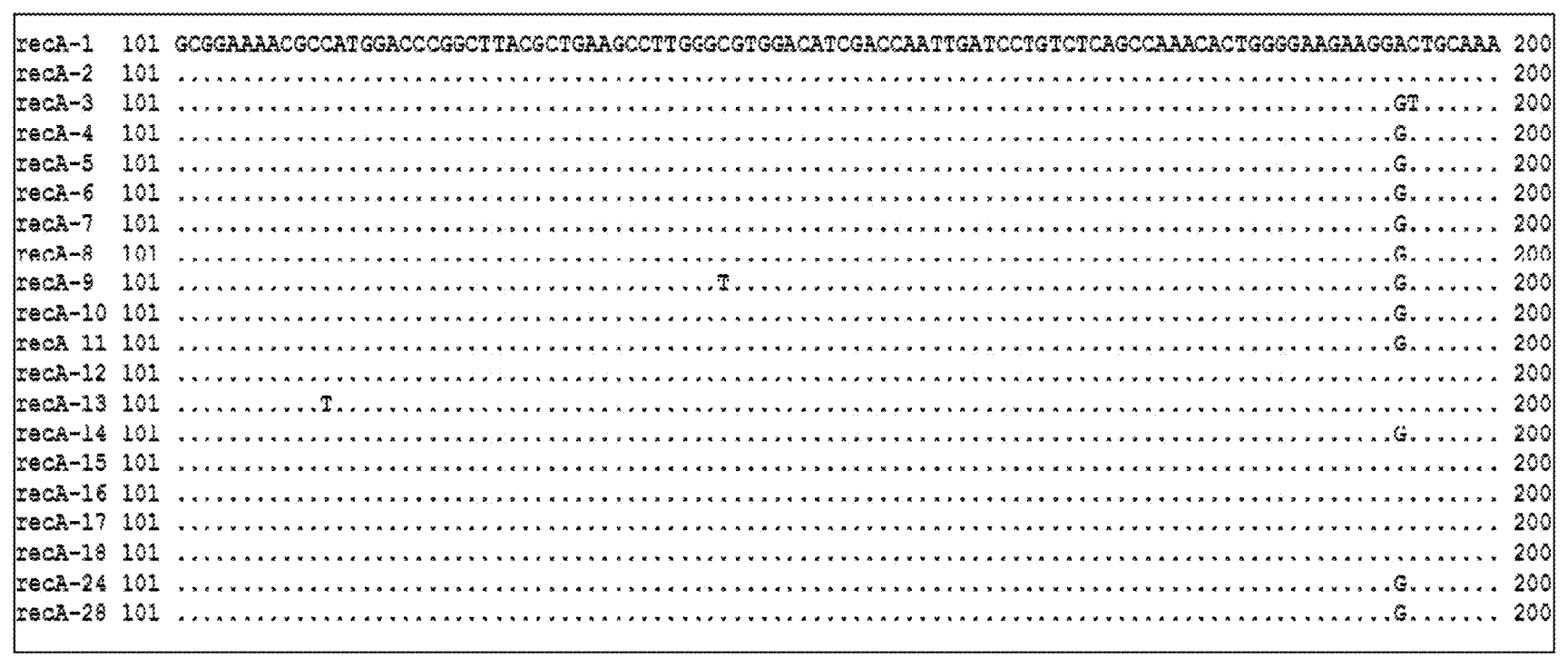
Figure 7C:
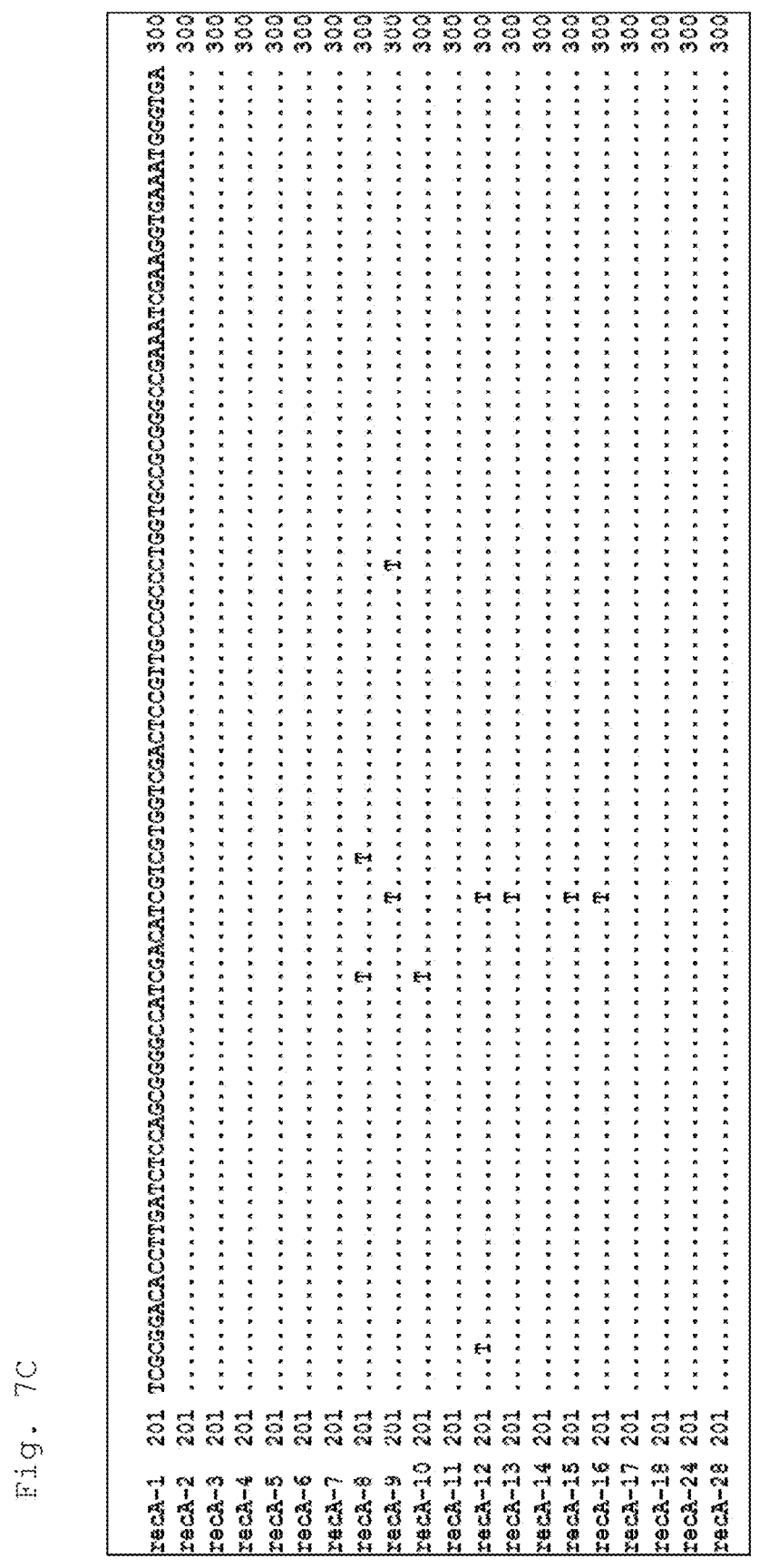
Figure 7D:
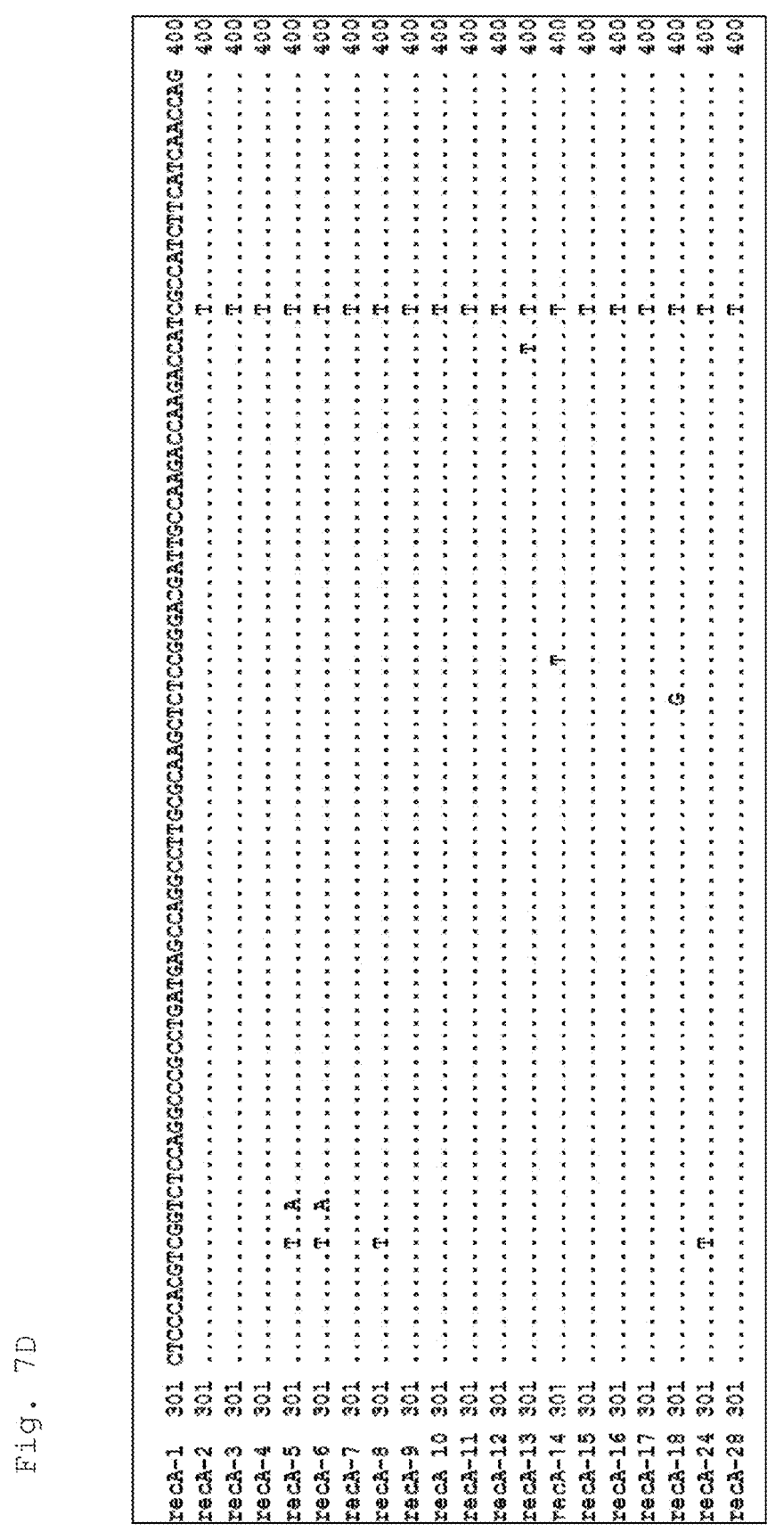
Figure 8A:
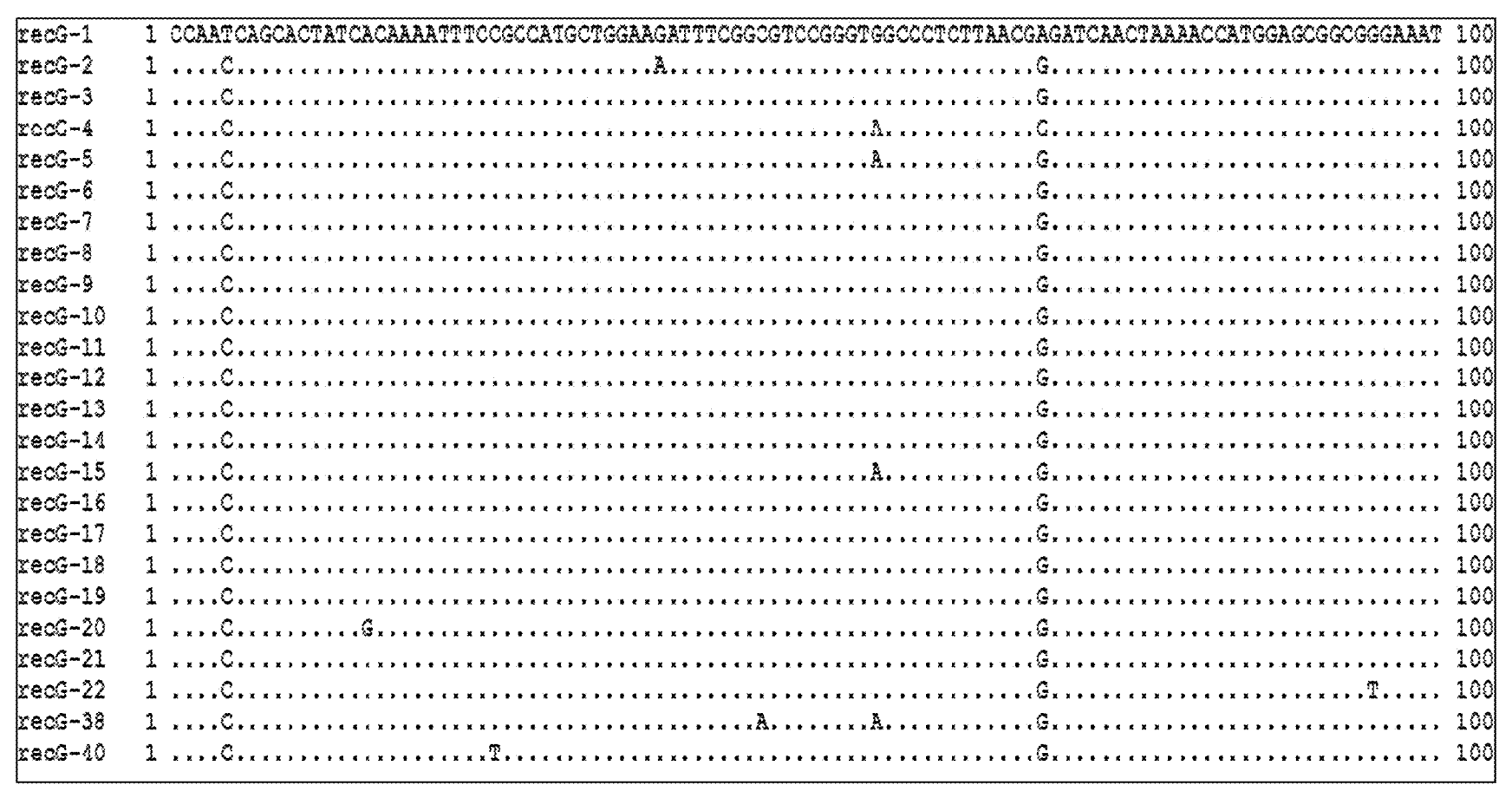
Figure 8C:
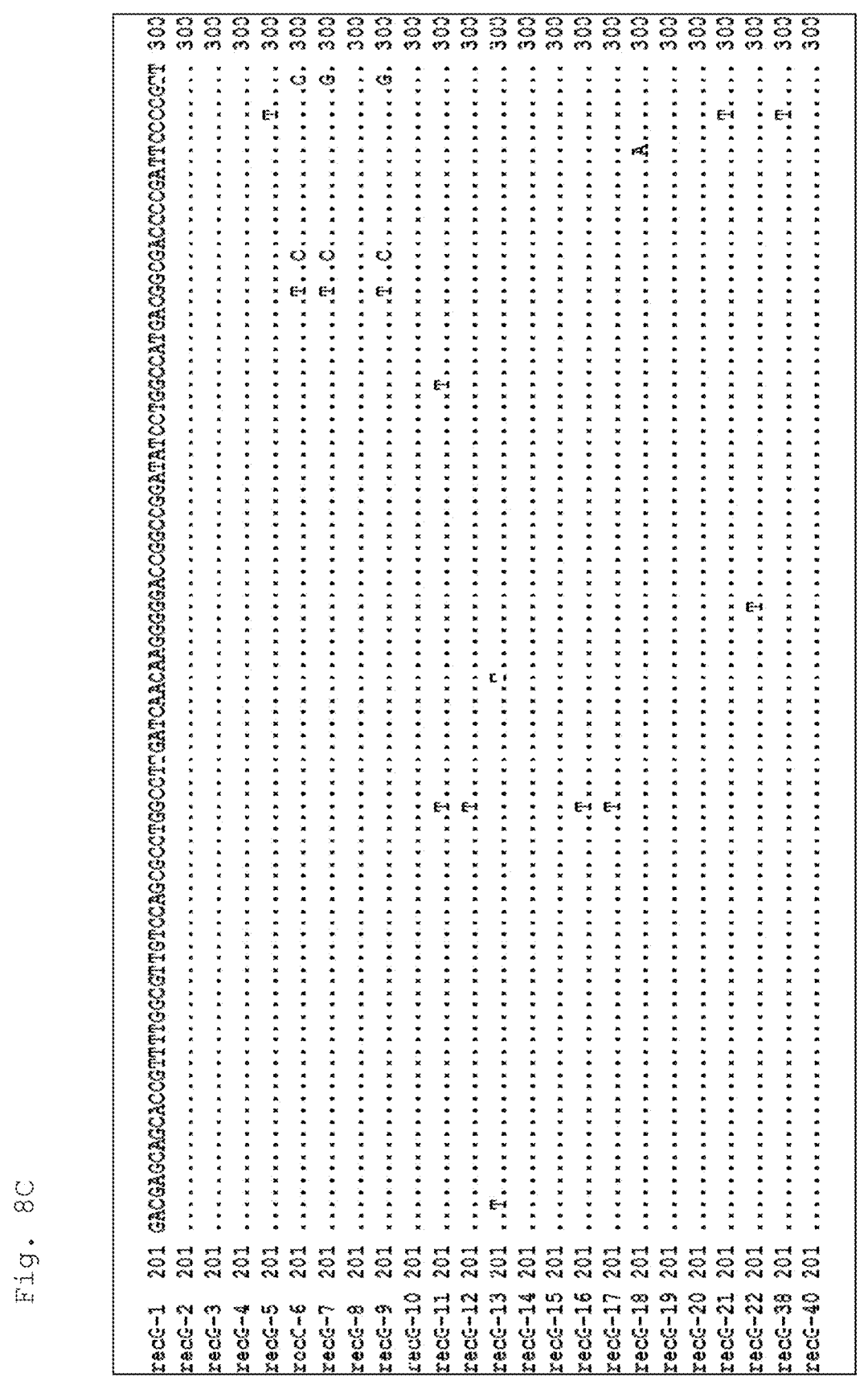
Figure 8D:
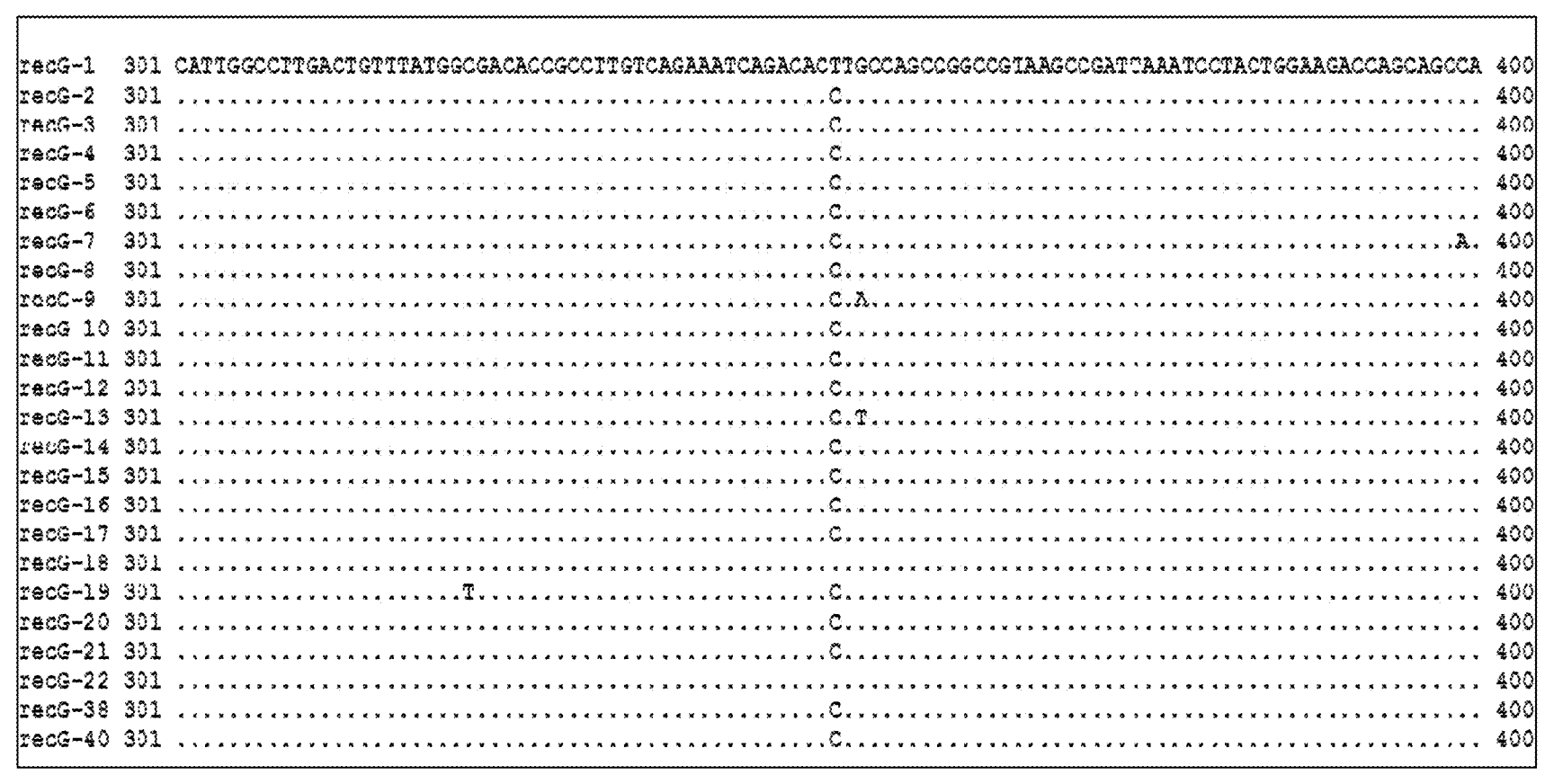
Figure 8E:
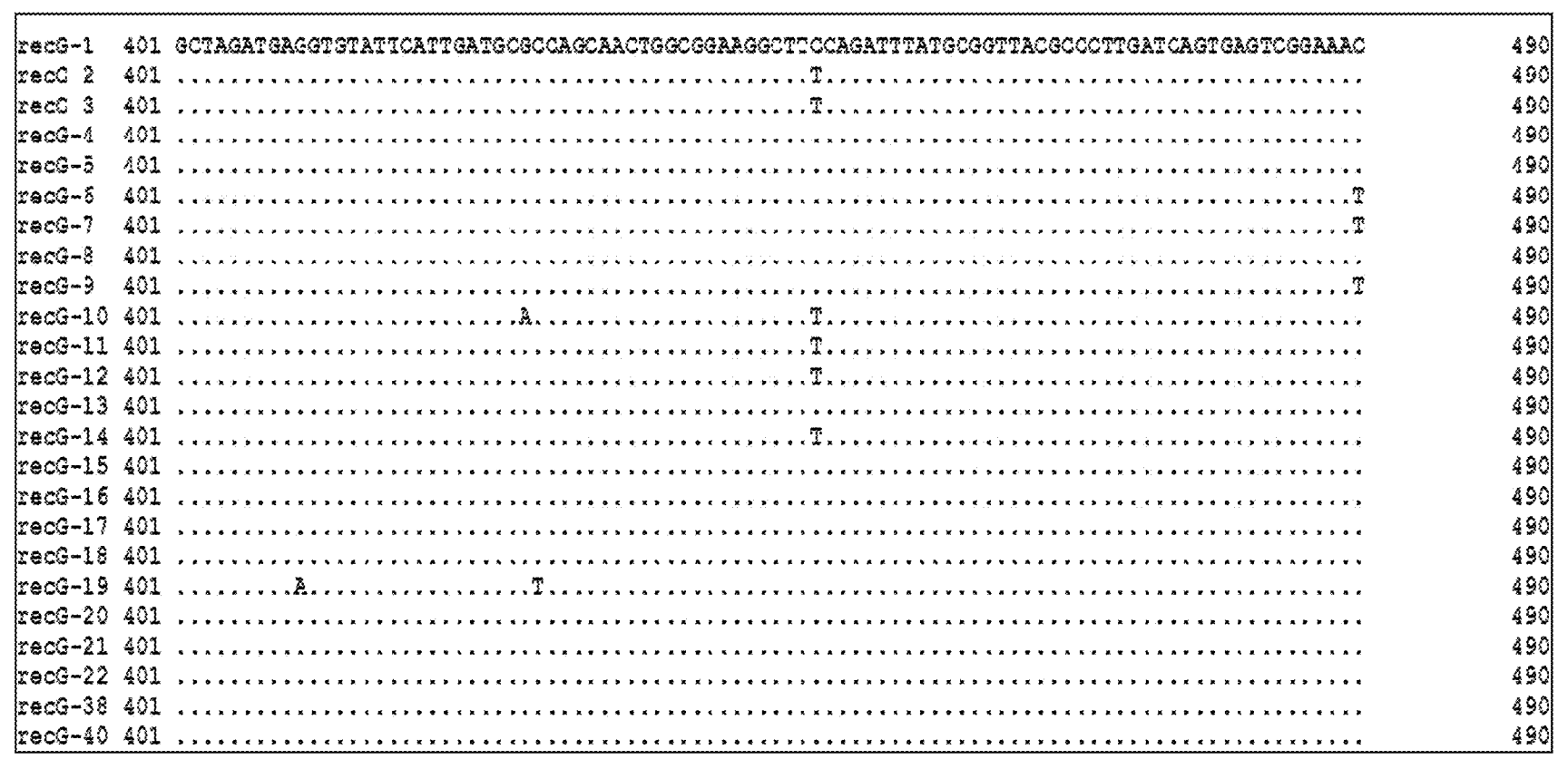

FIG. 2A to FIG. 8E illustrate a list of allele numbers of seven housekeeping genes consisting of fusA gene, gyrB gene, hsp60 gene, ileS gene, pyrG gene, recA gene, and recG gene according to the present invention, base sequences thereof, and polymorphic sites thereof (FIGS. 2A to 2C: fusA gene (the number following the hyphen (-) after "fusA" represents the allele number, and the same applies to the following), FIGS. 3A to 3D: gyrB gene, FIGS. 4A to 4F: hsp60 gene, FIGS. 5A to 5E: ileS gene, FIGS. 6A to 6D: pyrG gene, FIGS. 7A to 7E: recA gene, and FIGS. 8A to 8E: recG gene). FIG. 2A to FIG. 8E each present the entire base sequence with allele number 1 (the base sequence described in Tanigawa et al.), and present only different bases for the genes represented by the subsequent allele numbers. The allele number of each gene of the strains with strain Nos. 1 to 41 described in Tanigawa et al. basically represents the allele number described in Tanigawa et al. Note that, in Tanigawa et al., allele numbers 13 and 14 of the hsp60 gene and allele numbers 16 and 17 of the recG gene are assigned different numbers. Since they are the same single sequence as illustrated in FIGS. 4A to 4F and FIGS. 8A to 8E, these are written as allele numbers 13/14 and 16/17 in the present invention, as presented in Tables 1 and 2. For the allele number of each gene of the strains with strain Nos. 42 to 61, the base sequence of each housekeeping gene obtained by the method described in the above MLSA classification was compared with the above base sequences with strain Nos. 1 to 41 for each gene, and the base sequences that did not match any of the base sequences with strain Nos. 1 to 41 were assigned new allele numbers. Tables 1 and 2 below present the allele number of each gene of the above 61 strains. Tables 1 and 2 also present the cluster into which each strain is classified by the phylogenetic tree obtained by the above MLSA classification. In addition, Table 3 below presents a list of the sequence identification numbers and allele numbers of the base sequences of the housekeeping genes to which allele numbers were newly assigned this time (base sequences newly obtained this time; base sequences not described in Tanigawa et al.).

TABLE 1

| Strain No. | *Lactobacillus delbrueckii* Strain Name | Cluster | Allele Number | | | | | | |
|---|---|---|---|---|---|---|---|---|---|
| | | | fusA | gyrB | hsp60 | ileS | pyrG | recA | recG |
| 1 | YIT0080$^T$ (=JCM 1012$^T$) | II | 1 | 1 | 1 | 1 | 1 | 1 | 1 |
| 2 | YIT11851 | I-A | 2 | 4 | 1 | 19 | 6 | 7 | 22 |
| 3 | YIT12133 | I-A | 7 | 4 | 10 | 3 | 6 | 2 | 11 |
| 4 | YIT12134 | I-A | 8 | 4 | 4 | 3 | 6 | 2 | 12 |
| 5 | YIT0086$^T$ (=JCM 1248$^T$) | I-C | 2 | 3 | 3 | 2 | 18 | 17 | 3 |
| 6 | YIT0020 | I-C | 3 | 3 | 3 | 3 | 3 | 2 | 3 |
| 7 | YIT0058 | I-C | 2 | 3 | 3 | 3 | 3 | 2 | 3 |
| 8 | YIT0059 | I-C | 3 | 3 | 3 | 3 | 3 | 2 | 3 |
| 9 | YIT0087 | I-D | 2 | 4 | 4 | 4 | 4 | 3 | 4 |
| 10 | YIT0167 | I-D | 2 | 4 | 4 | 4 | 4 | 4 | 5 |
| 11 | YIT11852 | I-C | 3 | 3 | 3 | 3 | 3 | 2 | 3 |
| 12 | YIT11853 | I-C | 3 | 3 | 3 | 3 | 3 | 2 | 3 |
| 13 | YIT11854 | I-C | 3 | 3 | 3 | 3 | 3 | 4 | 3 |
| 14 | YIT0181$^T$ | IV | 4 | 5 | 5 | 5 | 5 | 5 | 6 |
| 15 | YIT0044 | IV | 4 | 6 | 6 | 6 | 6 | 6 | 7 |
| 16 | YIT0067 | IV | 4 | 8 | 5 | 8 | 8 | 6 | 6 |
| 17 | YIT0459 | IV | 4 | 6 | 8 | 9 | 6 | 6 | 9 |
| 18 | YIT0460 | IV | 4 | 6 | 6 | 6 | 6 | 6 | 7 |
| 19 | YIT0463 | IV | 4 | 8 | 5 | 5 | 6 | 6 | 6 |
| 20 | YIT0478 | IV | 4 | 6 | 6 | 10 | 6 | 6 | 7 |
| 21 | YIT11751$^T$ (=JCM 15610$^T$) | V | 6 | 9 | 9 | 11 | 9 | 8 | 10 |
| 22 | YIT12135 | V | 6 | 11 | 12 | 13 | 11 | 10 | 10 |
| 23 | YIT12136 | V | 6 | 12 | 9 | 13 | 12 | 10 | 14 |
| 24 | YIT12137 | V | 6 | 13 | 9 | 13 | 12 | 10 | 14 |

TABLE 1-continued

| Strain No. | *Lactobacillus delbrueckii* Strain Name | Cluster | Allele Number | | | | | | |
|---|---|---|---|---|---|---|---|---|---|
| | | | fusA | gyrB | hsp60 | ileS | pyrG | recA | recG |
| 25 | YIT0057 | I-C | 2 | 2 | 2 | 2 | 2 | 2 | 2 |
| 26 | YIT0373 | III-B | 5 | 7 | 7 | 7 | 7 | 7 | 8 |
| 27 | YIT11220 | III-A | 9 | 10 | 11 | 12 | 10 | 9 | 13 |
| 28 | YIT11221[T] (=JCM 17838[T]) | III-A | 9 | 10 | 11 | 17 | 10 | 9 | 13 |
| 29 | YIT11435 | I-E | 2 | 4 | 3 | 14 | 13 | 7 | 15 |
| 30 | YIT11451 | I-E | 2 | 4 | 3 | 14 | 13 | 7 | 15 |
| 31 | YIT11466 | III-A | 9 | 10 | 11 | 17 | 17 | 9 | 13 |
| 32 | YIT11468 | I-E | 2 | 4 | 3 | 14 | 13 | 7 | 15 |
| 33 | YIT11501 | I-F | 2 | 3 | 15 | 16 | 6 | 11 | 18 |
| 34 | YIT11502 | I-E | 10 | 4 | 13/14 | 15 | 14 | 7 | 16/17 |
| 35 | YIT11639 | I-E | 10 | 4 | 13/14 | 15 | 14 | 7 | 16/17 |
| 36 | YIT11673 | III-A | 9 | 10 | 11 | 17 | 10 | 9 | 13 |
| 37 | YIT11291 | I-E | 2 | 16 | 3 | 14 | 6 | 16 | 21 |
| 38 | YIT11293 | I-E | 2 | 16 | 3 | 14 | 6 | 15 | 20 |
| 39 | YIT11294 | I-E | 11 | 14 | 16 | 14 | 15 | 12 | 8 |
| 40 | YIT11300 | I-E | 12 | 4 | 3 | 18 | 6 | 13 | 15 |
| 41 | YIT11403 | I-G | 12 | 15 | 17 | 14 | 16 | 14 | 19 |
| 42 | DSM26046[T] (=JCM 30917[T]) | I-E | 18 | 27 | 3 | 14 | 6 | 15 | 40 |

TABLE 2

| Strain No. | *Lactobacillus delbrueckii* Strain Name | Cluster | Allele Number | | | | | | |
|---|---|---|---|---|---|---|---|---|---|
| | | | fusA | gyrB | hsp60 | ileS | pyrG | recA | recG |
| 43 | SQ-1 | I-B | 2 | 3 | 4 | 16 | 22 | 2 | 3 |
| 44 | SQ-2 | I-B | 2 | 3 | 4 | 21 | 22 | 7 | 3 |
| 45 | SQ-3 | I-B | 2 | 3 | 4 | 21 | 23 | 7 | 3 |
| 46 | NITE ABP-02874 (SQ-4) | I-B | 2 | 3 | 18 | 21 | 22 | 2 | 3 |
| 47 | MEP1900404 (SQ-5) | I-B | 2 | 3 | 18 | 21 | 22 | 7 | 3 |
| 48 | SQ-6 | I-B | 2 | 3 | 18 | 21 | 23 | 2 | 3 |
| 49 | MEP1900403 (SQ-7) | I-B | 2 | 3 | 18 | 30 | 22 | 7 | 3 |
| 50 | SQ-8 | I-B | 2 | 18 | 4 | 16 | 22 | 7 | 3 |
| 51 | SQ-9 | I-B | 2 | 18 | 4 | 16 | 23 | 7 | 3 |
| 52 | SQ-10 | I-B | 2 | 25 | 18 | 21 | 22 | 28 | 3 |
| 53 | SQ-11 | I-B | 14 | 17 | 18 | 20 | 22 | 7 | 3 |
| 54 | SQ-12 | I-B | 14 | 17 | 18 | 21 | 22 | 7 | 3 |
| 55 | SQ-13 | I-B | 14 | 17 | 18 | 21 | 22 | 24 | 3 |
| 56 | SQ-14 | I-B | 14 | 17 | 18 | 33 | 22 | 7 | 3 |
| 57 | MEP1900401 (SQ-15) | I-A | 13 | 4 | 4 | 3 | 6 | 11 | 16/17 |
| 58 | MEP1900407 (SQ-16) | I-F | 17 | 18 | 19 | 16 | 6 | 18 | 18 |
| 59 | SQ-17 | I-E | 13 | 26 | 3 | 14 | 6 | 15 | 38 |
| 60 | SQ-18 | I-B | 14 | 17 | 26 | 21 | 22 | 7 | 3 |
| 61 | SQ-19 | I-B | 2 | 3 | 27 | 21 | 22 | 7 | 3 |

TABLE 3

| Gene | Allele Number | SEQ ID NO |
|---|---|---|
| fusA | 13 | 1 |
| | 14 | 2 |
| | 17 | 3 |
| | 18 | 4 |
| gyrB | 17 | 5 |
| | 18 | 6 |
| | 25 | 7 |
| | 26 | 8 |
| | 27 | 9 |
| hsp60 | 18 | 10 |
| | 19 | 11 |
| | 26 | 42 |
| | 27 | 12 |
| ileS | 18 | 13 |
| | 19 | 14 |
| | 20 | 15 |
| | 21 | 16 |
| | 30 | 17 |
| | 33 | 18 |
| pyrG | 22 | 19 |
| | 23 | 20 |
| recA | 18 | 21 |
| | 24 | 22 |
| | 28 | 23 |

TABLE 3-continued

| Gene | Allele Number | SEQ ID NO |
|------|---------------|-----------|
| recG | 38            | 24        |
|      | 40            | 25        |

For *L. delbrueckii* except for the above 61 strains, for example, the base sequence of each housekeeping gene obtained by the method described in the above MLSA classification is compared with the above base sequences and allele numbers described in above FIG. 2A to FIG. 8E for each gene. Thereby, it is possible to obtain each allele number.

A preferable example of the *L. delbrueckii* satisfying all of the conditions (i) to (vii) is *L. delbrueckii* in which the allele numbers of the housekeeping genes carried are, in the order of fusA gene, gyrB gene, hsp60 gene, ileS gene, pyrG gene, recA gene, and recG gene, 2, 3, 4, 16, 22, 2, and 3;
2, 3, 4, 21, 22, 7, and 3;
2, 3, 4, 21, 23, 7, and 3;
2, 3, 18, 21, 22, 2, and 3;
2, 3, 18, 21, 22, 7, and 3;
2, 3, 18, 21, 23, 2, and 3;
2, 3, 18, 30, 22, 7, and 3;
2, 18, 4, 16, 22, 7, and 3;
2, 18, 4, 16, 23, 7, and 3;
2, 25, 18, 21, 22, 28, and 3;
14, 17, 18, 20, 22, 7, and 3;
14, 17, 18, 21, 22, 7, and 3;
14, 17, 18, 21, 22, 24, and 3;
14, 17, 18, 33, 22, 7, and 3;
14, 17, 26, 21, 22, 7, and 3; or
2, 3, 27, 21, 22, 7, and 3.

Among the *L. delbrueckii*, the *L. delbrueckii* according to the present invention is
more preferably at least one selected from the group consisting of
*L. delbrueckii* specified by accession number NITE BP-02874 (receipt number NITE ABP-02874) (*L. delbrueckii* NITE ABP-02874: strain No. 46 of Table 2) and
*L. delbrueckii* classified into the same cluster (that is, cluster I) as that of the *L. delbrueckii* specified by accession number NITE BP-02874 (receipt number NITE ABP-02874) by the above MLSA classification,
further preferably at least one selected from the group consisting of
the *L. delbrueckii* specified by accession number NITE BP-02874 and
*L. delbrueckii* classified into the same subcluster (that is, subcluster I-B) as that of the *L. delbrueckii* specified by accession number NITE BP-02874 (receipt number NITE ABP-02874) by the above MLSA classification, and
particularly preferably
the *L. delbrueckii* specified by accession number NITE BP-02874.

The *L. delbrueckii* specified by accession number NITE BP-02874 has been deposited in (1) deposition institute: National Institute of Technology and Evaluation, NITE Patent Microorganisms Depositary (NPMD) (postal code: 292-0818, 2-5-8 Kazusa-Kamatari, Kisarazu-shi, Chiba Prefecture, Room 122) with (2) receipt date (original deposition date): Feb. 5, 2019, (3) accession number NITE BP-02874 (receipt number: NITE ABP-02874), and (4) identification label: *Lactobacillus delbrueckii* OLL204989. Note that the *L. delbrueckii* specified by accession number NITE BP-02874 may be a passaged strain of the same strain, or an artificial mutant strain, a natural mutant strain, or a genetically modified strain of the same strain or a passaged strain thereof as long as the effects of the present invention are not impaired (preferably, within a scope that satisfies the preferred conditions of the *L. delbrueckii* according to the present invention). The *L. delbrueckii* specified by accession number NITE BP-02874 is *L. delbrueckii* which is *L. delbrueckii* Lac(+) and *L. delbrueckii* (I-B), and in which the allele numbers of the housekeeping genes carried are, in the order of fusA gene, gyrB gene, hsp60 gene, ileS gene, pyrG gene, recA gene, and recG gene, 2, 3, 18, 21, 22, 2, and 3.

(*Streptococcus Thermophilus*)

The method for producing a fermented food of the present invention ferments the above-described milk preparation solution added with a combination of *L. delbrueckii* and *Streptococcus thermophilus* carrying a prtS gene.

The *Streptococcus thermophilus* according to the present invention (hereinafter sometimes referred to as "*S. thermophilus*") is not particularly limited as long as it carries a prtS gene, and may be used alone or in combination of two or more. In the present invention, the "prtS gene" refers to a gene encoding a cell wall-bound serine protease that degradates casein.

In the present invention, whether or not *S. thermophilus* carries a prtS gene can be determined by, for example, whether or not a desired PCR product can be obtained by amplifying a part of the prtS gene using the following primers prepared from the highly conserved sequence of the prtS gene by the method described in the Examples below. By using *S. thermophilus* carrying the prtS gene (hereinafter sometimes referred to as "*S. thermophilus* prtS(+)"), even when combined with the *L. delbrueckii* Lac(−), the fermentation time can be significantly reduced as compared with the case of using *S. thermophilus* carrying no prtS gene (hereinafter sometimes referred to as "*S. thermophilus* prtS (−)"). Moreover, combination of the *S. thermophilus* prtS(+) and the *L. delbrueckii* classified into any one of clusters I, II, III, and V (more preferably cluster I, and further preferably subcluster I-B) by the above MLSA classification makes it possible to particularly obtain a fermented food having a balanced and mild flavor in all of acidity, umami, fermented aroma, and richness.

Such *S. thermophilus* prtS(+) is preferably *S. thermophilus* specified by accession number NITE BP-02875 (receipt number NITE ABP-02875). The *S. thermophilus* specified by accession number NITE BP-02875 is *S. thermophilus* prtS(+) derived from Japanese raw milk.

The *S. thermophilus* specified by accession number NITE BP-02875 has been deposited in (1) deposition institute: National Institute of Technology and Evaluation, NITE Patent Microorganisms Depositary (NPMD) (postal code: 292-0818, 2-5-8 Kazusa-Kamatari, Kisarazu-shi, Chiba Prefecture, Room 122) with (2) receipt date (original deposition date): Feb. 5, 2019, (3) accession number NITE BP-02875 (receipt number: NITE ABP-02875), and (4) identification label: *Streptococcus thermophilus* OLS4496. Note that the *S. thermophilus* specified by accession number NITE BP-02875 may be a passaged strain of the same strain, or an artificial mutant strain, a natural mutant strain, or a genetically modified strain of the same strain or a passaged strain thereof within a scope that satisfies the conditions according to the present invention.

(Fermentation)

As the fermentation step of fermenting above-described milk preparation solution added with the *L. delbrueckii* and the *S. thermophilus* prtS(+), a conventionally known method can be appropriately employed without particular limitation. The method is, for example, a method for fermenting the milk preparation solution inoculated with the *L. delbrueckii* and the *S. thermophilus* prtS(+) as fermentation starters.

The *L. delbrueckii* and the *S. thermophilus* prtS(+) may be, respectively, in the form of a lactic acid bacteria-containing composition and/or a processed product of the lactic acid bacterium, which contains both of these lactic acid bacteria or independently contains them. In the present invention, the lactic acid bacteria-containing composition includes a culture supernatant after the end of the culture of the lactic acid bacteria (*L. delbrueckii* and/or *S. thermophilus* prtS(+)) and a culture which is a medium component and the like; and a concentrate, a dilution, a dried product, a frozen product, and the like of the culture, or may include one of these alone or a combination of two or more thereof. In addition, in the present invention, the lactic acid bacteria-containing composition and/or the processed product of the lactic acid bacterium (lactic acid bacteria) include a crushed product and heat-treated product of the lactic acid bacterium (lactic acid bacteria) or the culture, their concentrate, dilution, dried product, frozen product, and the like, may include one of these alone or a combination of two or more thereof. Among these, the *L. delbrueckii* and the *S. thermophilus* prtS(+) are preferably added to the milk preparation solution in the form of the lactic acid bacteria-containing composition, and more preferably in the form of a culture or a concentrate of the culture.

The amount of the fermentation starters added can be appropriately set according to the addition amount employed in a conventionally known method for producing a fermented food, and is, for example, preferably $1 \times 10^7$ to $5 \times 10^9$ CFU/mL, and more preferably $1 \times 10^8$ to $2 \times 10^9$ CFU/mL relative to the volume of the milk preparation solution in terms of the number of lactic acid bacteria (total number of bacteria of *L. delbrueckii* and *S. thermophilus* prtS(+)).

In addition, the ratio of the number of bacteria between *L. delbrueckii* and *S. thermophilus* prtS(+) (*L. delbrueckii*:*S. thermophilus* prtS(+)) added to the milk preparation solution is preferably 1:0.1 to 1:100, and more preferably 1:1 to 1:10.

The method for inoculating the fermentation starters is not particularly limited, and a method commonly used in a method for producing a fermented food can be appropriately used. The *L. delbrueckii* and the *S. thermophilus* prtS(+) may be inoculated simultaneously with each other alone, or may be inoculated simultaneously after mixing them (for example, in the form of a lactic acid bacteria-containing composition containing both of them). The fermentation conditions can be appropriately selected without particular limitation according to the growth conditions of *L. delbrueckii* and *S. thermophilus* prtS(+) to be added, the amount of the milk preparation solution, and the like. For example, it is preferable to be static or stir (preferably be static) the milk preparation solution normally for 3 to 24 hours, more preferably 3 to 8 hours, and further preferably 4 to 6 hours at a temperature of 35 to 45° C. and more preferably a temperature of 38 to 43° C. under aerobic or anaerobic conditions until the pH of the milk preparation solution added with the *L. delbrueckii* and *S. thermophilus* prtS (+) reaches a value of 4.8 or less and more preferably a value between 4.0 and 4.6. The present invention makes it possible to significantly shorten the time required for fermentation even when *L. delbrueckii* Lac(−) is used. In addition, as the anaerobic condition, for example, fermentation under a nitrogen aerated condition can be employed.

The above fermentation makes it possible to obtain the fermented food of the present invention. The fermented product after the fermentation step can be used as the fermented food of the present invention as it is, or by concentrating, diluting, drying, or freezing as necessary. In addition, the fermented food of the present invention may be obtained by crushing or heating the lactic acid bacteria in the fermented product, or by concentrating, diluting, drying, or freezing them as necessary.

<Fermented Food>

The fermented food of the present invention contains the *L. delbrueckii* and the *S. thermophilus* prtS(+), and can be obtained by the above-described method for producing a fermented food of the present invention.

The fermented food of the present invention is not particularly limited, and may be, for example, any of the fermented foods defined in the Ministerial Ordinance on Milk and Milk products Concerning Compositional Standards, etc. by the Ministry of Health, Labor and Welfare of Japan: fermented milk satisfying the specifications of "fermented milk" (more specifically, the milk solids-not-fat content is 8.0% or more, and the lactic acid bacteria count or yeast count (preferably the lactic acid bacteria count (more preferably the total count of *L. delbrueckii* and *S. thermophilus* prtS(+), the same applies hereinafter)) is 10,000,000/mL or more), those satisfying the specifications of "milk product/lactic acid bacteria drink" (more specifically, the milk solids-not-fat content is 3.0% or more, and the lactic acid bacteria count or yeast count (preferably the lactic acid bacteria count) is 10,000,000/mL or more), and those satisfying the specifications of "lactic acid bacteria drink" (more specifically, the milk solids-not-fat content is less than 3.0%, and the lactic acid bacteria count or yeast count (preferably the lactic acid bacteria count) is 1,000,000/mL or more). Note that the milk solids-not-fat indicates the remaining components obtained by subtracting the fat content from the whole milk solid content (mainly, protein, lactose, and minerals), and the lactic acid bacteria count and yeast count are measured by a test method specified by the Ministerial Ordinance before sterilization.

The fermented food of the present invention may be a fermented product after the fermentation step, may be obtained by sterilizing the fermented product, or may be obtained by concentrating, diluting, drying, or freezing them. For example, the fermented milk may be a sterilized treatment product of the above-described fermented milk, milk product/lactic acid bacteria drink, or lactic acid bacteria drink. In this case, the lactic acid bacteria count (preferably the total count of *L. delbrueckii* and *S. thermophilus* prtS (+)) is in terms of live bacteria count. The lactic acid bacteria contained in the fermented food of the present invention include not only live bacteria but also dead bacteria, and include crushed products and heat-treated products of lactic acid bacteria, their concentrates, dilutions, dried products, and frozen products. Here, the lactic acid bacteria contained in the fermented food of the present invention preferably contain at least live bacteria.

The fermented food of the present invention may contain, as lactic acid bacteria, other lactic acid bacteria except for the *L. delbrueckii* and *S. thermophilus* prtS(+) according to the present invention, and may further contain yeast, as long as the effects of the present invention are not impaired. Examples of these other lactic acid bacteria and yeasts include lactic acid bacteria and yeasts conventionally known to be contained in fermented foods (such as fermented milk).

In addition, the fermented food of the present invention may further contain various components that can be contained in foods and drinks. Such components are not particularly limited, and examples thereof include water, saccharides, sugar alcohols, minerals, vitamins, proteins, peptides, amino acids, organic acids, pH adjusters, starch and processed starch, dietary fibers, fruits and vegetables and processed products thereof, animal and plant crude drug extracts, naturally derived polymers (such as collagen, hyaluronic acid, and chondroitin), oils and fats, thickeners, emulsifiers, solvents, surfactants, gelling agents, stabilizers, buffers, suspending agents, thickening agents, excipients, disintegrants, binders, flow agents, preservatives, coloring agents, flavors, corrigents, and sweeteners. One of these may be contained alone or in combination of two or more.

Such a fermented food is preferably fermented milk, and the fermented milk is preferably yogurt, cheese, fermented cream, fermented butter, and the like, and particularly preferably yogurt. Specific examples of the yogurt include set type yogurt (solid fermented milk) such as plain yogurt, soft type yogurt (pasty fermented milk), and drink type yogurt (liquid fermented milk). Frozen yogurt using these as materials may be employed. In addition, the fermented food of the present invention can also be used as a material for fermented foods such as cheese, fermented cream, fermented butter, and kefir.

EXAMPLES

Hereinafter, the present invention is described more specifically based on Examples and Comparative Examples, but the present invention is not limited to the following Examples. In the following Examples and Comparative Examples, the following methods were used to perform the confirmation of the presence or absence of the prtS gene carried by *S. thermophilus*, the confirmation of the presence or absence of lactose utilization of *L. delbrueckii*, and the cluster classification (MLSA classification) of *L. delbrueckii*.

<Detection of prtS Gene in S. *Thermophilus*>

The prtS gene sequences of five strains of *S. thermophilus* with known genomic sequences were obtained from the NCBI databases, and the following primers were prepared from highly conserved sequences (sequence identification number in the parentheses indicates the base sequence of each primer):

prtS gene forward primer (SEQ ID NO: 26)

prtS gene reverse primer (SEQ ID NO: 27).

In addition, InstaGene Matrix (manufactured by BioRad) was used to extract genomic DNA from the M17 culture of each strain. The extracted genomic DNA (template) in an amount of 0.5 µL, 1 µL of each prepared primer (5 µM), 0.1 µL of Phusion high fidelity DNA polymerase, 2 µL of 5×HF buffer, 0.8 µL of 2.5 mM dNTP, and 4.6 µL of ultrapure water were mixed (total of 10 µL), followed by PCR under the conditions presented in Table 4 below. The obtained PCR products were subjected to agarose gel electrophoresis, and the strain with a band observed at the position of 684 bp was determined as *S. thermophilus* carrying a prtS gene (*S. thermophilus* prtS(+)) and the strain without a band observed was determined as *S. thermophilus* carrying no prtS gene (*S. thermophilus* prtS(−)).

TABLE 4

| PCR Condition | | | |
|---|---|---|---|
| 98° C. | | 30 s | |
| 98° C. | 5 s | | 30 cycles |
| 63° C. | 20 s | | |
| 72° C. | 20 s | | |
| 72° C. | | 5 min | |
| 4° C. | | ∞ | |

<Assessment of a Lactose Utilization by L. *Delbrueckii*>

First, a modified MRS medium (purple) was prepared having no single sugar source (added with water) or glucose or lactose (for positive control: glucose; for negative control: water), and further added with a pH indicator (bromocresol purple: BCP). Table 5 below presents the composition of the modified MRS medium. Next, each of the *L. delbrueckii* strains to be evaluated was subjected to activation culture twice in an MRS Broth (37° C., anaerobic, cultured for 18 hours), and then the culture was centrifuged (2000×g, 4° C., 20 minutes), and the supernatant was discarded to collect the bacterial cells. Physiological saline was added to the collected bacterial cells to prepare a two-fold concentrated bacterial suspension. This bacterial suspension was added to a modified MRS medium at the ratio of 3.25% (mL/100 mL), and the mixture was incubated statically at 37° C. for 48 hours. After the end of the culture, the color of the culture was observed, and the utilization of lactose was confirmed according to the following criteria:

without lactose utilization (Lac(−)): the color of the culture having lactose as the single sugar source does not change even after the end of the culture, and it remains purple, which is the same as the color of the culture having no single sugar source (water) after the end of the culture, and is different from the color of the culture solution having glucose as the single sugar source after the end of the culture, and with lactose utilization (Lac(+)): the color of the culture having lactose as the single sugar source after the end of the culture has changed to yellow, and is the same as the color of the culture having glucose as the single sugar source after the end of the culture.

TABLE 5

| | For 1 L |
|---|---|
| Sugar | 10 g |
| Proteose Peptone No. 3 | 10 g |
| Yeast Extract | 5 g |
| Polysorbate 80 | 1 ml |
| Triammonium Citrate | 2 g |
| Sodium Acetate | 5 g |
| Magnesium Sulfate Heptahydrate | 0.1 g |
| Manganese Sulfate Pentahydrate | 0.05 g |
| $K_2HPO_4$ | 2 g |
| Bromocresol Purple | 0.17 g |

<Cluster Classification (MLSA Classification) of L. *Delbrueckii*>

(1) MLSA classification was performed on 59 strains of *L. delbrueckii*. Specifically, first, the same method as that described in Tanigawa et al. was used for 17 strains of *L. delbrueckii* presented in strain Nos. 43 to 59 in Table 2 above, and the following primers (sequence identification number in the parentheses indicates the base sequence of each primer), prepared from highly conserved sequences of fusA gene, gyrB gene, hsp60 gene, ileS gene, pyrG gene, recA gene, and recG gene, were used to amplify the sequences of the genes by the PCR method:

fusA gene: forward primer (SEQ ID NO: 28) and reverse primer (SEQ ID NO: 29),
gyrB gene: forward primer (SEQ ID NO: 30) and reverse primer (SEQ ID NO: 31),
hsp60 gene: forward primer (SEQ ID NO: 32) and reverse primer (SEQ ID NO: 33),
ileS gene: forward primer (SEQ ID NO: 34) and reverse primer (SEQ ID NO: 35),
pyrG gene: forward primer (SEQ ID NO: 36) and reverse primer (SEQ ID NO: 37),
recA gene: forward primer (SEQ ID NO: 38) and reverse primer (SEQ ID NO: 39), and
recG gene: forward primer (SEQ ID NO: 40) and reverse primer (SEQ ID NO: 41). Next, the base sequences of the obtained PCR products were determined, and for each strain, the base sequences of seven genes were concatenated in the order of fusA gene, gyrB gene, hsp60 gene, ileS gene, pyrG gene, recA gene, and recG gene to obtain a concatenated sequence.

In addition, the base sequences of fusA gene, gyrB gene, hsp60 gene, ileS gene, pyrG gene, recA gene, and recG gene of 41 strains described in Tanigawa et al. (strains with strain Nos. 1 to 41 of Table 1) and 1 strain described in Adimpong D. B. et al. (strain with strain No. 42 of Table 1) were obtained from the corresponding GeneBank/EMBL/DDBJ access numbers described in the documents and concatenated to each other in the same manner as above to obtain concatenated sequences.

Next, a phylogenetic tree was constructed for all of the 59 strains described above by the unweighted pair group method with arithmetic mean (UPGMA) using Genetyx v. 13 (manufactured by GENETYX CORPORATION) based on the obtained concatenated sequences.

In addition, also for the 2 strains of *L. delbrueckii* with strain Nos. 60 and 61 presented in Table 2 above, the above primers were used to amplify the sequences of the genes by the PCR method, and a concatenated sequence was obtained for each strain. Subsequently, 2 strains of *L. delbrueckii* with strain Nos. 60 and 61 were added to the above 59 strains, and a phylogenetic tree was constructed for all 61 strains in the same manner as described above. In the 59 strains with strain Nos. 1 to 59, the clusters classified by the phylogenetic tree obtained by the 59 strains and the clusters classified by the phylogenetic tree obtained by the 61 strains were identical to each other, including the subclusters. FIG. 1 above illustrates a phylogenetic tree obtained from all the 61 strains. In addition, the clusters classified by the phylogenetic trees are presented in Tables 1 and 2.

(2) For *L. delbrueckii* described in Table 6 below except for the 61 strains, first, in the same manner as in the strains with strain Nos. 43 to 59, the base sequence and concatenated sequence for the seven genes were obtained. Next, a phylogenetic tree was constructed in the same manner as in (1) above from the concatenated sequences of all of the 59 strains described above and the obtained concatenated sequence of one target strain (concatenated sequences of all 60 strains). In the obtained phylogenetic tree, the cluster into which the target strain was classified was defined as the cluster of that strain.

<Measurement of Fermentation Time>

The time required for fermentation was measured using the strains of *L. delbrueckii* which are presented in Table 6 below and for which the presence or absence of lactose utilization and clusters were confirmed by the above method in combination with the strain of *S. thermophilus* carrying no prtS gene (*S. thermophilus* 1131, isolated from Meiji Bulgaria Yogurt LB81 (manufactured by Meiji Co., Ltd.)) or the strain of *S. thermophilus* carrying a prtS gene (*S. thermophilus* NITE ABP-02875, derived from Japanese raw milk, *S. thermophilus* specified by accession number NITE BP-02875 (receipt number NITE ABP-02875)), both of which had been confirmed for the presence or absence of prtS gene carried, in the combinations of Table 6 below (Y1 to Y20, Y6K(−): Comparative Examples; Y21 to Y40, Y6K(+): Examples; S1 and S2: Reference Examples). Table 6 also presents the presence or absence of the prtS gene carried by each *S. thermophilus* (prtS(+)/prtS(−)), the cluster of each *L. delbrueckii* by the MLSA classification (MLSA cluster), and lactose utilization (+: Lac(+)/−: Lac(−)).

TABLE 6

| | MLSA Cluster | Strain Name | Lactose Utilization | *S. thermophilus* prtS(−) 1131 | *S. thermophilus* prtS(+) NITE ABP-02875 |
|---|---|---|---|---|---|
| *L. delbrueckii* | I-A | MEP1900401 | + | Y1 | Y21 |
| | | MEP1900402 | + | Y2 | Y22 |
| | I-B | MEP1900403 | + | Y3 | Y23 |
| | | MEP1900404 | + | Y4 | Y24 |
| | | NITE ABP-02874 | + | Y6K(−) | Y6K(+) |
| | I-C | JCM 1248$^T$ | + | Y5 | Y25 |
| | | MEP1900405 | + | Y6 | Y26 |
| | I-E | JCM 30917$^T$ | − | Y7 | Y27 |
| | | MEP1900406 | + | Y8 | Y28 |
| | I-F | MEP1900407 | + | Y9 | Y29 |
| | | MEP1900408 | + | Y10 | Y30 |
| | III-A | JCM 17838$^T$ | − | Y11 | Y31 |
| | | MEP1900409 | − | Y12 | Y32 |
| | III-B | MEP1900410 | + | Y13 | Y33 |
| | | MEP1900411 | + | Y14 | Y34 |
| | II | JCM 1012$^T$ | − | Y15 | Y35 |
| | IV | 2038 | + | Y16 | Y36 |
| | | NITE BP-76 | + | Y17 | Y37 |
| | | MEP1900412 | + | Y18 | Y38 |
| | V | JCM 15610$^T$ | + | Y19 | Y39 |
| | | MEP1900413 | + | Y20 | Y40 |
| | − (*S. thermophilus* alone) | | | S1 | S2 |

The fermentation was as follows. Commercially available milk was added with each strain at 0.5% (0.5 mL/100 mL, the same applies to the following) or a combination thereof (*L. delbrueckii*:*S. thermophilus*=about 1:1 (bacterial count)) so that the amount of each strain was 0.5% (1% in total), followed by fermentation at 43° C. for 24 hours (aerobic, static culture) to obtain various types of fermented milk. The time from the addition of each strain until the pH reached 4.5 was measured and defined as the fermentation time required for fermentation. Table 7 below presents the results. Note that, if the pH did not reach 4.5 within 24 hours from the addition of strain, the fermentation was terminated with the fermentation time defined as 24 hours (1440 minutes).

TABLE 7

| Combination No. (prtS(−)) | Fermentation Time [min] | Combination No. (prtS(+)) | Fermentation Time [min] |
|---|---|---|---|
| Y1 | 897 | Y21 | 462 |
| Y2 | 1440 | Y22 | 498 |
| Y3 | 432 | Y23 | 348 |
| Y4 | 417 | Y24 | 348 |
| Y6K(−) | 396 | Y6K(+) | 327 |
| Y5 | 1056 | Y25 | 546 |
| Y6 | 684 | Y26 | 411 |

TABLE 7-continued

| Combination No. (prtS(-)) | Fermentation Time [min] | Combination No. (prtS(+)) | Fermentation Time [min] |
|---|---|---|---|
| Y7 | 1440 | Y27 | 468 |
| Y8 | 768 | Y28 | 429 |
| Y9 | 375 | Y29 | 309 |
| Y10 | 480 | Y30 | 393 |
| Y11 | 849 | Y31 | 522 |
| Y12 | 942 | Y32 | 507 |
| Y13 | 642 | Y33 | 471 |
| Y14 | 921 | Y34 | 474 |
| Y15 | 1440 | Y35 | 573 |
| Y16 | 711 | Y36 | 435 |
| Y17 | 528 | Y37 | 384 |
| Y18 | 540 | Y38 | 468 |
| Y19 | 567 | Y39 | 438 |
| Y20 | 465 | Y40 | 369 |
| Average | 761 | Average | 437 |
| SD | 346 | SD | 73 |
| S1 | 1440 | S2 | 699 |

Figure 9:
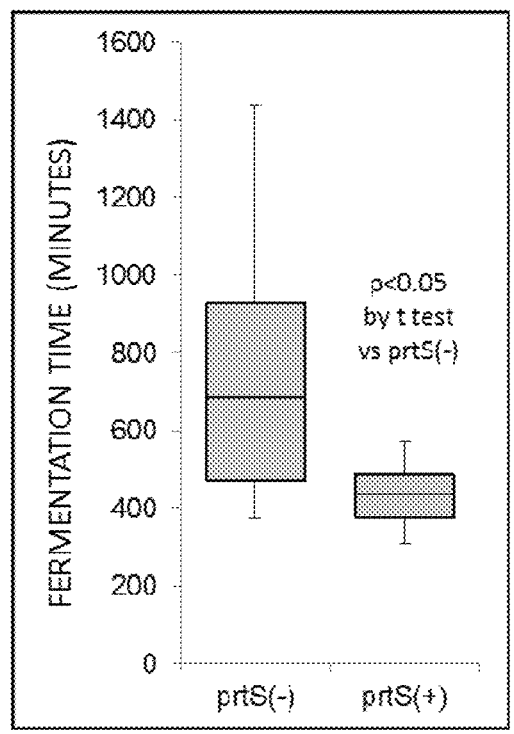
FIG. 9 is a graph illustrating the fermentation times when using *S. thermophilus* prtS(−) and when using *S. thermophilus* prtS(+)

In addition, FIG. 9 illustrates fermentation times (average values, minutes) when using *S. thermophilus* prtS(−) (Y1 to Y20, Y6K(−) (n=21)) (prtS(−)) and when using *S. thermophilus* prtS(+) (Y21 to Y40, Y6K(+) (n=21)) (prtS(+)). A comparison between average fermentation time when using of prtS(−) and one when using of prtS(+) by t-test showed that p-value was less than 0.05. As illustrated in FIG. 9, it was confirmed that use of *S. thermophilus* prtS(+) significantly shortened the fermentation time as compared with the case of using *S. thermophilus* prtS(−). In addition, as presented in Table 7, it was confirmed that use of *S. thermophilus* prtS(+) shortened the fermentation time even in the case of a single *S. thermophilus* strain.

Figure 10:
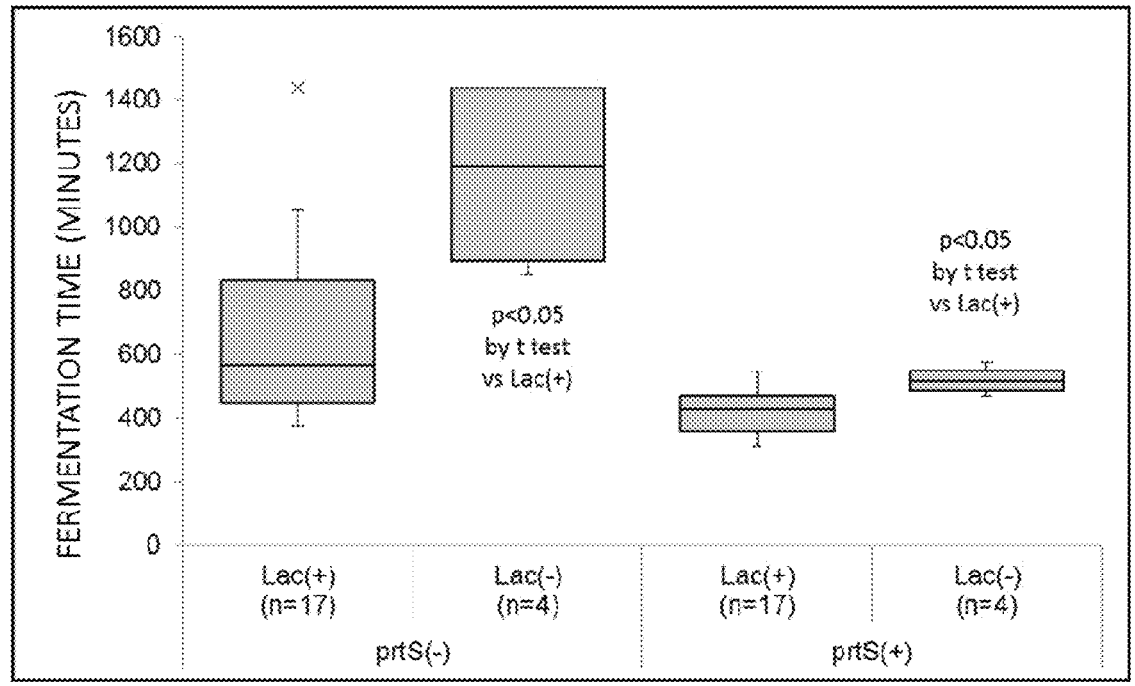
FIG. 10 is a graph illustrating the fermentation times when using *L. delbrueckii* Lac(−) and when using *L. delbrueckii* Lac(+)

FIG. 10 illustrates the fermentation times (average values, minutes) depending on the presence or absence of lactose utilization of *L. delbrueckii* for each of these *S. thermophilus*. Specifically, the figure provides the fermentation time for each of the cases of using *S. thermophilus* prtS(−) and *L. delbrueckii* Lac(+) (prtS(−)-Lac(+): Y1 to Y6, Y8 to Y10, Y13, Y14, Y16 to Y20, Y6K(−), n=17), using *S. thermophilus* prtS(−) and *L. delbrueckii* Lac(−) (prtS(−)-Lac(−): Y7, Y11, Y12, Y15, n=4), using *S. thermophilus* prtS(+) and *L. delbrueckii* Lac(+) (prtS(+)-Lac(+): Y21 to Y26, Y28 to Y30, Y33, Y34, Y36 to Y40, Y6K(+), n=17), and using *S. thermophilus* prtS(+) and *L. delbrueckii* Lac(−) (prtS(+)-Lac(−): Y27, Y31, Y32, Y35, n=4). A comparison between average fermentation time when using of Lac(−) and one when using of Lac(+) by t-test showed that p-value was less than 0.05. As illustrated in FIG. 10, the fermentation time was longer in the case of using *L. delbrueckii* Lac(−) than in the case of using *L. delbrueckii* Lac(+) regardless of which *S. thermophilus* was used. However, in the case of using *S. thermophilus* prtS(+), it was confirmed that the fermentation time was significantly shortened even in combination with such *L. delbrueckii* Lac(−).

<Analysis of Water-Soluble Component (in the Fermented Milk)>

In the above fermentation time measurement, the water-soluble components in the fermented milk obtained using various combinations of strains were analyzed by capillary electrophoresis-time-of-flight mass spectrometer (CE-TOF MS) according to the following method (Human Metabolome Technologies Inc.).

(Pretreatment)

To 900 μL of a methanol solution prepared so that the concentration of the internal standard substance was 10 μM, 100 μL of fermented milk was added, followed by stirring. Chloroform in an amount of 1,000 μL and ultrapure water in an amount of 400 μL were added thereto, followed by stirring and centrifugation (2,300×g, 4° C., 5 minutes). After centrifugation, 400 μL of the aqueous layer was transferred to an ultrafiltration tube (Ultrafree MC PLHCC, HMT, centrifugal filter unit 5 kDa). This was centrifuged (9,100×g, 4° C., 120 minutes) and subjected to ultrafiltration treatment. The filtrate was dried and dissolved again in 50 μL of ultrapure water for measurement.

(Measurement)

The cationic mode and the anionic mode were measured under the conditions presented in Table 8 below.

TABLE 8

| Cationic Metabolite (Cationic Mode) | |
|---|---|
| Apparatus | Agilent CE-TOF MS system (manufactured by Agilent Technologies) Capillary: Fused silica capillary i.d. 50 μm × 80 cm |
| Measurement Condition | Run buffer: Cation Buffer Solution (p/n: H3301-1001) Rinse buffer: Cation Buffer Solution (p/n: H3301-1001) Sample injection: Pressure injection 50 mbar, 10 sec CE voltage: Positive, 27 kV MS ionization: ESI Positive MS capillary voltage: 4,000 V MS scan range: m/z 50-1,000 Sheath liquid: HMT Sheath Liquid (p/n: H3301-1020) |
| Anionic Metabolite (Cationic Mode) | |
| | Run buffer: Anion Buffer Solution (p/n: H3302-1021) Rinse buffer: Anion Buffer Solution (p/n: H3302-1021) Sample injection: Pressure injection 50 mbar, 25 sec CE voltage: Positive, 30 kV MS ionization: ESI Negative MS capillary voltage: 3,500 V MS scan range: m/z 50-1,000 Sheath liquid: HMT Sheath Liquid (p/n: H3301-1020) |

(Data Processing)

For the peaks detected by CE-TOF MS, automatic integration software MasterHands ver. 2.17.1.11 (developed by Keio University) was used to automatically extract peaks having a signal/noise (S/N) ratio of 3 or more, thereby obtaining a mass-to-charge ratio (m/z), a peak area value, and a migration time (MT). The obtained peak area value was converted into a relative area value using the following equation:

relative area value=(area value of target peak)/(area value of internal standard substance×amount of sample).

In addition, since these datasets included adduct ions such as $Na^+$ and $K^+$ and fragment ions such as dehydration and deammoniation, these molecular weight-related ions were deleted. However, due to the presence of substance-specific adducts and fragments, it was impossible to closely examine all of them. For the peaks examined closely, the peaks of the samples were collated and aligned based on the values of m/z and MT.

(Search for Candidate Metabolites)

Based on the values of m/z and MT, the detected peaks were collated and searched against all substances registered in the HMT metabolite library and the known-unknown library (Human Metabolome Technologies Inc.). The tolerable error for the search was ±0.5 min for MT and ±10 ppm for m/z (mass error (ppm)=(measured value−theoretical value)×$10^6$/measured value). Note that, in the case where the same candidate metabolite was assigned to more than one peak because the candidates could not be narrowed down, peak numbers were assigned for labeling.

(Quantification of Target Metabolic Compound)

The target metabolic compound was analyzed. For the calibration curve, the peak area corrected by the internal standard substance was used, and the concentration was calculated for each substance as one point calibration with 100 μM (internal standard substance: 200 μM).

(Results)

Figure 11:
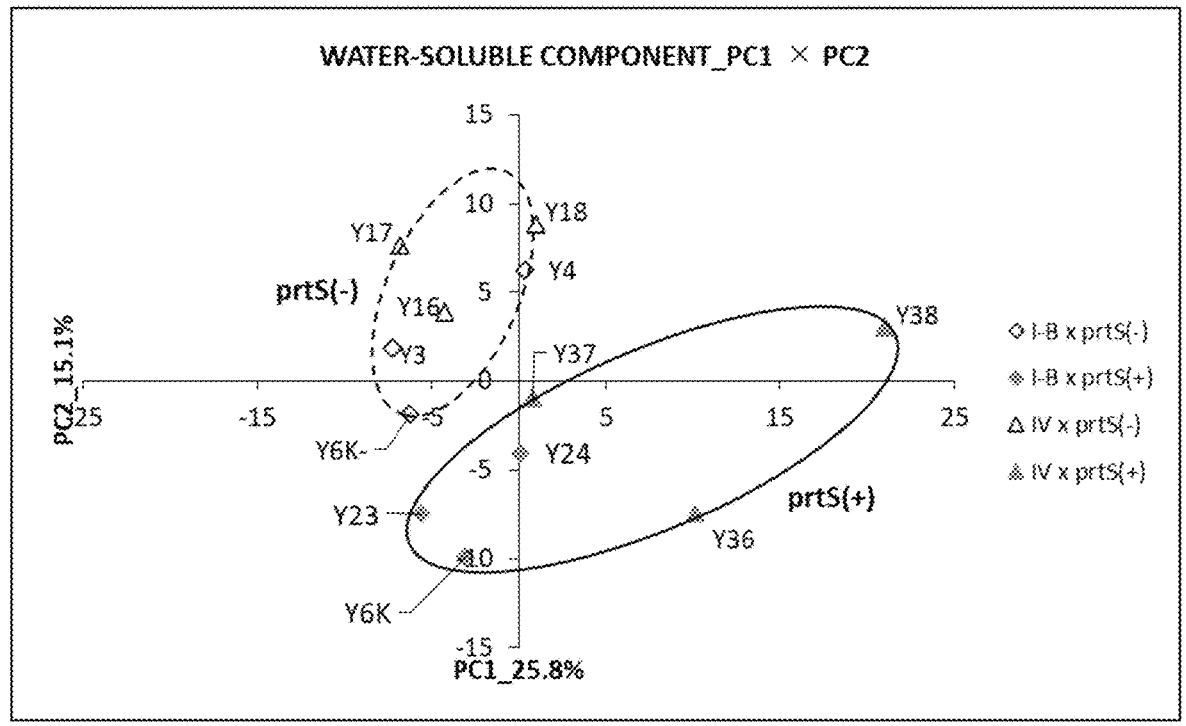
FIG. 11 is a diagram illustrating the relationship between the first principal component score (PC1) and the second principal component score (PC2) in the analysis result of water-soluble component (1)
Figure 12:
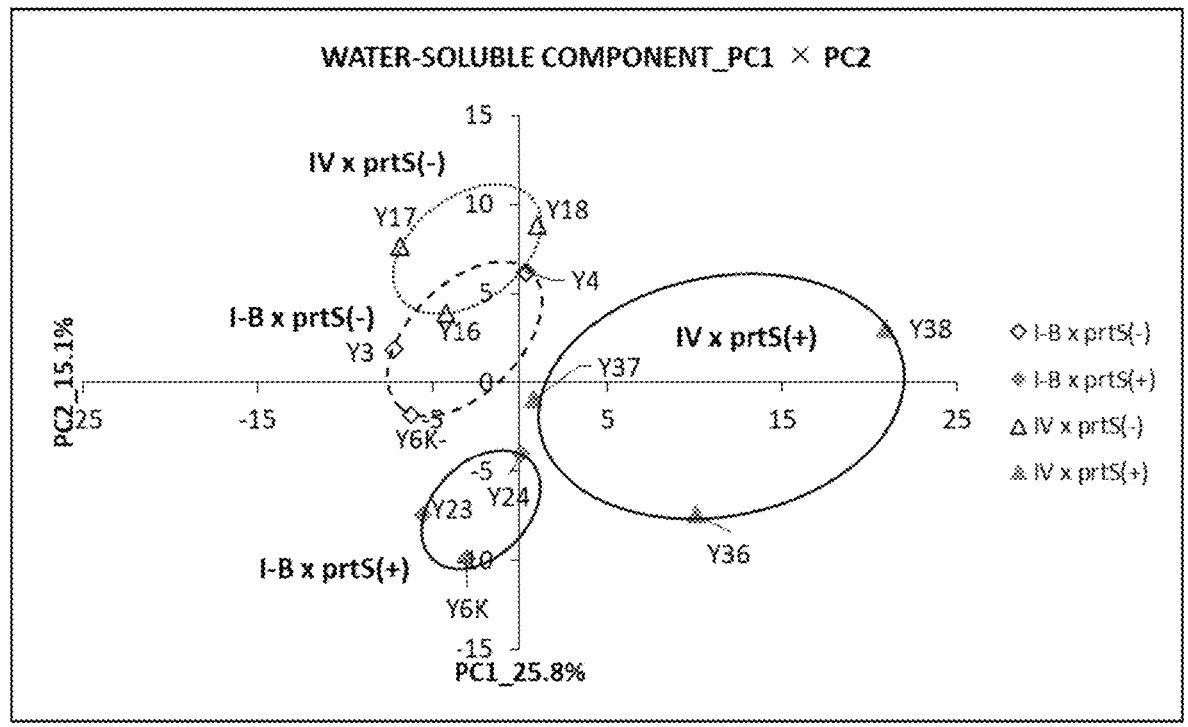
FIG. 12 is a diagram illustrating the relationship between the first principal component score (PC1) and the second principal component score (PC2) in the analysis result of water-soluble component (1)
Figure 13:
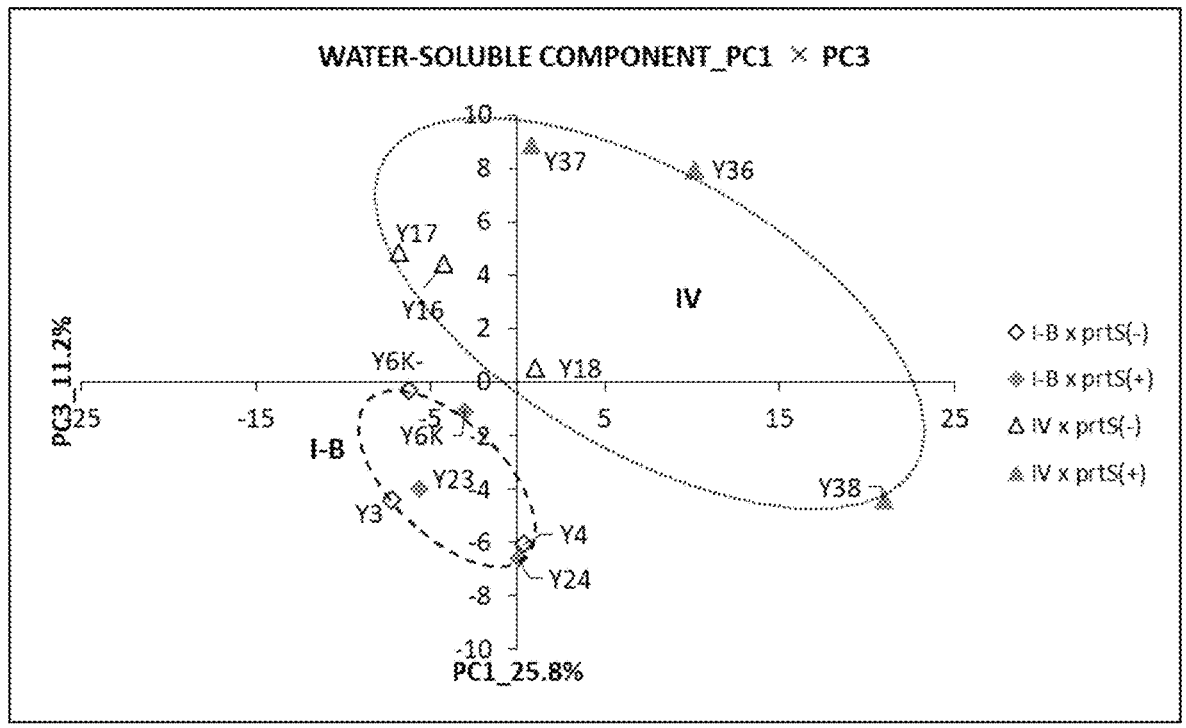
FIG. 13 is a diagram illustrating the relationship between the first principal component score (PC1) and the third principal component score (PC3) in the analysis result of water-soluble component (1)
Figure 14:
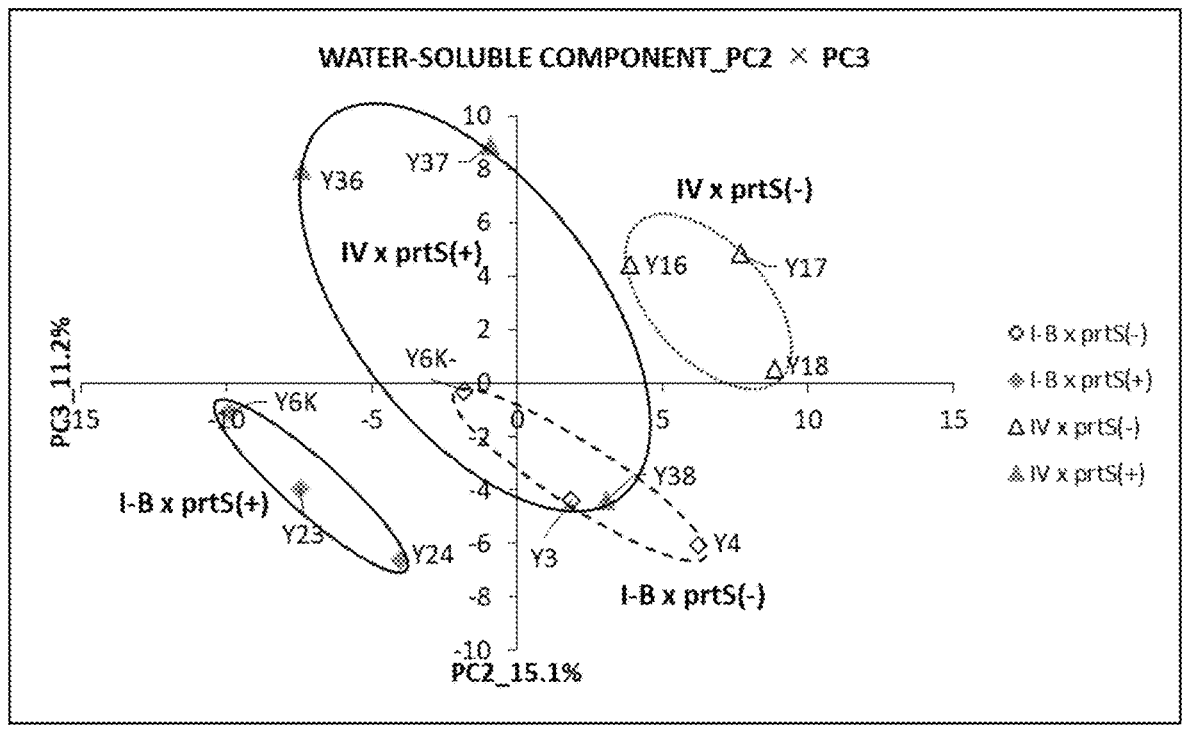
FIG. 14 is a diagram illustrating the relationship between the second principal component score (PC2) and the third principal component score (PC3) in the analysis result of water-soluble component (1)

(1) Principal component analysis (PCA) was performed on the water-soluble components in the fermented milk obtained by various combinations described in Table 6, where the combination is that of various *S. thermophilus* with *L. delbrueckii* classified into subcluster I-B of cluster I (*L. delbrueckii* (I-B)) or *L. delbrueckii* classified into cluster IV (*L. delbrueckii* (IV)). FIG. 11 and FIG. 12 illustrate the relationship between the first principal component score (PC1) and the second principal component score (PC2) in various types of fermented milk, FIG. 13 illustrates the relationship between the first principal component score (PC1) and the third principal component score (PC3), and FIG. 14 illustrates the relationship between the second principal component score (PC2) and the third principal component score (PC3). As illustrated in FIG. 11, the results were divided into two depending on the presence or absence of the prtS gene carried by *S. thermophilus* (prtS(+)/prtS(−)), suggesting that the presence or absence of the prtS gene had a significant effect on the water-soluble components in fermented milk. In addition, as illustrated in FIGS. 12 to 14, the results were also divided by the cluster of *L. delbrueckii*. In particular, in the case of using *S. thermophilus* prtS(+), the results were divided into two between *L. delbrueckii* (I-B) and *L. delbrueckii* (IV), suggesting that the cluster of *L. delbrueckii* also had an effect on the water-soluble components in fermented milk.

Figure 15:
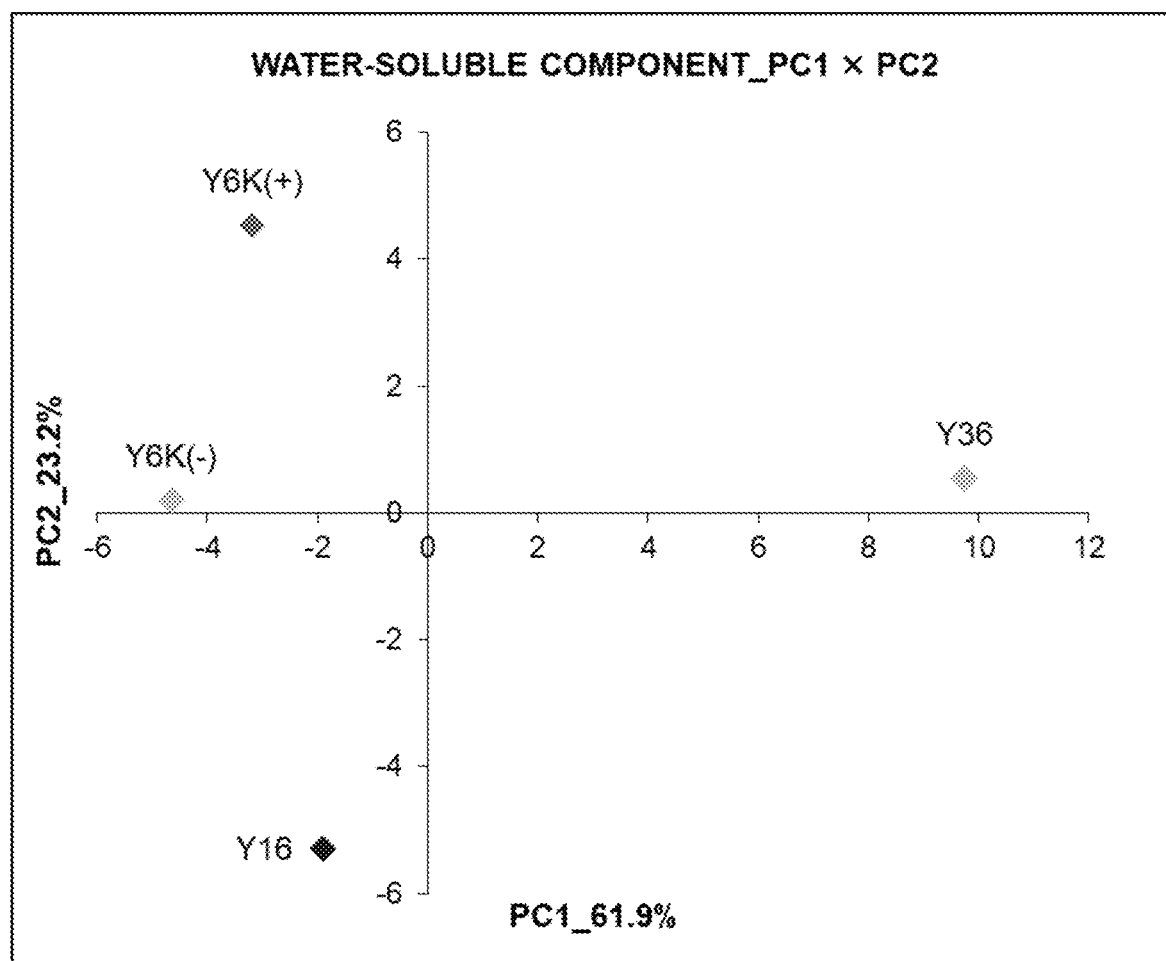
FIG. 15 is a diagram illustrating the relationship between the first principal component score (PC1) and the second principal component score (PC2) in the analysis result of water-soluble component (2)
Figure 16:
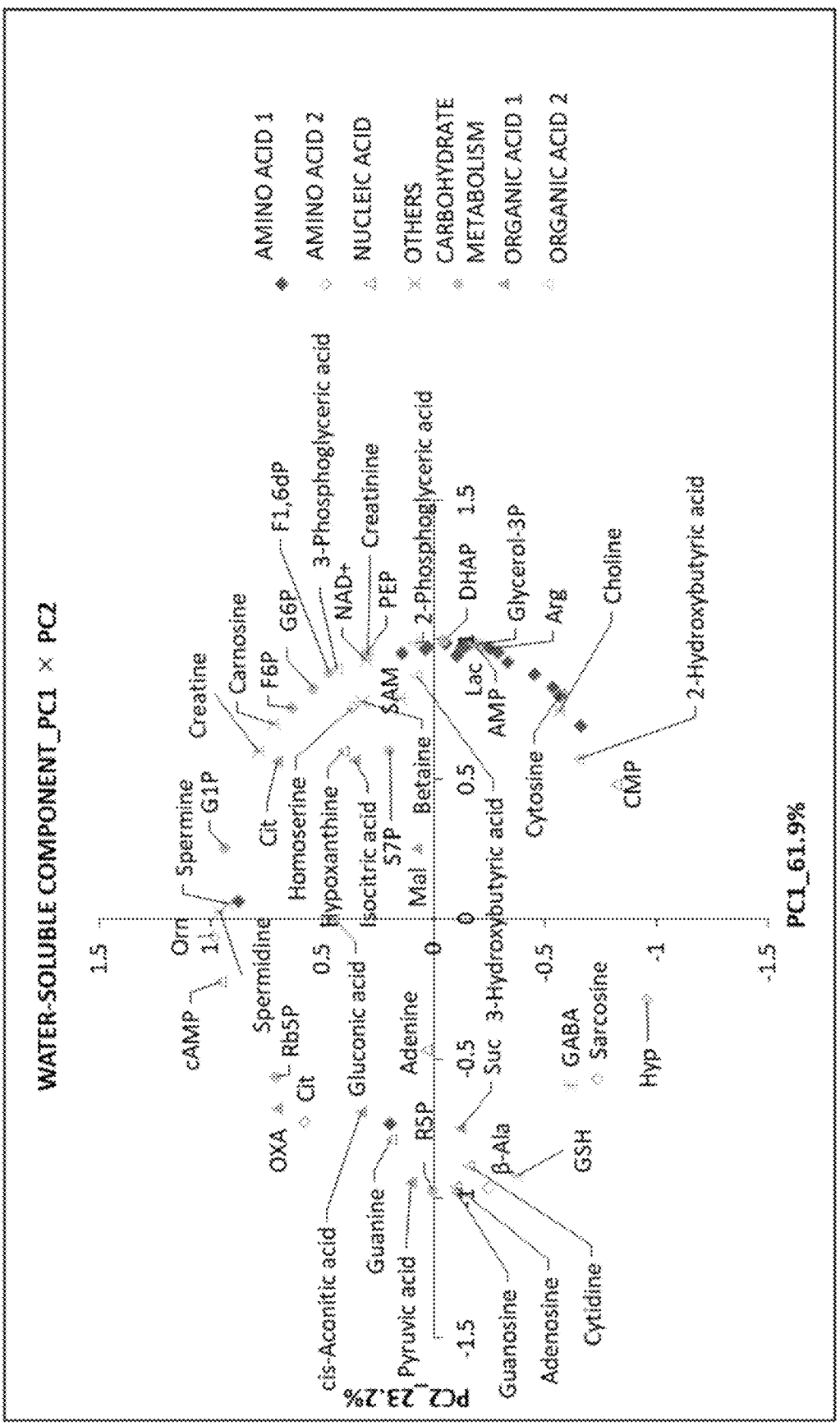
FIG. 16 is a scatter diagram of the water-soluble components corresponding to FIG. 15 in the analysis result of water-soluble component (2)

(2) Principal component analysis (PCA) was performed on the water-soluble components in the fermented milk obtained by combinations (Y16, Y36, Y6K(−), Y6K(+)) of various *S. thermophilus* with *L. delbrueckii* NITE ABP-02874 being *L. delbrueckii* classified into subcluster I-B of cluster I (*L. delbrueckii* specified by accession number NITE BP-02874 (receipt number NITE ABP-02874)) or *L. delbrueckii* 2038 being *L. delbrueckii* classified into cluster IV (isolated from Meiji Bulgaria Yogurt LB81 (manufactured by Meiji Co., Ltd.)). FIG. 15 illustrates the relationship between the first principal component score (PC1) and the second principal component score (PC2) in various types of fermented milk. In addition, FIG. 16 illustrates a scatter diagram of the water-soluble components corresponding to FIG. 15. As illustrated in FIGS. 15 and 16, those with higher amount of amino acid, carbohydrate metabolism-related substance, and lactic acid were plotted in the positive direction of the PC1 axis, and those with higher amount of ornithine and polyamine were plotted in the positive direction of the PC2 axis.

<Analysis of Aroma Component (in the Fermented Milk)>

In the above fermentation time measurement, the aroma components in the fermented milk obtained using various combinations of strains were analyzed by the dynamic headspace gas chromatography/mass spectrometry (GC/MS) method in accordance with the following method.

(Analysis Method)

To a 20-mL vial, 5 g of fermented milk, 5 g of 1 mol/L-phosphate buffer (pH 6.98), and methyl isobutyl ketone as the internal standard were added, and the vial was sealed. A dynamic headspace collection apparatus (manufactured by Gerstel Inc.) was used to replace the headspace with 10 mL of nitrogen gas while keeping the vial at 25° C., and the aroma components in the nitrogen gas were collected to an adsorbent (TENAX-TA). Next, the adsorbent was subjected to thermal desorption under the conditions presented in Table 9 below, and introduced and analyzed by GC/MS. The mass spectra of the detected peaks were compared with the NIST mass spectrum library to qualify the detected compound. Moreover, the peaks were integrated using ions specific to each compound to obtain a detected amount. In addition, if necessary, the value obtained by dividing the peak area by the peak area of the internal standard was used as the detection amount.

TABLE 9

| | |
|---|---|
| Thermal Desorption Apparatus | TDU (manufactured by Gerstel Inc.) |
| Thermal Desorption Temperature | 25° C. (0.5 min) → 720° C./min → 230° C. (5 min) |
| Cryofocus | −10° C. (0.5 min) → 720° C./min → 240° C. (10 min) |
| GCMS Apparatus | 6890GC/5975MS (manufactured by Agilent Technologies) |
| Column | DB-WAX UI inner diameter 0.25 mm × film thickness 0.25 μm × length 30 m |
| Oven | 40° C. (2.5 min) → 5° C./min → 80° C. → 10° C./min → 120° C. → 20° C./min → 240° C. (5 min) |
| Helium Gas | 1 mL/min |
| Scan Range | m/z 33 to 300 |

(Results)

Figure 17:
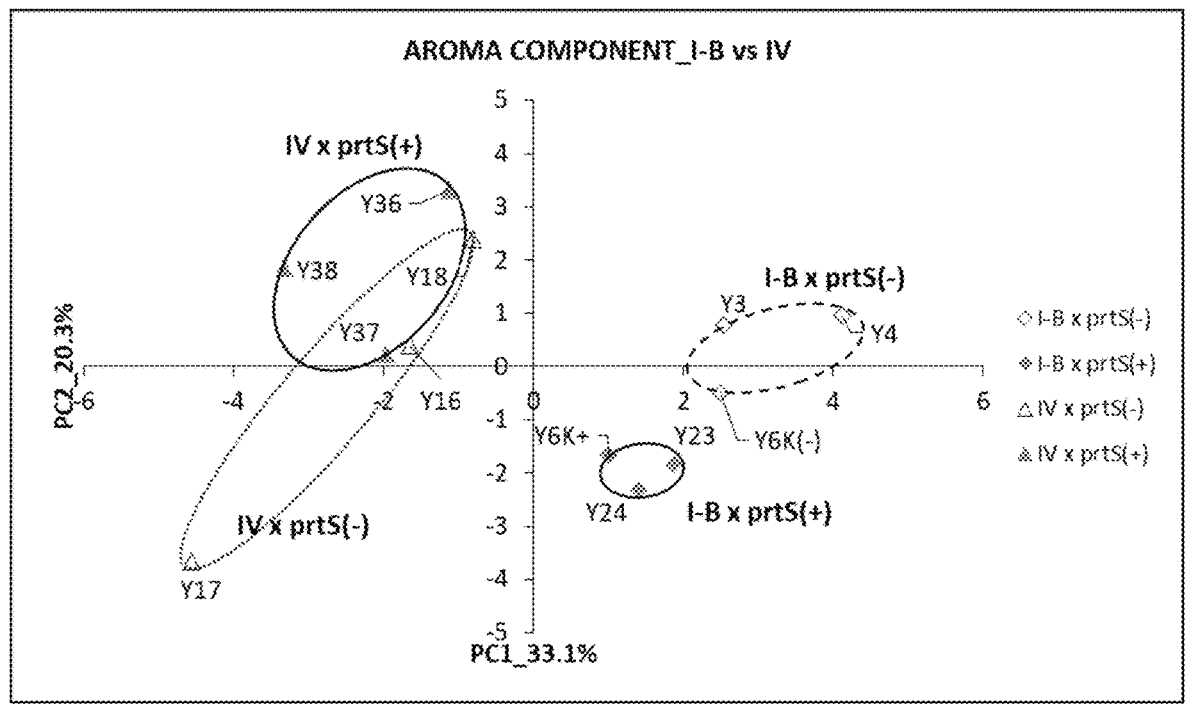
FIG. 17 is a diagram illustrating the relationship between the first principal component score (PC1) and the second principal component score (PC2) in the analysis result of aroma component (1)

(1) Principal component analysis (PCA) was performed on the aroma components in the fermented milk obtained by various combinations described in Table 6, where the combination is that of various *S. thermophilus* with *L. delbrueckii* (I-B) or *L. delbrueckii* (IV). FIG. 17 illustrates the relationship between the first principal component score (PC1) and the second principal component score (PC2) in various types of fermented milk. As illustrated in FIG. 17, also for the aroma components, the results were divided depending on the presence or absence of the prtS gene carried by *S. thermophilus* and on the difference in *L. delbrueckii* cluster, suggesting that *S. thermophilus* prtS(+) had a further effect on the aroma components in the fermented milk particularly in the case of using *L. delbrueckii* (I-B).

Figure 18:
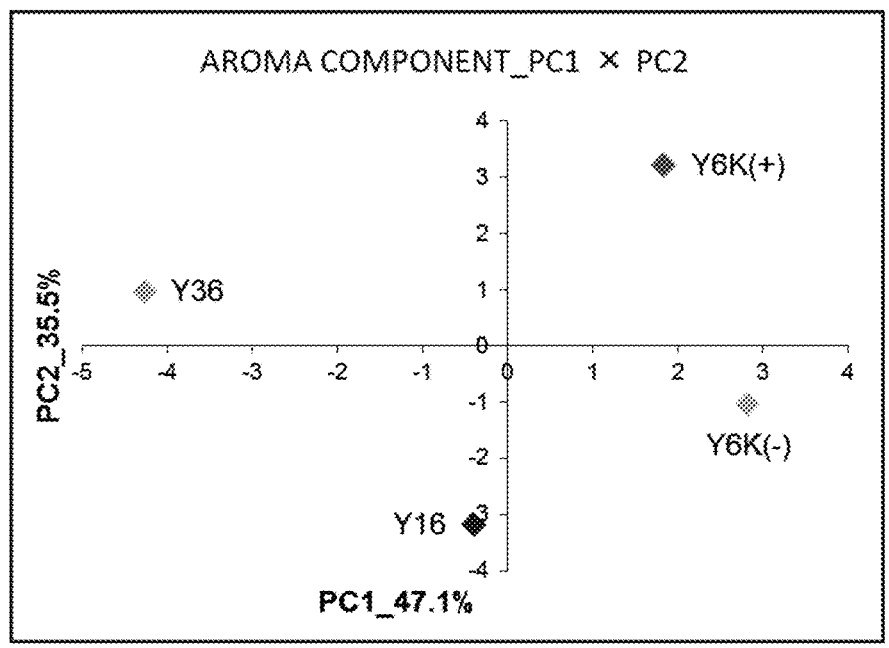
FIG. 18 is a diagram illustrating the relationship between the first principal component score (PC1) and the second principal component score (PC2) in the analysis result of aroma component (2)
Figure 19:
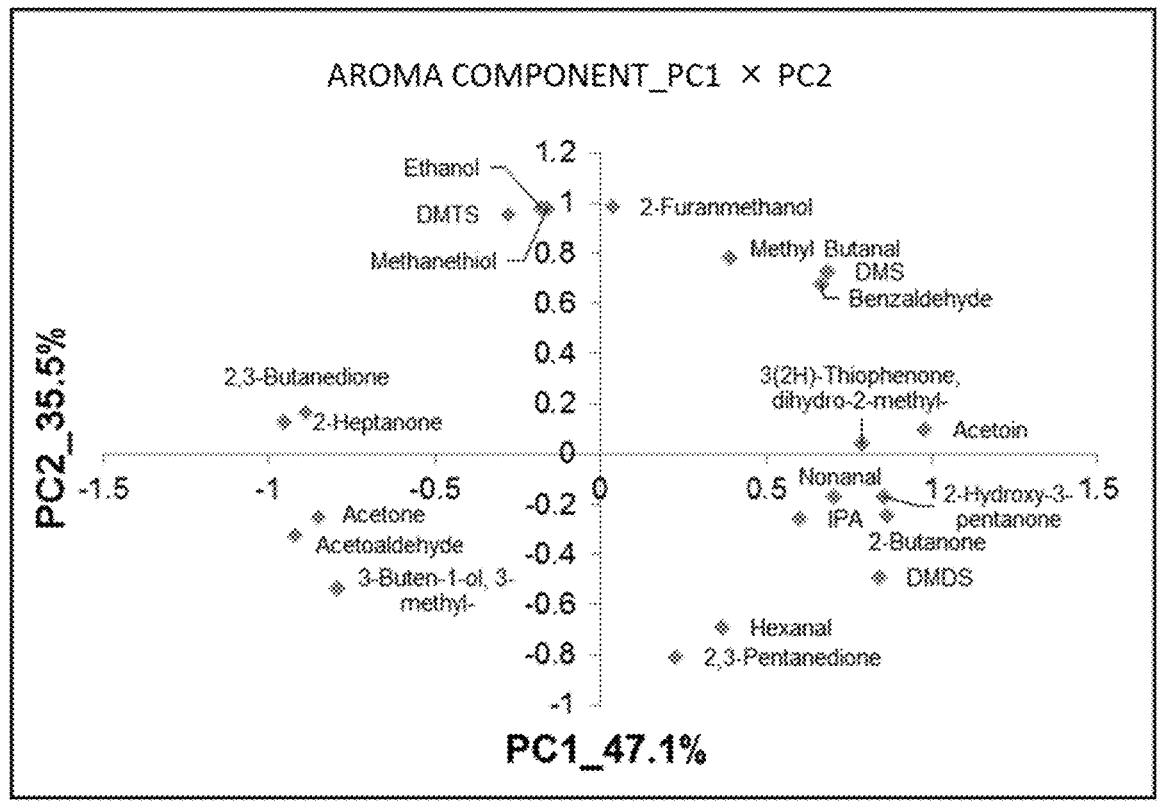
FIG. 19 is a scatter diagram of the aroma components corresponding to FIG. 18 in the analysis result of aroma component (2)

(2) Principal component analysis (PCA) was performed on the aroma components in the fermented milk obtained by combinations (Y16, Y36, Y6K(−), Y6K(+)) of various *S. thermophilus* with *L. delbrueckii* NITE ABP-02874 being *L. delbrueckii* classified into subcluster I-B of cluster I or *L. delbrueckii* 2038 being *L. delbrueckii* classified into cluster IV. FIG. 18 illustrates the relationship between the first principal component score (PC1) and the second principal component score (PC2) in various types of fermented milk. In addition, FIG. 19 illustrates a scatter diagram of the aroma components corresponding to FIG. 18. As illustrated in FIGS. 18 and 19, those with higher amount of acetaldehyde were plotted in the area with negative PC1 axis and negative PC2 axis, where the fermented milk using the combination (Y16) of *S. thermophilus* prtS(−) and *L. delbrueckii* (IV) (*L. delbrueckii* 2038) was plotted. Meanwhile, those with lower amount of acetaldehyde and higher amount of benzaldehyde (also known as an almond-like or apricot-like aroma), methylbutanal (also known as a burnt odor, malt odor or cocoa-like aroma), and DMS (also known as nori seaweed-like aroma or cow-like aroma) were plotted in the area with positive PC1 axis and positive PC2 axis, where the fermented milk using the combination (Y6K(+)) of *S. thermophilus* prtS(+) and *L. delbrueckii* (I-B) (*L. delbrueckii* NITE ABP-02874) was plotted.

<Sensory Evaluation>

In the above fermentation time measurement, the sensory evaluation of the fermented milk obtained using various combinations of strains presented in Table 6 was performed according to the following method.

(Evaluation Method)

The fermented milk after fermentation was immediately cooled on ice, and sensory evaluation was performed by a total of six trained panelists. The evaluation items were the following 11 items: acidity, sweetness, bitterness, umami, astringency/unpleasantness, milkiness, yogurtness, cheesiness (cream cheese-like), fattiness (butter-like or the like), milky full-bodiness/richness (cream-like or the like), and refreshing aftertaste, each of which was evaluated according to a 7-point scale of 1 to 7. The value obtained by averaging the evaluation results for six panelists was used as the sensory evaluation value.

(Results)

Figure 20:
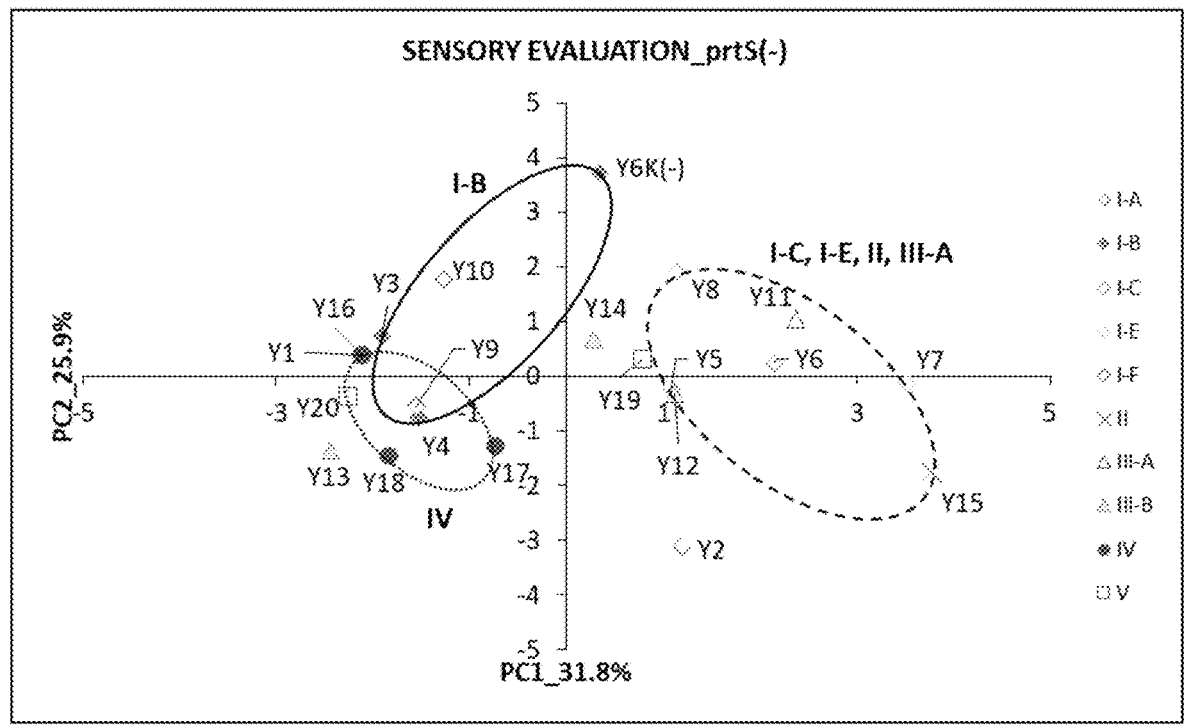
FIG. 20 is a diagram illustrating the relationship between the first principal component score (PC1) and the second principal component score (PC2) when using *S. thermophilus* prtS(−) in the sensory evaluation result (1)
Figure 21:
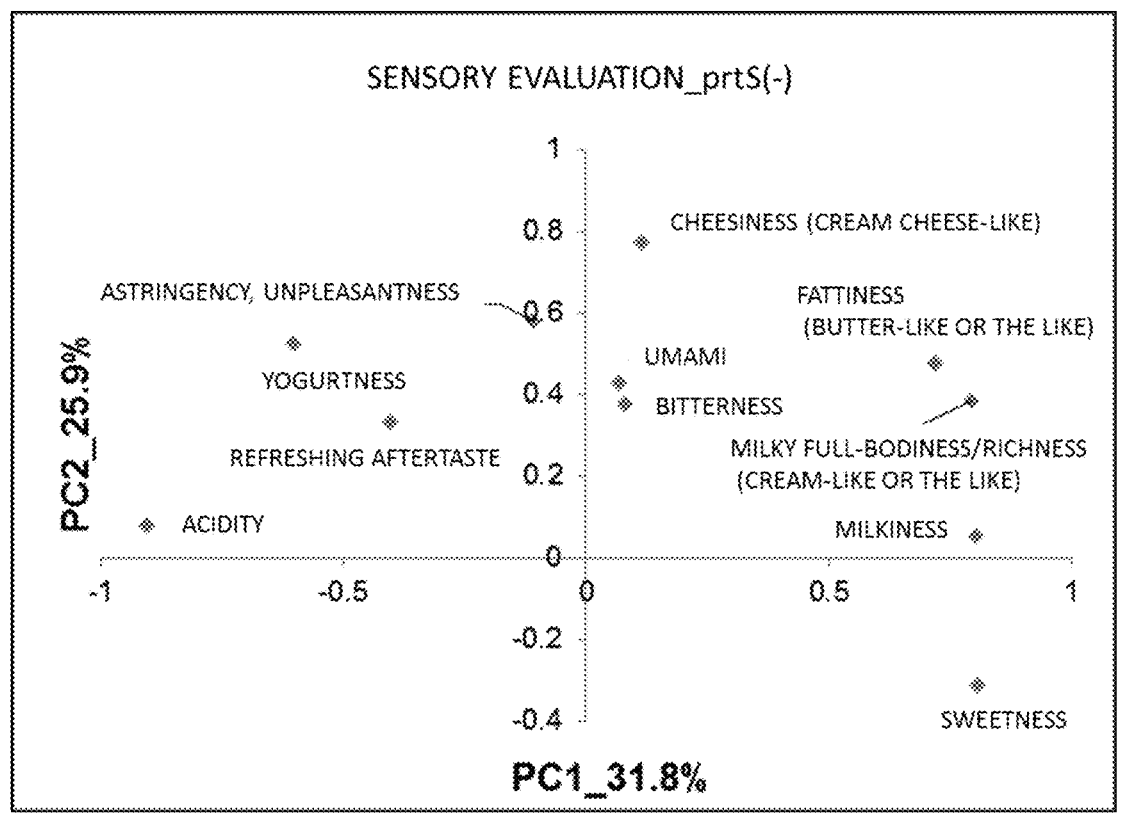
FIG. 21 is a scatter diagram of the sensory evaluation items corresponding to FIG. 20 in the sensory evaluation result (1)
Figure 22:
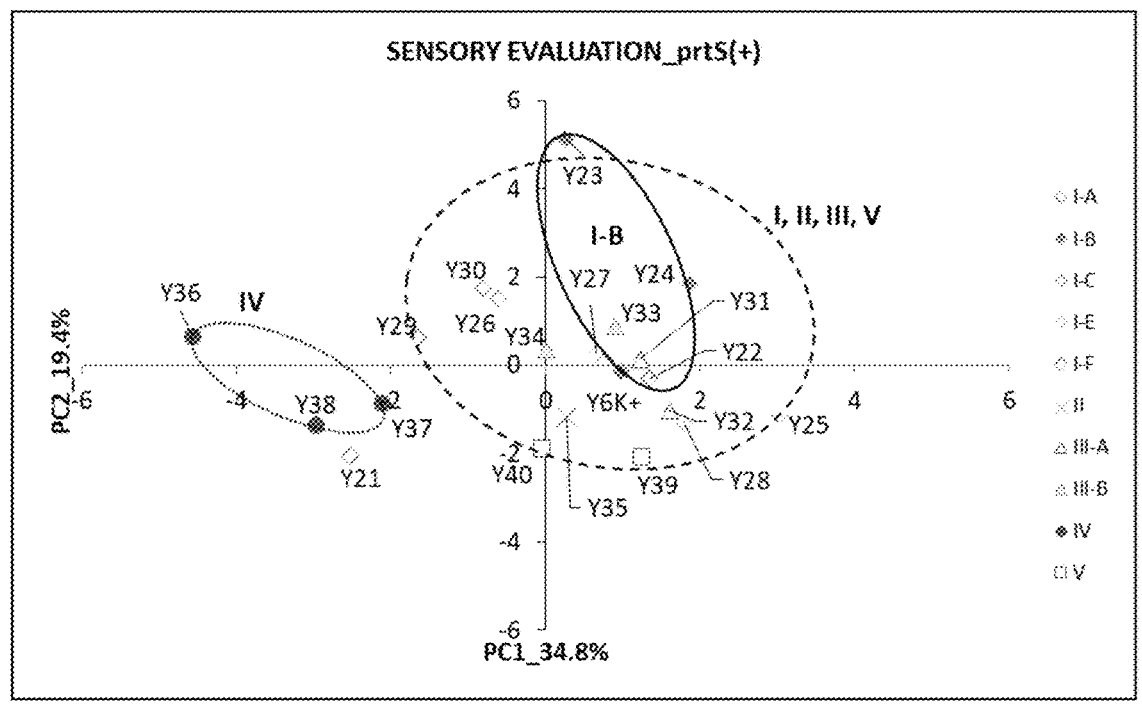
FIG. 22 is a diagram illustrating the relationship between the first principal component score (PC1) and the second principal component score (PC2) when using *S. thermophilus* prtS(+) in the sensory evaluation result (1)
Figure 23:
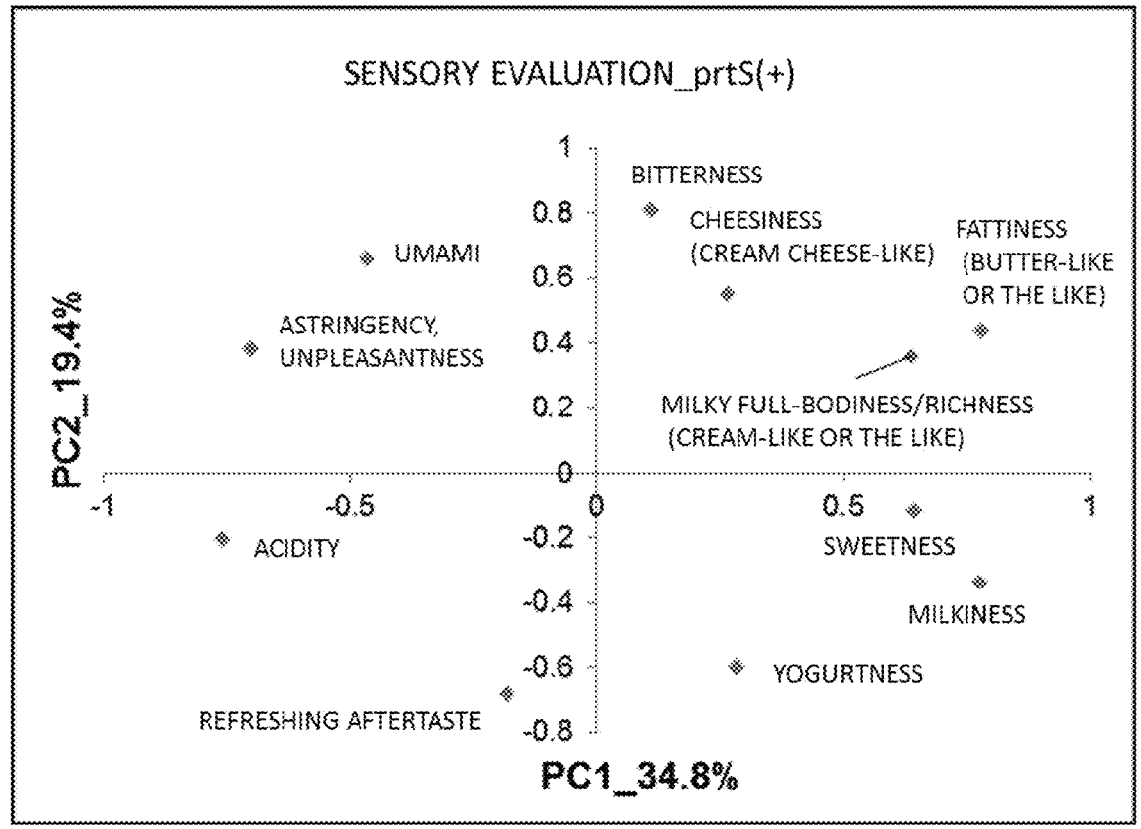
FIG. 23 is a scatter diagram of the sensory evaluation items corresponding to FIG. 22 in the sensory evaluation result (1)

(1) FIG. 20 presents a diagram illustrating the relationship between the first principal component score (PC1) and the second principal component score (PC2) in various types of fermented milk obtained by performing principal component analysis (PCA), relating to the sensory evaluation value of the fermented milk obtained by various combinations of *S. thermophilus* prtS(−) and various *L. delbrueckii* described in Table 6. In addition, FIG. 21 illustrates a scatter diagram of the sensory evaluation items corresponding to FIG. 20. Moreover, FIG. 22 presents a diagram illustrating the relationship between the first principal component score (PC1) and the second principal component score (PC2) in various types of fermented milk obtained by performing principal component analysis (PCA), relating to the sensory evaluation value of the fermented milk obtained by various combinations of *S. thermophilus* prtS(+) and various *L. del-brueckii*, and FIG. 23 illustrates a scatter diagram of the sensory evaluation items corresponding to FIG. 22.

As illustrated in FIG. 20 and FIG. 21, the results were such that, in fermented milk using *S. thermophilus* prtS(−) in combination with *L. delbrueckii* (IV), many of the panelists felt yogurtness and acidity, while in the fermented milk using *S. thermophilus* prtS(−) in combination with *L. delbrueckii* (I-B), many of the panelists felt umami and astringency. On the other hand, as illustrated in FIG. 22 and FIG. 23, in fermented milk using *S. thermophilus* prtS(+) in combination with *L. delbrueckii* (IV), many of the panelists felt acidity and astringency, while in fermented milk using *S. thermophilus* prtS(+) in combination with *L. delbrueckii* classified into clusters I, II, III, and V (particularly *L. delbrueckii* (I-B)), many of the panelists made an evaluation as having a well-balanced, mild flavor as a whole with a milky full-bodiness/richness and milkiness. As illustrated in FIG. 20 to FIG. 23, the results were divided depending on the *L. delbrueckii* cluster. In particularly, in the case of using *S. thermophilus* prtS (+), the results were largely divided into two between *L. delbrueckii* classified into clusters I, II, III, and V and *L. delbrueckii* (IV) classified into cluster IV. It was confirmed that the combination of *S. thermophilus* prtS(+) with *L. delbrueckii* classified into clusters I, II, III, and V (more preferably *L. delbrueckii* (I-B)) provided fermented milk with a particularly mild flavor.

Figure 24:
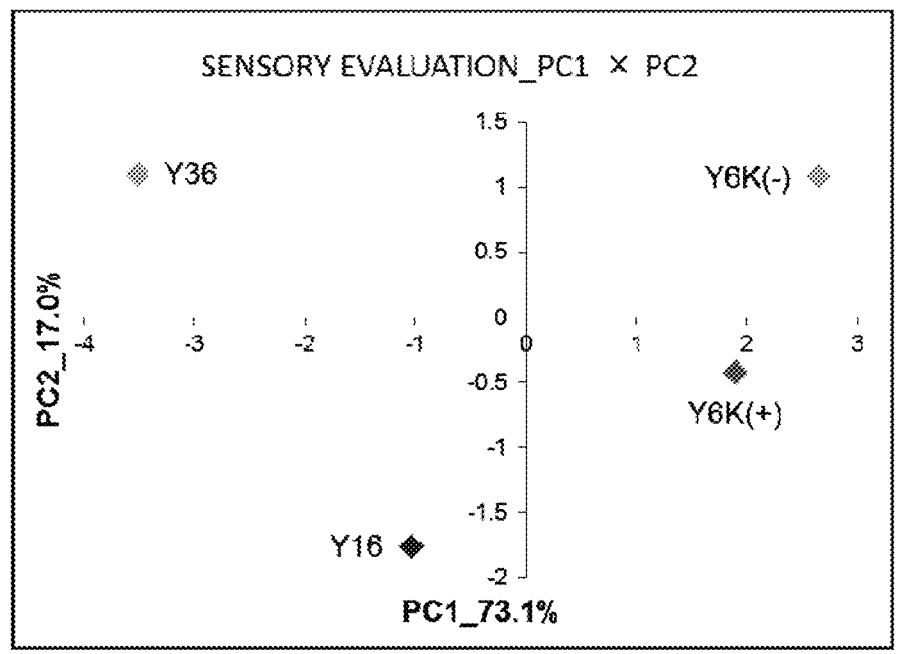
FIG. 24 is a diagram illustrating the relationship between the first principal component score (PC1) and the second principal component score (PC2) in the sensory evaluation result (2)

(2) FIG. 24 illustrates the relationship between the first principal component score (PC1) and the second principal component score (PC2) in various types of fermented milk, which was obtained by performing principal component analysis (PCA) on the sensory evaluation values of the fermented milk obtained by combinations (Y16, Y36, Y6K(−), Y6K(+)) of various *S. thermophilus* with *L. delbrueckii* NITE ABP-02874 being *L. delbrueckii* classified into subcluster I-B of cluster I or *L. delbrueckii* 2038 being *L. delbrueckii* classified into cluster IV. In addition, FIG. 25 illustrates a scatter diagram of the sensory evaluation items corresponding to FIG. 24.

Figure 25:
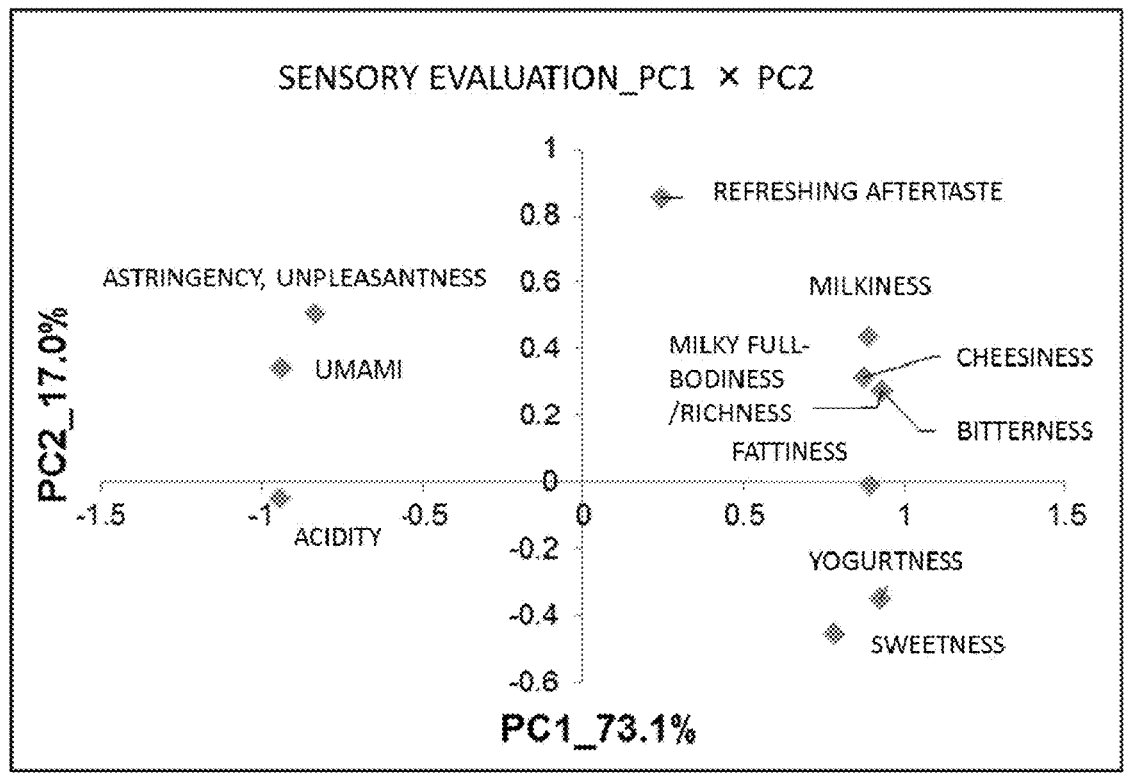
FIG. 25 is a scatter diagram of the sensory evaluation items corresponding to FIG. 24 in the sensory evaluation result (2)

As illustrated in FIG. 24 and FIG. 25, the fermented milk (Y16) using *S. thermophilus* prtS(−) in combination with *L. delbrueckii* (IV) (*L. delbrueckii* 2038) had a strong acidity, and the fermented milk (Y6K(−)) using a combination with *L. delbrueckii* (I-B) (*L. delbrueckii* NITE ABP-02874) had a weak umami and sweetness, where there was no significant difference from the flavor of milk before fermentation, and the flavor as fermented milk tended to be poor. Meanwhile, the fermented milk (Y36) using *S. thermophilus* prtS(+) in combination with *L. delbrueckii* (IV) (*L. delbrueckii* 2038) tended to have a strong astringency/unpleasantness and umami. In contrast, the fermented milk (Y6K(+)) using *S. thermophilus* prtS(+) in combination with *L. delbrueckii* (I-B) (*L. delbrueckii* NITE ABP-02874) tended to have a strong sweetness and yogurtness, and was evaluated as having a well-balanced mild flavor as a whole. In addition, it was confirmed that the fermented milk was clearly differentiated in flavor from fermented milk produced by other combinations of strains.

<Measurement of Lactic Acid Levels (in the Fermented Milk)>

In the above fermentation time measurement, the amounts of D-lactic acid and L-lactic acid in the fermented milk obtained using various combinations of strains presented in Table 6 were measured by high performance liquid chromatography (HPLC) in accordance with the following method.

(Measurement Method)

The fermented milk was diluted 2-fold with ultrapure water and deproteinized using the Carrez reagent. The supernatant after the deproteinization was filtered through a filter vial (PVDF, 0.2 μm, 1030-19022, manufactured by THOMSON), and the amounts of D-lactic acid and L-lactic acid (mM) in each type of fermented milk were measured under the following conditions:

- Guard column: SUMICHIRAL OA-5000 5 μm 4 mm i.d.×10 mm (manufactured by Sumika Chemical Analysis Service, Ltd.)
- Column: SUMICHIRAL OA-5000 4.6 mm i.d.×150 mm (manufactured by Sumika Chemical Analysis Service, Ltd.)
- Oven temperature: 40° C.
- Flow rate: 1.0 mL/min
- Detector: SPD-M20A (manufactured by Shimadzu Corporation)
- Injection volume: 10 μl
- Mobile phase: 2 mM $CuSO_4 \cdot 5H_2O$ +5% isopropanol (Results)

Figure 26:
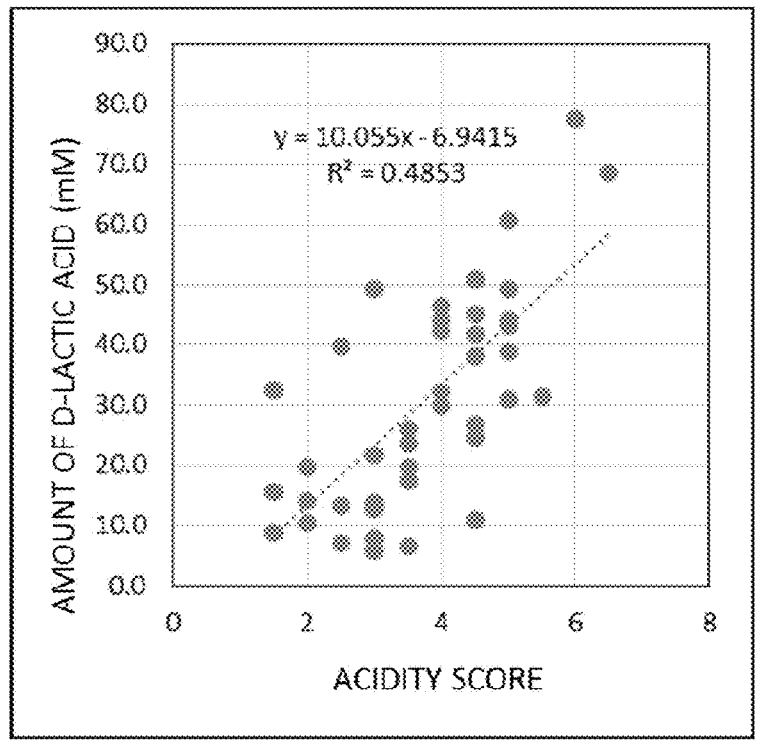
FIG. 26 is a graph illustrating the relationship between the amount of D-lactic acid and the acidity score in each type of fermented milk which results from a measurement of lactic acid (1)
Figure 27:
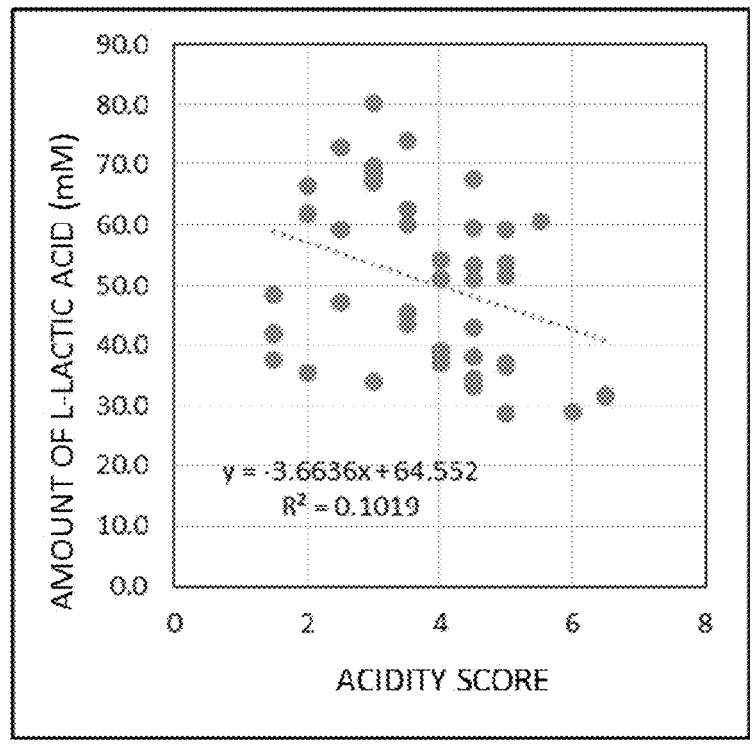
FIG. 27 is a graph illustrating the relationship between the amount of L-lactic acid and the acidity score in each type of fermented milk which results from a measurement of lactic acid (1)
Figure 28:
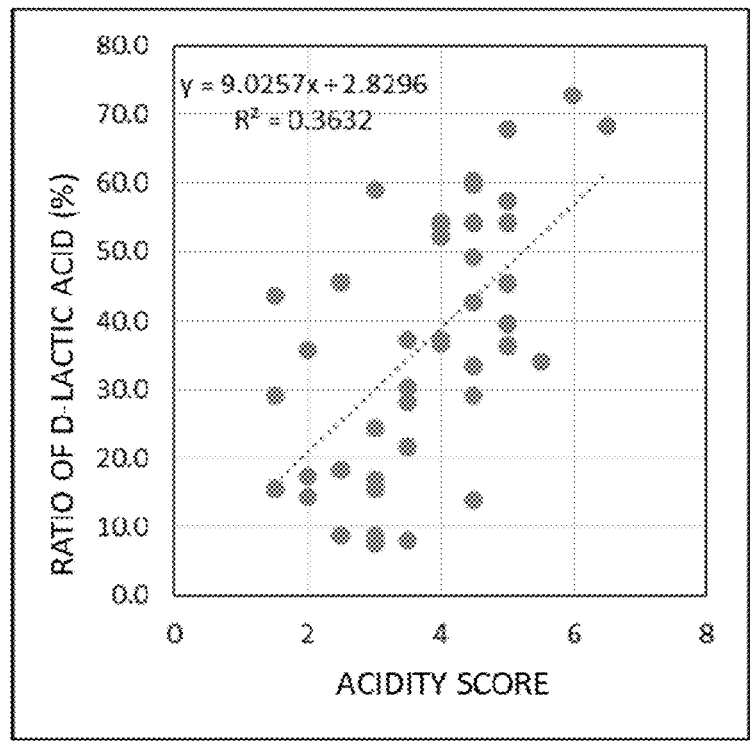
FIG. 28 is a graph illustrating the relationship between the ratio of D-lactic acid and the acidity score in each type of fermented milk which results from a measurement of lactic acid (1)

(1) FIG. 26 and FIG. 27 illustrate the relationship between the amounts of D-lactic acid and L-lactic acid (mM) in various types of fermented milk and the acidity score in the above-described sensory evaluation (the acidity score, the greater the score, the stronger the acidity). In addition, the ratio of D-lactic acid to the total amount of lactic acid in the fermented milk ({D-lactic acid amount/(D-lactic acid amount+L-lactic acid amount)}×100(%)) was calculated. FIG. 28 illustrates the relationship between the obtained ratio of D-lactic acid and the acidity score. As illustrated in FIGS. 26 to 28, the acidity score and the amount of D-lactic acid exhibited a positive correlation, and the acidity score and the amount of L-lactic acid exhibited a negative correlation. In addition, it was revealed that the higher the ratio of D-lactic acid, the higher the acidity score. From this, it was confirmed that as the ratio of D-lactic acid was smaller, the fermented milk had a lower acidity, that is, a milder flavor.

Figure 29:
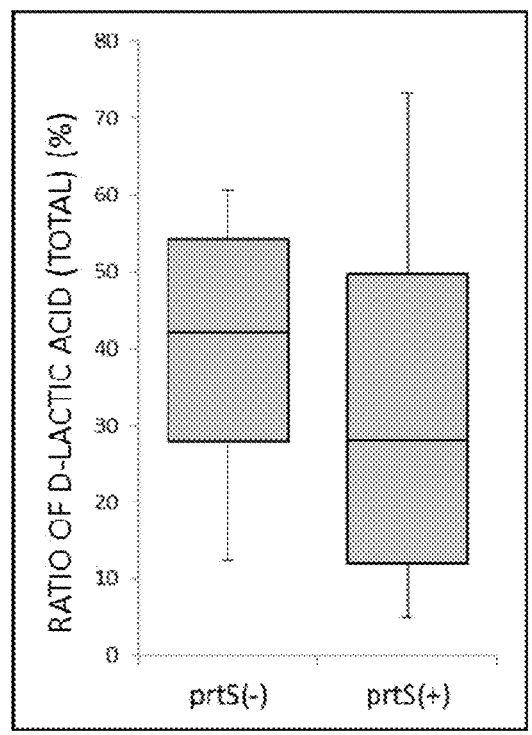
FIG. 29 is a graph illustrating the ratio of D-lactic acid in each type of fermented milk when using *S. thermophilus* prtS(−) and when using *S. thermophilus* prtS(+), each for the case of using *L. delbrueckii* classified into clusters I to V (all) which results from a measurement of lactic acid (2)

(2) FIG. 29 illustrates a graph comparing the ratio of D-lactic acid in the fermented milk for each *S. thermophilus*. Specifically, the figure illustrates the ratios of D-lactic acid (total) in the fermented milk (average values, %) when using *S. thermophilus* prtS(−) and *L. delbrueckii* (prtS(−): Y1 to Y20, Y6K(−), n=21) and when using *S. thermophilus* prtS (+) and *L. delbrueckii* (prtS(+): Y21 to Y40, Y6K(+), n=21).

Figure 30:
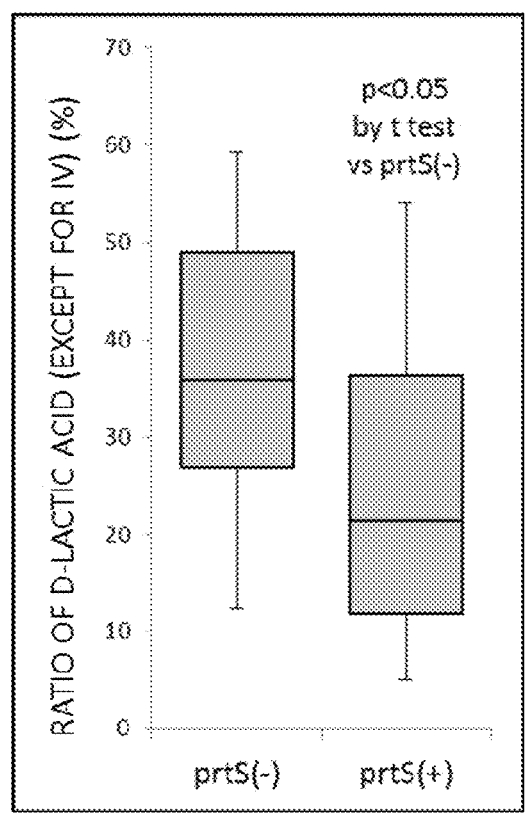
FIG. 30 is a graph illustrating the ratio of D-lactic acid in each type of fermented milk when using *S. thermophilus* prtS(−) and when using *S. thermophilus* prtS(+), each for the case of using *L. delbrueckii* classified into clusters I, II, III, V (except for IV) which results from a measurement of lactic acid (2)

In addition, FIG. 30 illustrates a graph comparing the ratio of D-lactic acid in the fermented milk obtained by combining various *S. thermophilus* with *L. delbrueckii* classified into a cluster except for IV (*L. delbrueckii* (except for IV)). Specifically, the figure illustrates the ratios of D-lactic acid (except for IV) in the fermented milk (average values, %) when using *S. thermophilus* prtS(−) and *L. delbrueckii* (except for IV) (prtS(−): Y1 to Y15, Y19 to Y40, Y6K(−), n=18) and when using *S. thermophilus* prtS(+) and *L. delbrueckii* (except for IV) (prtS(+): Y21 to Y35, Y39-Y40, Y6K(+), n=18).

As illustrated in FIG. 29, for each *S. thermophilus*, the comparison of the ratio of D-lactic acid in fermented milk was made on *L. delbrueckii* classified into clusters I to V, but no significant difference was recognized. On the other hand, as illustrated in FIG. 30, in the case of *L. delbrueckii* (except for IV), that is, *L. delbrueckii* classified into clusters I, II, III, and V, the ratio of D-lactic acid in fermented milk using *S. thermophilus* prtS(+) in combination was significantly lower than that in the fermented milk using *S. thermophilus* prtS(−) in combination (P-value by t-test was less than 0.05). Thus, it was confirmed that, when combined with *S. thermophilus* prtS (+), the fermented milk had a lower acidity, that is, a milder flavor.

<Examination on *S. Thermophilus* Strains>

The effects in the case of using strains of *S. thermophilus* except for *S. thermophilus* NITE ABP-02875 described above were examined. The examination was carried out by using the strains of *S. thermophilus* carrying no prtS gene (*S. thermophilus* prtS (−):MEP1900415, MEP1900416, MEP1900417, and MEP1900418) and the strains of *S. thermophilus* carrying a prtS gene (*S. thermophilus* prtS(+): MEP1900419, MEP1900420, MEP1900421, and MEP1900422), both of which had been confirmed for the presence or absence of prtS gene carried. All of these strains assigned numbers beginning with "MEP" are stored by Meiji Innovation Center of MeijiCo., Ltd. (postal code: 192-0919, 1-29-1 Nanakuni, Hachioji-shi, Tokyo, Japan).

Figure 31:
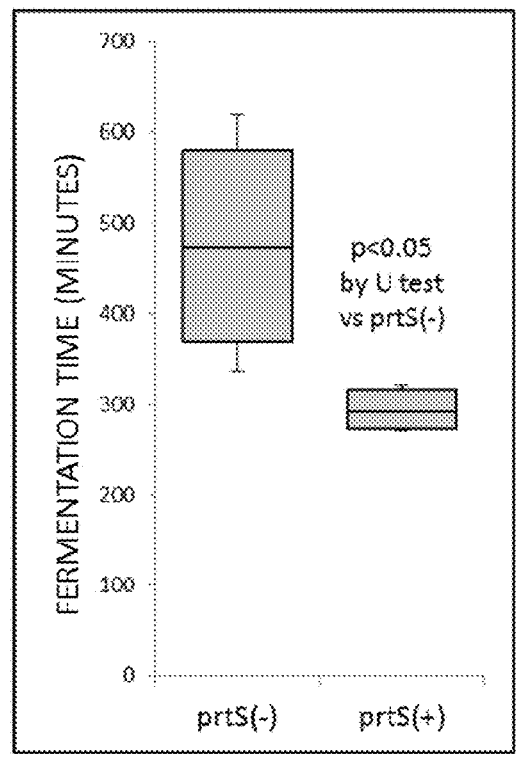
FIG. 31 is a graph illustrating fermentation times when using *S. thermophilus* prtS(−) and when using *S. thermophilus* prtS(+) in the examination on *S. thermophilus* strains (1)

(1) The above-described various *S. thermophilus* prtS(−) and *L. delbrueckii* NITE ABP-02874 were used in combination to measure the time required for fermentation. Specifically, each strain was subjected to activation culture twice at 37° C. for 16 hours in a 10% skimmed milk medium (sterilized at 121° C. for 7 minutes) prepared with 10% (wt/wt) skimmed milk powder and 0.1% (wt/wt) yeast extract. These strains were combined and added to a 10% skimmed milk medium (sterilized until reaching at 95° C.) to a total concentration of 1% (*L. delbrueckii*:*S. thermophilus*=about 1:1 (bacterial count)), followed by fermentation at 43° C. for 24 hours (aerobic, static culture) to obtain various types of fermented milk. The time from the addition of each strain until the pH reached 4.5 was measured and defined as the fermentation time required for fermentation. In addition, the time required for fermentation was measured in the same manner as described above, using combinations of the above-described various *S. thermophilus* prtS(+) and *L. delbrueckii* NITE ABP-02874. FIG. 31 illustrates fermentation times (average values, minutes) when using *S. thermophilus* prtS(−) (prtS(−), n=4) and using *S. thermophilus* prtS (+) (prtS (+), n=4). As a result of the Mann-Whitney U test, the result for prtS (+) was such that the P-value was less than 0.05 for the result of prtS(−). As illustrated in FIG. 31, it was confirmed that, also in the case of using *S. thermophilus* prtS(+) except for *S. thermophilus* NITE ABP-02875, the fermentation time was significantly reduced as compared with the case of using *S. thermophilus* prtS(−), as in the case of using *S. thermophilus* NITE ABP-02875.

Figure 32:
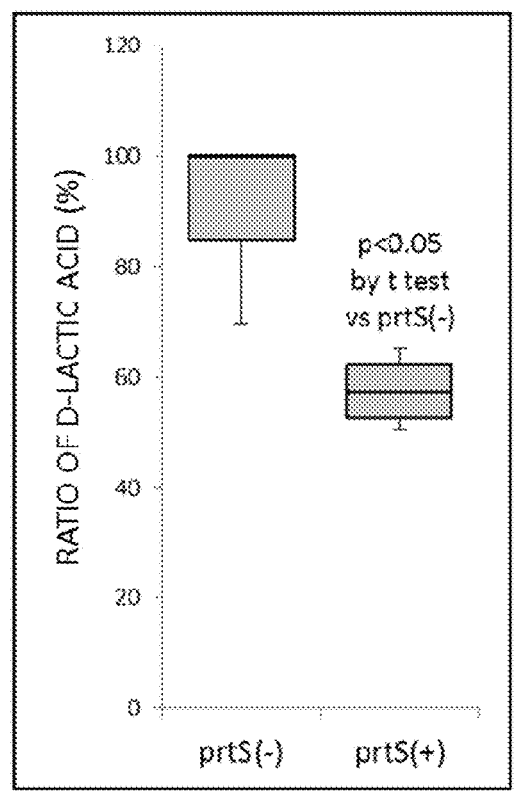
FIG. 32 is a graph illustrating the ratio of D-lactic acid in each type of fermented milk when using *S. thermophilus* prtS(−) and when using *S. thermophilus* prtS(+) the examination on *S. thermophilus* strains(2).

(2) The ratio of D-lactic acid in the fermented milk obtained by using the combination of the various *S. thermophilus* prtS (−) and *L. delbrueckii* NITE ABP-02874 of (1) above was measured and calculated in the same manner as in the above-described measurement of the amount of lactic acid. In addition, the ratio of D-lactic acid in the fermented milk obtained by using the combination of the various *S. thermophilus* prtS(+) and *L. delbrueckii* NITE ABP-02874 of (1) above was measured and calculated in the same manner as in the above-described measurement of the amount of lactic acid. FIG. 32 illustrates the ratios (average values, %) of D-lactic acid when using *S. thermophilus* prtS(−) (prtS(−), n=4) and when using *S. thermophilus* prtS (+) (prtS (+), n=4). As a result of the t-test, the result for prtS(+) was such that the P-value was less than 0.05 for the result of prtS(−). As illustrated in FIG. 32, it was confirmed that, also in the fermented milk obtained by using *S. thermophilus* prtS(+) except for *S. thermophilus* NITE ABP-02875, the ratio of D-lactic acid was significantly reduced as compared with the fermented milk obtained by using *S.*

*thermophilus* prtS(−), as in the case of using *S. thermophilus* NITE ABP-02875, and the fermented milk had a lower acidity and milder flavor.

As has been described above, the present invention makes it possible to provide a method for producing fermented milk using a *Lactobacillus* species and *Streptococcus thermophilus*, a lactic acid bacterium and a lactic acid bacteria-containing composition which can be used therein, and fermented milk obtained therefrom. The method for producing fermented milk makes it possible to produce fermented milk even when using *Lactobacillus delbrueckii* which has no lactose utilization and to obtain fermented milk having a balanced and mild flavor in all of acidity, umami, fermented aroma, and richness.

What is claimed is:

1. A combined product comprising:

a *Lactobacillus delbrueckii* and a *Streptococcus thermophilus* carrying a prtS gene, wherein the *Lactobacillus delbrueckii* is *Lactobacillus delbrueckii* classified into any one of clusters I, II, III, and V by multilocus sequence analysis (MLSA) classification based on seven housekeeping genes consisting of fusA gene, gyrB gene, hsp60 gene, ileS gene, pyrG gene, recA gene, and recG gene.

2. The combined product according to claim 1, wherein the *Streptococcus thermophilus* carrying the prtS gene is *Streptococcus thermophilus* specified by accession number NITE BP-02875.

3. The combined product according to claim 1, wherein the *Lactobacillus delbrueckii* is satisfying all of the following conditions (i) to (vii):

(i) carrying an fusA gene whose allele number is 2 or 14,
(ii) carrying a gyrB gene whose allele number is any one selected from 3, 17, 18, and 25,
(iii) carrying an hsp60 gene whose allele number is any one selected from 4, 18, 26, and 27,
(iv) carrying an ileS gene whose allele number is any one selected from 16, 20, 21, 30, and 33,
(v) carrying a pyrG gene whose allele number is 22 or 23,
(vi) carrying an recA gene whose allele number is any one selected from 2, 7, 24, and 28, and
(vii) carrying an recG gene whose allele number is 3, or the *Lactobacillus delbrueckii* is classified into the same cluster as that of the *Lactobacillus delbrueckii* satisfying all of the conditions (i) to (vii) by MLSA classification based on seven housekeeping genes consisting of fusA gene, gyrB gene, hsp60 gene, ileS gene, pyrG gene, recA gene, and recG gene.

4. The combined product according to claim 1, wherein the *Lactobacillus delbrueckii* is specified by accession number NITE BP-02874, or the *Lactobacillus delbrueckii* is classified into the same cluster as that of the *Lactobacillus delbrueckii* specified by accession number NITE BP-02874 by MLSA classification based on seven housekeeping genes consisting of fusA gene, gyrB gene, hsp60 gene, ileS gene, pyrG gene, recA gene, and recG gene.

5. The combined product according to claim 1, wherein the *Lactobacillus delbrueckii* is *Lactobacillus delbrueckii* specified by accession number NITE BP-02874.

6. The combined product according to claim 1, wherein the *Lactobacillus delbrueckii* has no lactose utilization.

* * * * *